United States Patent
Shida et al.

(10) Patent No.: US 10,253,118 B2
(45) Date of Patent: Apr. 9, 2019

(54) CYANINE COLORING COMPOSITION

(71) Applicant: Wako Pure Chemical Industries, Ltd., Osaka-shi, Osaka (JP)

(72) Inventors: Yukihiko Shida, Kawagoe (JP); Katsufumi Suzuki, Kawagoe (JP); Tomoaki Horie, Kawagoe (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 302 days.

(21) Appl. No.: 15/123,854

(22) PCT Filed: Mar. 5, 2015

(86) PCT No.: PCT/JP2015/056528
§ 371 (c)(1),
(2) Date: Sep. 6, 2016

(87) PCT Pub. No.: WO2015/133578
PCT Pub. Date: Sep. 11, 2015

(65) Prior Publication Data
US 2017/0015765 A1    Jan. 19, 2017

(30) Foreign Application Priority Data

Mar. 7, 2014 (JP) .................................. 2014-045375
Jan. 26, 2015 (JP) .................................. 2015-012761

(51) Int. Cl.
| | |
|---|---|
| *C08F 120/68* | (2006.01) |
| *C09B 69/10* | (2006.01) |
| *C08J 5/00* | (2006.01) |
| *G02B 5/22* | (2006.01) |
| *C07D 209/16* | (2006.01) |
| *G02B 1/04* | (2006.01) |
| *C09B 23/10* | (2006.01) |

(52) U.S. Cl.
CPC .......... *C08F 120/68* (2013.01); *C07D 209/16* (2013.01); *C08J 5/00* (2013.01); *C09B 23/105* (2013.01); *C09B 69/105* (2013.01); *G02B 1/04* (2013.01); *G02B 5/223* (2013.01); *C08F 2500/13* (2013.01); *C08F 2800/20* (2013.01); *C08J 2333/08* (2013.01)

(58) Field of Classification Search
None
See application file for complete search history.

(56) References Cited

FOREIGN PATENT DOCUMENTS

| | | |
|---|---|---|
| JP | 2-93422 A | 4/1990 |
| JP | 2010-37545 A | 2/2010 |
| JP | 2011-145540 A | 7/2011 |
| JP | 2012-208474 A | 10/2012 |
| JP | 2013-54275 A | 3/2013 |
| JP | 2013-136739 A | 7/2013 |

OTHER PUBLICATIONS

International Search Report dated May 19, 2015, issued in counterpart International Application No. PCT/JP2015/056528 (1 page).

*Primary Examiner* — Catherine S Branch
(74) *Attorney, Agent, or Firm* — Westerman, Hattori, Daniels & Adrian, LLP

(57) ABSTRACT

It is an object of the present invention to provide a cyanine-based coloring composition having higher heat resistance, as compared with a conventional coloring composition. The present invention relates to a compound represented by the following general formula (1), a polymer having a monomer unit derived from the compound, along with a coloring composition, a coloring composition for a color filter, and a colored resin comprising the above-described compound or the above-described polymer.

(1)

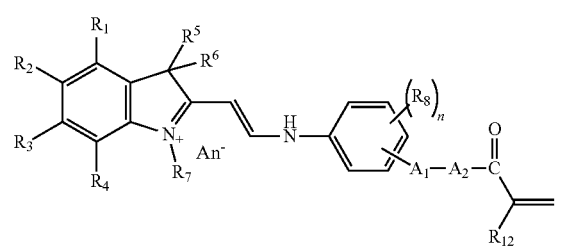

18 Claims, No Drawings

CYANINE COLORING COMPOSITION

TECHNICAL FIELD

The present invention relates to a cyanine-based coloring compound; a polymer having a monomer unit derived from the compound; and a coloring composition comprising the polymer.

BACKGROUND ART

As a method for forming a color pixel in manufacturing a color filter of a liquid crystal display element, a solid-state image sensing element, and the like, a dyeing method or a dye-dispersion method employing a dye for a colorant, a pigment-dispersion method using a pigment, an electrodeposition method, a printing method, and the like, has been known. In recent years, as characteristics of the color filter, enhancement of brightness and contrast has particularly been required. According to the pigment-dispersion method using a pigment, because the pigment has higher heat resistance and light resistance as compared with a dye, a color pixel having less deterioration at heating process in manufacturing a panel, and also having high long-term reliability can be obtained. Therefore, at present, the pigment-dispersion method has become the mainstream. However, when a pigment was used, because the pigment itself has relatively large particle size, there was a problem of decrease in contrast caused by light scattering. Although an attempt has also been made to micronize the pigment, there is a limit also in micronization, and it has also been a problem to secure dispersion stability of the micronized pigment.

On the other hand, as a method which is capable of resolving these problems, a method for forming the color pixel using a dye has been studied at present. When the dye is used, contrast is enhanced because light scattering is suppressed. However, because the dye has lower heat resistance as compared with a pigment, and sublimation depending on the type, there were problems such as reduction in brightness, fading and hue change. Therefore, to use the dye, it has been required to resolve this problem.

On the other hand, as a yellow dye for the color filter, a cyanine-based coloring compound, a barbituric acid azo-based coloring compound (PATENT LITERATURE 1), an azo-based coloring compound (PATENT LITERATURE 2), a pyridone azo-based coloring compound (PATENT LITERATURE 3), and the like, have usually been used. However, an azo group in the azo-based compounds has been known to inhibit a radical reaction. Accordingly, in the case of producing the color filter using the azo-based compound, a cored film having sufficient strength may not be obtained, due to not proceeding of a polymerization reaction.

In addition, a dye having an absorption band at a certain specific wavelength blocks out light having harmful wavelength, or reduces transmittance thereof. Accordingly, addition thereof to various products is capable of acquiring a role as a filter. For example, a dye which cuts blue light (visible rays of 380 to 500 nm), known as a wavelength range harmful to eyes, can be used suitably for spectacle lens, and a peripheral material such as a frame and a cover thereof. As an example, there has been known a dyeing method by permeation or diffusion of a dye on to a lens surface (PATENT LITERATURE 4). However, because it is surface fabrication, uniform dyeing may not be attained in some cases. In addition, there is such a different method as preparing a plastic lens for blocking out UV up to 400 nm, by mixing an UV absorbent into a specified monomer and polymerizing it (PATENT LITERATURE 5). However, because the UV absorbent is not directly bonded to a monomer, there was a problem of easily generating dyeing irregularity in polymerization, and the like.

CITATION LIST

Patent Literature

[PATENT LITERATURE 1] JP-A-2012-208474
[PATENT LITERATURE 2] JP-A-2011-145540
[PATENT LITERATURE 3] JP-A-2013-136739
[PATENT LITERATURE 4] JP-A-2013-54275
[PATENT LITERATURE 5] JP-A-2-93422

SUMMARY OF INVENTION

Technical Problem

It is an object of the present invention to provide a cyanine-based coloring composition having higher heat resistance, as compared with a conventional coloring composition.

Solution to Problem

In view of the circumstance, the present inventors considered to use a cyanine-based compound instead of an azo-based compound, as a raw material of a coloring composition. However, because a conventional cyanine-based compound was not able to provide heat resistance in a practical range, the present inventors have discovered, as a result of intensive study, that the coloring composition having excellent heat resistance is obtained by using a cyanine-based compound which has an anion having a specific structure, as a counter anion, as well as an ethylenically unsaturated bond, or a polymer having a monomer unit derived from the compound, as a dye, and have completed the present invention. Because of having extremely higher heat resistance as compared with a general dye, the coloring composition of the present invention can be used also in coloring of a resin and the like, whose injection molding temperature over 200° C., without any trouble. In addition, by using the coloring composition of the present invention as a polymer, not only bleed out in long term use and elution into a solvent, such as ethanol, can be suppressed, but also more uniform dyeing can be attained as compared with a conventional dye, because of having an ethylenically unsaturated group within a molecule of the compound of the present invention.

That is, the present invention relates to a compound represented by the following general formula (1), a polymer having a monomer unit derived from the compound represented by the following general formula (1), a coloring composition comprising the above-described compound or the above-described polymer, as well as a coloring composition for a color filter, comprising the above-described compound or the above-described polymer.

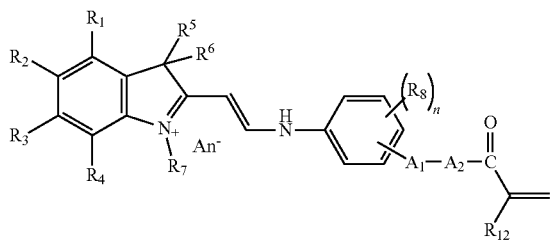

(wherein $R_1$ to $R_4$ each independently represent a hydrogen atom, a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms; $R_5$ and $R_6$ each independently represent a hydrogen atom, an alkyl group having 1 to 6 carbon atoms, an arylalkyl group having 7 to 13 carbon atoms, or a phenylalkyl group having 7 to 9 carbon atoms, which has an alkyl group having 1 to 6 carbon atoms, a nitro group, a halogeno group or a cyano group as a substituent of the phenyl group;

$R_7$ represents a hydrogen atom, an alkyl group having 1 to 6 carbon atoms, an arylalkyl group having 7 to 13 carbon atoms, an alkyl group having 1 to 6 carbon atoms, which has an alkoxy group having 1 to 6 carbon atoms, a hydroxy group, a carboxy group, a halogeno group, a cyano group, an amide group or an alkyloxycarbonyl group having 2 to 4 carbon atoms, as a substituent, or a phenylalkyl group having 7 to 9 carbon atoms, which has an alkoxy group having 1 to 6 carbon atoms, a halogeno group or an amide group, as a substituent of the phenyl group;

n pieces of $R_8$ each independently represent a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms; $R_{12}$ represents a hydrogen atom or a methyl group;

$A_1$ represents an alkylene group having 1 to 21 carbon atoms which has at least one group selected from —O—, —OCO—, —COO—, a vinylene group and an arylene group in the chain; an alkylene group having 1 to 21 carbon atoms which has at least one group selected from —O—, —OCO—, —COO—, a vinylene group and an arylene group in the chain, and also has a hydroxy group as a substituent; an alkylene group having 1 to 21 carbon atoms; or an alkylene group having 1 to 21 carbon atoms which has a hydroxy group as a substituent; $A_2$ represents —NH— or —O—.

An⁻ represents an anion containing an aryl group having an electron-withdrawing substituent, a sulfonyl group having an electron-withdrawing substituent, or a halogenated alkyl group.)

Advantageous Effects of Invention

When the compound or the polymer of the present invention is used as the coloring composition, even in the case of heating at 230° C. for 30 minutes, fading caused by heating is less, and high heat resistance effect is exerted. That is, the compound or the polymer of the present invention has superior heat resistance effect, and still more superior solvent resistance and weather resistance, as compared with the conventional coloring composition. Accordingly, the coloring composition of the present invention can be applied in various applications; and can be used in an application of color pixel formation such as a color filter used in a liquid crystal display (LCD) or a solid-state imaging element (CCD, CMOS, and the like), or in applications of printing ink, inkjet ink, paint, and the like; and particularly, it can be suitably used for the color filter of the liquid crystal display. Still more, the coloring composition of the present invention can also be used as a colored resin molded product by molding to a sheet, a film, a bottle, a cup, and the like, using a conventionally known molding method. Accordingly, it can be used also in applications of spectacles, contact lens, color contact lens, and the like and it can be used in similar applications also by making a multi-layered structure with a known resin. In addition, it can be used also in applications of, for example, an optical film, a hair coloring agent, a labeling material for a compound or a biomaterial, a material of an organic solar battery, and the like.

DESCRIPTION OF EMBODIMENTS

[Anion Containing the Aryl Group Having the Electron-Withdrawing Substituent, the Sulfonyl Group Having the Electron-Withdrawing Substituent, or the Halogenated Alkyl Group]

The anion containing the aryl group having the electron-withdrawing substituent, the sulfonyl group having the electron-withdrawing substituent, or the halogenated alkyl group, represented by An⁻ of the general formula (1) (hereinafter, it may be abbreviated as the anion of the present invention), includes, for example, a sulfonate anion, a nitrogen anion (N⁻), a quaternary boron anion, a nitrate ion, a phosphate ion, and the like, containing the aryl group having the electron-withdrawing substituent, the sulfonyl group having the electron-withdrawing substituent or the halogenated alkyl group. The sulfonate anion, the nitrogen anion and the quaternary boron anion are preferable, and the quaternary boron anion is more preferable.

The electron-withdrawing substituent in the aryl group having the electron-withdrawing substituent or the sulfonyl group having the electron-withdrawing substituent, in the anion of the present invention, includes, for example, a halogenated alkyl group having 1 to 3 carbon atoms a halogeno group, a nitro group, and the like, and among them, a halogenated alkyl group having 1 to 3 carbon atoms, and a halogeno group are preferable, and a halogeno group is particularly preferable.

The halogenated alkyl group having 1 to 3 carbon atoms, as the electron-withdrawing substituent, includes, for example, a chloroalkyl group such as a chloromethyl group, a trichloromethyl group, a 2-chloroethyl group, a 2,2,2-trichloroethyl group, a 2-chloropropyl group, a 3-chloropropyl group and a 2-chloro-2-propyl group; a bromoalkyl group such as a bromomethyl group, a tribromomethyl group, a 2-bromoethyl group, a 2,2,2-tribromoethyl group, a 2-bromopropyl group, a 3-bromopropyl group and a 2-bromo-2-propyl group; an iodoalkyl group such as an iodomethyl group, a triiodomethyl group, a 2-iodoethyl group, a 2,2,2-triiodoethyl group, a 2-iodopropyl group, a 3-iodopropyl group and a 2-iodo-2-propyl group; a fluoroalkyl group such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group and a heptafluoropropyl group. Among them, a fluoroalkyl group is preferable, and a trifluoromethyl group is particularly preferable.

The halogeno group as the electron-withdrawing substituent includes a fluoro group, a chloro group, a bromo group and an iodo group, and a fluoro group is preferable.

As the electron-withdrawing substituent in the aryl group having the electron-withdrawing substituent in the anion of the present invention, among the above-described specific examples, the one having strong electron-withdrawing force is preferable; and a trifluoromethyl group, a fluoro group and a nitro group are preferable, and a fluoro group and a nitro group are more preferable.

As the electron-withdrawing substituent in the sulfonyl group having the electron-withdrawing substituent in the anion of the present invention, among the above-described specific examples, a trifluoromethyl group, a pentafluoroethyl group, a heptafluoropropyl group and a fluoro group are preferable.

The aryl group in the aryl group having the electron-withdrawing substituent in the anion of the present invention includes, for example, a phenyl group, a naphthyl group, and the like, and a phenyl group is preferable.

Specific examples of the aryl group having the electron-withdrawing substituent, in the anion of the present invention, include, for example, those represented by the following general formulae (11) and (12).

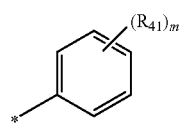

(11)

(wherein m represents an integer of 1 to 5; m pieces of $R_{41}$ each independently represent a halogenated alkyl group having 1 to 3 carbon atoms, a halogen atom or a nitro group; * represents an atomic bonding.)

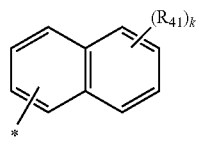

(12)

(wherein, k represents an integer of 1 to 7; $R_{41}$ and * are the same as described above; k pieces of $R_{41}$ may be the same or different.)

As for m, in the case where $R_{41}$ is a halogen atom, 2 to 5 is preferable, and 3 to 5 is more preferable, and 5 is still more preferable. In the case where $R_{41}$ is a nitro group, 1 to 3 is preferable, and 1 is more preferable. In the case were $R_{41}$ is a halogenated alkyl group, 1 to 5 is preferable.

As for k, in the case where $R_{41}$ is a halogen atom, 2 to 7 is preferable. In the case where $R_{41}$ is a nitro group, 1 to 3 is preferable, and 1 is more preferable. In the case where $R_{41}$ is a halogenated alkyl group, 1 to 7 is preferable.

The halogenated alkyl group having 1 to 3 carbon atoms, represented by $R_{41}$ in the general formula (11) and the general formula (12), includes the same one as the halogenated alkyl group having 1 to 3 carbon atoms in the electron-withdrawing substituent in the anion of the present invention, and the preferable ones are also the same.

The halogen atom in the general formula (11) and the general formula (12) includes a fluorine atom, a chlorine atom, a bromine atom, an iodine atom, and the like, and among them, a fluorine atom is preferable.

Preferable specific examples of $R_{41}$ in the general formula (11) and the general formula (12) are the same as the preferable ones of the electron-withdrawing substituent in the anion of the present invention.

The group represented by the general formula (11) specifically includes, for example, a trifluoromethylphenyl group, a di(trifluoromethyl)phenyl group, a tri(trifluoromethyl)phenyl group, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a periodophenyl group, a nitrophenyl group, a dinitrophenyl group, a trinitrophenyl group, and the like. A difluorophenyl group, a trifluorophenyl group, a perfluorophenyl group, and the like, are preferable, and a perfluorophenyl group is more preferable.

The group represented by the general formula (12) specifically includes, for example, a trifluoromethylnaphthyl group, a di(trifluoromethyl)naphthyl group, a tri(trifluoromethyl)naphthyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthyl group, a perbromonaphthyl group, a monoiodonaphthyl group, a diiodonaphthyl group, a triiodonaphthyl group, a periodonaphthyl group, a nitronaphthyl group, a dinitronaphthyl group, a trinitronaphthyl group, and the like.

As the aryl group having the electron-withdrawing substituent in the anion of the present invention, among the above-described specific examples, the group represented by the general formula (11) is preferable, and specifically, a trifluoromethylphenyl group, a nitrophenyl group, a dinitrophenyl group, a trinitrophenyl group, a monofluorophenyl group, a difluorophenyl group, a trifluorophenyl group and a perfluorophenyl group are preferable, and a difluorophenyl group, a trifluorophenyl group, a nitrophenyl group and a perfluorophenyl group are more preferable. A nitrophenyl group and a perfluorophenyl group are still more preferable, and a perfluorophenyl group is particularly preferable.

The sulfonyl group having the electron-withdrawing substituent in the anion of the present invention includes, for example, $-SO_2-CF_3$, $-SO_2-C_2F_5$, $-SO_2-C_3F_7$, $-SO_2-F$, $-SO_2-Cl$, $-SO_2-Br$, $-SO_2-I$, and the like.

The halogenated alkyl group in the anion of the present invention includes a halogenated alkyl group having 1 to 3 carbon atoms, for example, a trifluoromethyl group, a pentafluoroethyl group, a heptafluoropropyl group, a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, and the like, and a trifluoromethyl group, a pentafluoroethyl group, a heptafluoropropyl group, and the like, are preferable.

The anion containing the aryl group having the electron-withdrawing substituent, the sulfonyl group having the electron-withdrawing substituent, or the halogenated alkyl group, pertaining to the present invention, specifically includes, for example, those represented by the following general formulae (13) to (18).

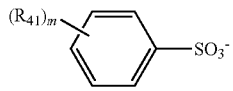
(13)

(wherein $R_{41}$ and m are the same as described above; m pieces of $R_{41}$ may be the same or different.)

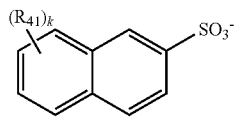
(14)

(wherein $R_{41}$ and k are the same as described above; k pieces of $R_{41}$ may be the same or different.)

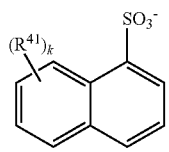
(15)

(wherein $R_{41}$ and k are the same as described above; k pieces of $R_{41}$ may be the same or different.)

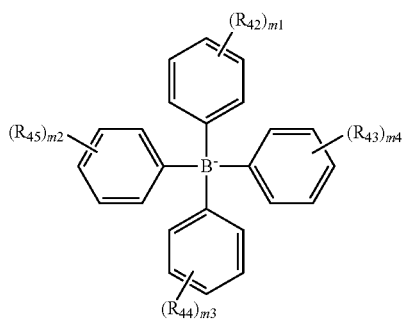
(16)

(wherein $R_{42}$ to $R_{45}$ each independently represent a halogenated alkyl group having 1 to 3 carbon atoms, a halogen atom or a nitro group; $m_1$ to $m_4$ each independently represent an integer of 1 to 5; $m_1$ pieces of $R_{42}$ may be the same or different; $m_2$ pieces of $R_{43}$, $m_3$ pieces of $R_{44}$, and $m_4$ pieces of $R_{45}$ may also be the same or different.)

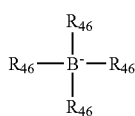
(17)

(wherein $R_{46}$ each independently represent a halogenated alkyl group having 1 to 3 carbon atoms, or a halogen atom, and at least one of four $R_{46}$ represents a halogenated alkyl group having 1 to 3 carbon atoms.)

(18)

(wherein $R_{47}$ and $R_{48}$ each independently represent a halogenated alkyl group having 1 to 3 carbon atoms, or a halogen atom, and $R_{47}$ together with $R_{48}$ may form a halogenated alkylene group having 2 to 3 carbon atoms.)

Combinations of $R_{41}$ and m in the general formula (13) include, for example, those described in the following table. It should be noted that the m pieces of $R_{41}$ are those each independent, however, the case where they are the same is preferable.

| $R_{41}$ | m |
|---|---|
| trifluoromethyl group (—CF$_3$) | 1 to 3 |
| pentafluoroethyl group (—C$_2$F$_5$) | 1 to 3 |
| heptafluoropropyl group (—C$_3$F$_7$) | 1 to 3 |
| fluorine atom | 1 to 5 |
| chlorine atom | 1 to 5 |
| bromine atom | 1 to 5 |
| iodine atom | 1 to 5 |
| nitro group | 1 to 3 |

Preferable specific examples of the anion represented by the general formula (13) include, for example, the following ones.

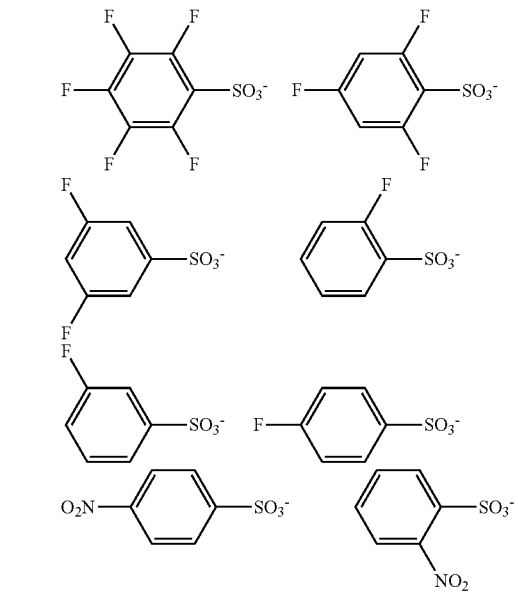

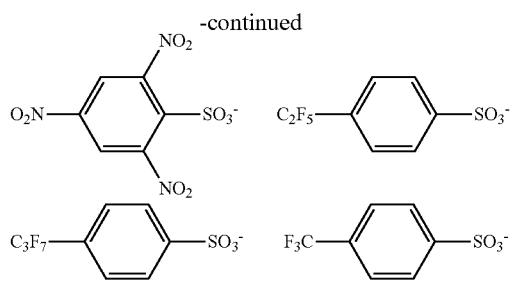

Combinations of $R_{41}$ and m in the general formulae (14) and (15) include, for example, those described in the following table. It should be noted that the m pieces of $R_{41}$ are each independent, however, the case where they are the same is preferable.

| $R_{41}$ | m |
|---|---|
| trifluoromethyl group (—CF$_3$) | 1 to 3 |
| pentafluoroethyl group (—C$_2$F$_5$) | 1 to 3 |
| heptafluoropropyl group (—C$_3$F$_7$) | 1 to 3 |
| nitro group | 1 to 4 |
| fluorine atom | 1 to 7 |
| chlorine atom | 1 to 7 |
| bromine atom | 1 to 7 |
| iodine atom | 1 to 7 |

Preferable specific examples of the anion represented by the general formulae (14) and (15) include, for example, the following ones.

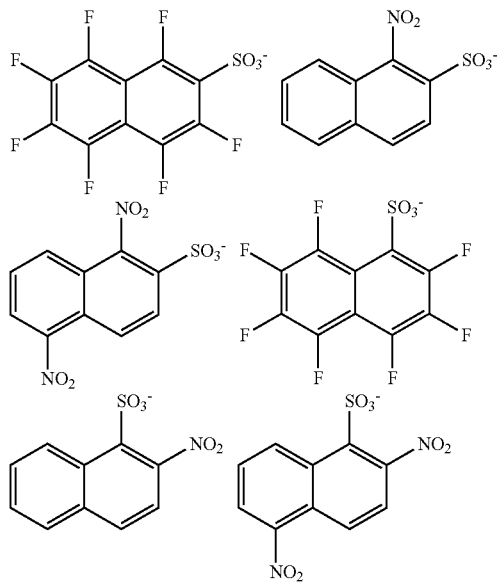

The halogenated alkyl group having 1 to 3 carbon atoms, in $R_{42}$ to $R_{45}$ of the general formula (16) includes the same one as the halogenated alkyl group in the anion of the present invention, and the preferable ones are also the same.

The halogen atom in $R_{42}$ to $R_{45}$ of the general formula (16) includes a fluorine atom, a chlorine atom, a bromine atom, an iodine atom, and the like, and among them, a fluorine atom is preferable.

Combinations of $R_{42}$ to $R_{45}$ and $m_1$ to $m_4$ in the general formula (16) include, for example, those described in the following table.

| $R_{42}$ | $m_1$ | $R_{43}$ | $m_2$ | $R_{44}$ | $m_3$ | $R_{45}$ | $m_4$ |
|---|---|---|---|---|---|---|---|
| —CF$_3$ | 1 to 3 | —CF$_3$ | 1 to 3 | —CF$_3$ | 1 to 3 | —CF$_3$ | 1 to 3 |
| —C$_2$F$_5$ | 1 to 3 | —C$_2$F$_5$ | 1 to 3 | —C$_2$F$_5$ | 1 to 3 | —C$_2$F$_5$ | 1 to 3 |
| —C$_3$F$_7$ | 1 to 3 | —C$_3$F$_7$ | 1 to 3 | —C$_3$F$_7$ | 1 to 3 | —C$_3$F$_7$ | 1 to 3 |
| nitro group | 1 to 3 | nitro group | 1 to 3 | nitro group | 1 to 3 | nitro group | 1 to 3 |
| fluorine | 1 to 5 | fluorine | 1 to 5 | fluorine | 1 to 5 | fluorine | 1 to 5 |
| chlorine | 1 to 5 | chlorine | 1 to 5 | chlorine | 1 to 5 | chlorine | 1 to 5 |
| bromine | 1 to 5 | bromine | 1 to 5 | bromine | 1 to 5 | bromine | 1 to 5 |
| iodine | 1 to 5 | iodine | 1 to 5 | iodine | 1 to 5 | iodine | 1 to 5 |
| nitro group | 1 to 3 | fluorine | 1 to 5 | fluorine | 1 to 5 | fluorine | 1 to 5 |
| nitro group | 1 to 3 | nitro group | 1 to 5 | fluorine | 1 to 5 | fluorine | 1 to 5 |
| nitro group | 1 to 3 | nitro group | 1 to 5 | nitro group | 1 to 5 | fluorine | 1 to 5 |

Preferable specific examples of the anion represented by the general formula (16) include, for example, the following formulae.

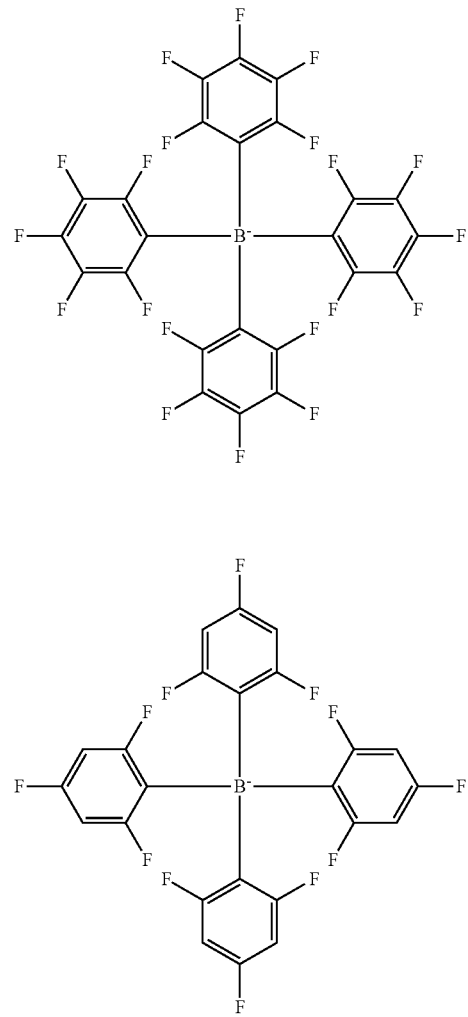

-continued
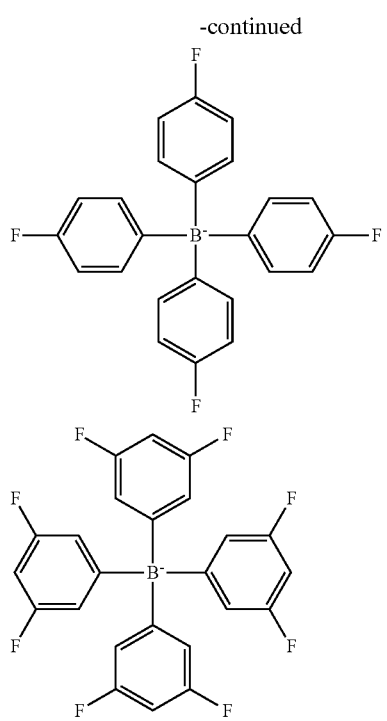
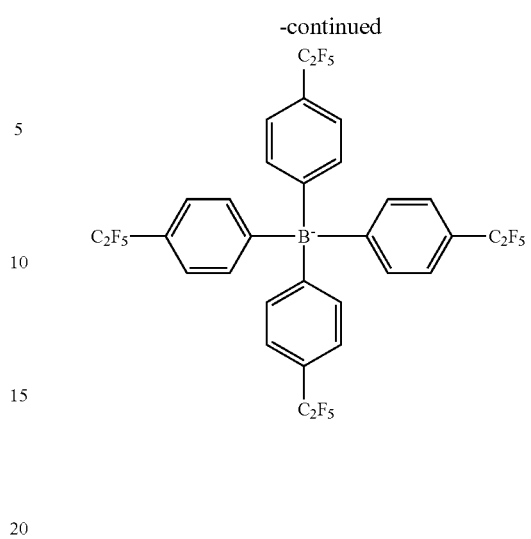
Among them, the following formulae are preferable.
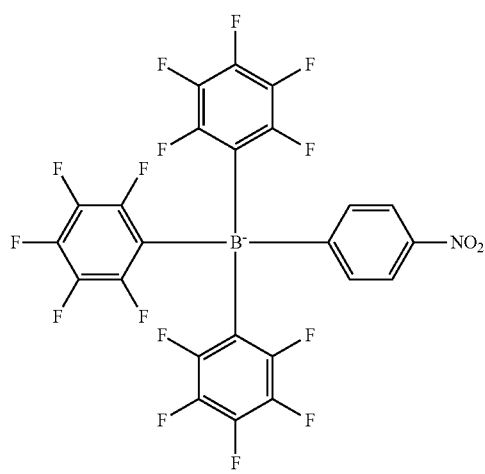
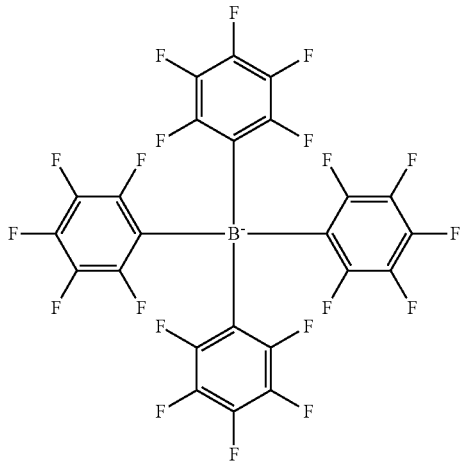
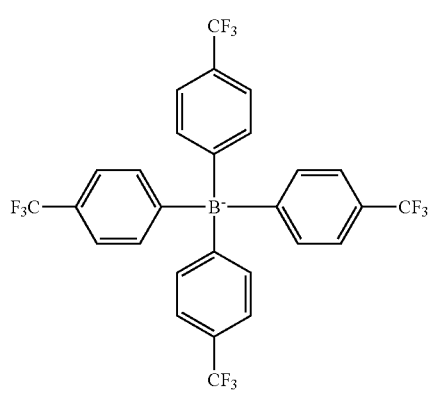
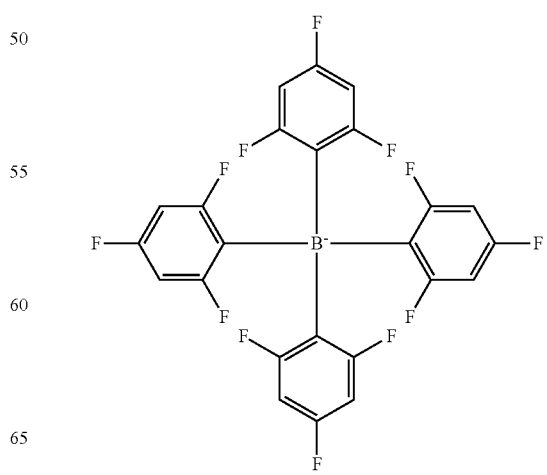

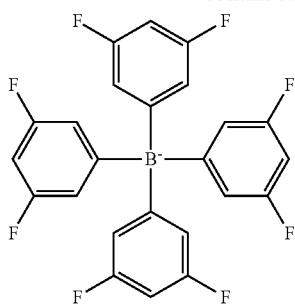

In addition, the following formula is particularly preferable.

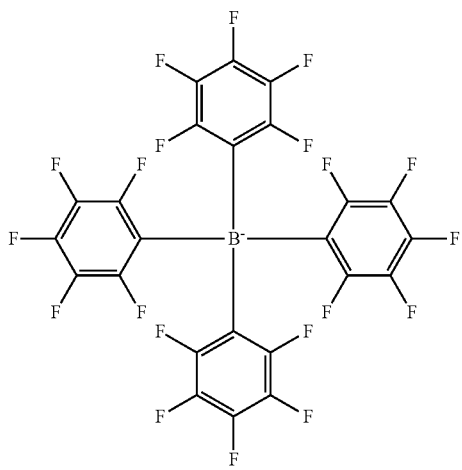 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F]

The halogenated alkyl group in $R_{46}$ of the general formula (17) includes the same one as the halogenated alkyl group in the anion of the present invention, and the preferable ones are also the same.

The halogen atom in $R_{46}$ of the general formula (17) includes a fluorine atom, a chlorine atom, a bromine atom, an iodine atom, and the like, and among them, a fluorine atom is preferable.

Preferable specific examples of the anion represented by the general formula (17) include, for example, $CF_3BF_3^-$, $C_2F_5BF_3^-$, $C_3F_7BF_3^-$, $(CF_3)_4B^-$, $(C_2F_5)_4B^-$, $(C_3F_7)_4B^-$, and the like.

The halogenated alkyl group in $R_{47}$ and $R_{48}$ of the general formula (18) includes the same one as the halogenated alkyl group in the anion of the present invention, and the preferable ones are also the same.

The halogen atom in $R_{47}$ and $R_{48}$ of the general formula (18) includes a fluorine atom, a chlorine atom, a bromine atom, an iodine atom, and the like, and among them, a fluorine atom is preferable.

The halogenated alkylene group having 2 to 3 carbon atoms formed by $R_{47}$ together with $R_{48}$ of the general formula (18) includes, for example, a tetrafluoroethylene group, a hexafluoropropylene group, and the like.

Preferable specific examples of the anion represented by the general formula (18) include, for example, the following formulae.

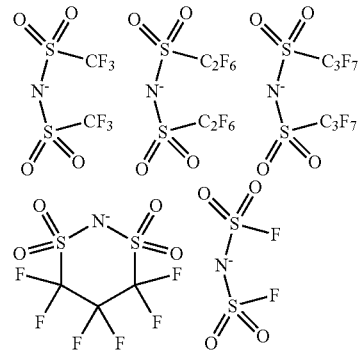

As the anion of the present invention, the one represented by the general formula (16), the general formula (17) or the general formula (18) is preferable, and the one represented by the general formula (16) is more preferable. Among the above-described specific examples, the following formula is particularly preferable.

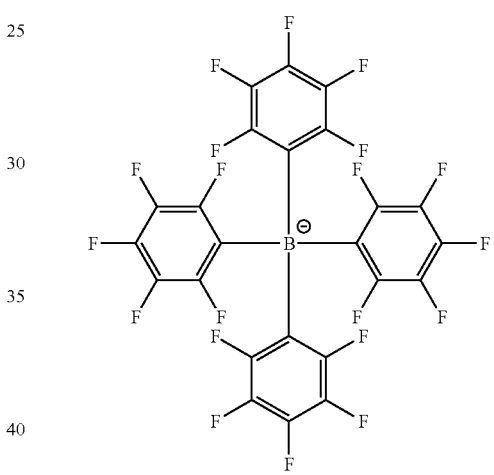

[Compound of the Present Invention]

The compound of the present invention is a compound represented by the general formula (1).

The alkyl group having 1 to 6 carbon atoms in $R_1$ to $R_4$ and $R_8$ of the general formula (1) may be the straight chained, branched, or cyclic one, and the straight chained one is preferable. Also, 1 to 3 carbon atoms are preferable. It includes specifically for example, a methyl group, an ethyl group, a n-propyl group, an isopropyl group, a n-butyl group, a 1-methylpropyl group, an isobutyl group, a sec-butyl group, a tert-butyl group, a pentyl group, a 1-ethylpropyl group, a 1-methylbutyl group, a cyclopentyl group, a hexyl group, a 1-methylpentyl group, a 1-ethylbutyl group, a cyclohexyl group, and the like, and among them, a methyl group, an ethyl group and a n-propyl group are preferable.

The alkoxy group having 1 to 6 carbon atoms in $R_1$ to $R_4$ and $R_8$ of the general formula (1) may be the straight chained, branched, or cyclic one, and the straight chained one is preferable. Also, 1 to 3 carbon atoms are preferable. It includes specifically, for example, a methoxy group, an ethoxy group, a propoxy group, a butoxy group, a t-butoxy group, a hexyloxy group, and the like, and a methoxy group, an ethoxy group, a propoxy group, and the like, are preferable.

The alkyloxycarbonyl group having 2 to 4 carbon atoms in $R_1$ to $R_4$ and $R_8$ of the general formula (1) may be the straight chained, branched, or cyclic one, and the straight chained one is preferable. It includes specifically, for example, a methyloxycarbonyl group, an ethyloxycarbonyl group, a propyloxycarbonyl group, and the like.

The alkylcarbonyloxy group having 2 to 4 carbon atoms in $R_1$ to $R_4$ and $R_8$ of the general formula (1) may be the straight chained, branched, or cyclic one, and the straight chained one is preferable. It includes specifically, for example, a methylcarbonyloxy group, an ethylcarbonyloxy group, a propylcarbonyloxy group, and the like.

As n of the general formula (1), 0 to 2 is preferable, and 0 is more preferable.

The arylcarbonyl group having 7 to 10 carbon atoms in $R_1$ to $R_4$ and $R_8$ in the general formula (1) includes, for example, a phenylcarbonyl group, a naphthylcarbonyl group, and the like, and a phenylcarbonyl group is preferable.

Preferable specific examples of $R_1$ to $R_4$ in the general formula (1) each independently include a hydrogen atom or an alkyl group having 1 to 6 carbon atoms. Among them, a hydrogen atom is preferable, and the case where all of them are hydrogen atoms is preferable.

Preferable specific examples of n pieces of $R_8$ in the general formula (1) each independently include an alkyl group having 1 to 6 carbon atoms, an alkoxy group having 1 to 6 carbon atoms, and the like. Among them, an alkoxy group having 1 to 6 carbon atoms, and the like, are preferable.

The alkyl group having 1 to 6 carbon atoms in $R_5$ and $R_6$ of the general formula (1) may be the straight chained, branched, or cyclic one, and the straight chained one is preferable. Also, 1 to 3 carbon atoms are preferable. It includes specifically, for example, a methyl group, an ethyl group, a n-propyl group, an isopropyl group, a butyl group, a 1-methylpropyl group, an isobutyl group, a sec-butyl group, a tert-butyl group, a pentyl group, a 1-ethylpropyl group, a 1-methylbutyl group, a cyclopentyl group, a hexyl group, a 1-methylpentyl group, a 1-ethylbutyl group, a cyclohexyl group, and the like, and among them, a methyl group, an ethyl group and a n-propyl group are preferable.

The arylalkyl group having 7 to 13 carbon atoms in $R_5$ and $R_6$ of the general formula (1) includes, for example, a benzyl group, a phenylethyl group, a phenylpropyl group, a naphthylmethyl group, a naphthylethyl group, a naphthylpropyl group, and the like, and a benzyl group is preferable.

The alkyl group having 1 to 6 carbon atoms, as a substituent of the phenyl group in $R_5$ and $R_6$ of the general formula (1), includes the same one as the alkyl group having 1 to 6 carbon atoms in $R_5$ of the general formula (1), and the preferable ones are also the same.

The halogeno group as a substituent of the phenyl group in $R_5$ and $R_6$ of the general formula (1) includes a fluoro group, a chloro group, a bromo group and an iodo group.

The phenylalkyl group of the phenylalkyl group having 7 to 9 carbon atoms which has a substituent, in $R_5$ and $R_6$ of the general formula (I), includes a benzyl group, a phenylethyl group, a phenylpropyl group, and the like, and a benzyl group is preferable. It should be noted that the above-described 7 to 9 carbon atoms does not include the number of carbon atoms of a substituent. In the present description, similarly hereafter, the number of carbon atoms of a group which has a substituent represents a number which does not include the number of carbon atoms of the substituent.

The phenylalkyl group having 7 to 9 carbon atoms which has a substituent, in $R_5$ and $R_6$ of the general formula (1), specifically includes, for example, a methylbenzyl group, an ethylbenzyl group, a propylbenzyl group, a nitrobenzyl group, a dinitrobenzyl group, a fluorobenzyl group, a chlorobenzyl group, a bromobenzyl group, an iodobenzyl group, a cyanobenzyl group, an amidebenzyl group, and the like.

Preferable specific examples of $R_5$ and $R_6$ in the general formula (1) each independently include a hydrogen atom and an alkyl group having 1 to 6 carbon atoms. Among them, a methyl group, an ethyl group and a propyl group are preferable, and the case where both of them are methyl groups is particularly preferable.

The alkyl group having 1 to 6 carbon atoms in $R_7$ of the general formula (1) includes the same one as the alkyl group having 1 to 6 carbon atoms in $R_5$ of the general formula (1), and the preferable ones are also the same.

The arylalkyl group having 7 to 13 carbon atoms in $R_7$ of the general formula (1) includes the same one as the arylalkyl group having 7 to 13 carbon atoms in $R_5$ and $R_6$ of the general formula (1), and the preferable ones are also the same.

The alkoxy group having 1 to 6 carbon atoms, as a substituent of the alkyl group having 1 to 6 carbon atoms in $R_7$ of the general formula (1), includes the same one as the alkoxy group having 1 to 6 carbon atoms in $R_1$ to $R_4$ and $R_8$ of the general formula (1), and the preferable ones are also the same.

The halogeno group, as a substituent of the alkyl group having 1 to 6 carbon atoms in $R_7$ of the general formula (1), includes a fluoro group, a chloro group, a bromo group and an iodo group.

The alkyloxycarbonyl group having 2 to 4 carbon atoms, as a substituent of the alkyl group having 1 to 6 carbon atoms in $R_7$ of the general formula (1), may be the straight chained, branched, or cyclic one, and the straight chained one is preferable. Specifically, for example, it includes a methyloxycarbonyl group, an ethyloxycarbonyl group, a propyloxycarbonyl group, and the like.

The alkyl group of the alkyl group having 1 to 6 carbon atoms, which has a substituent, in $R_7$ of the general formula (1), includes the same one as the alkyl group having 1 to 6 carbon atoms in $R_5$ of the general formula (1), and the preferable ones are also the same.

The alkyl group having 1 to 6, which has a substituent, in $R_7$ of the general formula (1), specifically includes, for example, a methoxymethyl group, an ethoxymethyl group, a propoxymethyl group, a methoxyethyl group, an ethoxyethyl group, a propoxyethyl group, a hydroxymethyl group, a hydroxyethyl group, a hydroxypropyl group, a carboxymethyl group, a carboxyethyl group, a carboxypropyl group, a fluoromethyl group, a fluoroethyl group, a fluoropropyl group, a chloromethyl group, a chloroethyl group, a chloropropyl group, a bromomethyl group, a bromoethyl group, a bromopropyl group, an iodomethyl group, an iodoethyl group, an iodopropyl group, a cyanomethyl group, a cyanoethyl group, a cyanopropyl group, an amidemethyl group, an amideethyl group, an amidepropyl group, a methyloxycarbonylmethyl group, a methyloxycarbonylethyl group, an ethyloxycarbonylmethyl group and an ethyloxycarbonylethyl group.

The alkoxy group having 1 to 6 carbon atoms, as a substituent of the phenylalkyl group having 7 to 9 carbon atoms in $R_7$ of the general formula (1), includes the same one as the alkoxy group having 1 to 6 carbon atoms in $R_1$ to $R_4$ and $R_8$ of the general formula (1), and the preferable ones are also the same.

The halogeno group as a substituent of the phenylalkyl group having 7 to 9 carbon atoms in $R_7$ of the general formula (1) includes a fluoro group, a chloro group, a bromo group and an iodo group.

The phenylalkyl group of the phenylalkyl group having 7 to 9 carbon atoms in $R_7$ of the general formula (1) includes a benzyl group, a phenylethyl group, a phenylpropyl group, and the like, and a benzyl group is preferable.

The phenylalkyl group having 7 to 9 carbon atoms, which has a substituent, in $R_7$ of the general formula (1), includes a methoxybenzyl group, an ethoxybenzyl group, a propyloxybenzyl group, a fluorobenzyl group, a chlorobenzyl group, a bromobenzyl group, an iodobenzyl group, an amidebenzyl group, and the like.

As $R_7$ of the general formula (1), an alkyl group having 1 to 6 carbon atoms is preferable, and among them, a methyl group, an ethyl group and an n-propyl group are preferable.

The arylene group in the chain of the alkylene group having 1 to 21 carbon atoms in $A_1$ of the general formula (1) includes a phenylene group and a naphthylene group, and a phenylene group is preferable.

The alkylene group having 1 to 21 carbon atoms in "an alkylene group having 1 to 21 carbon atoms which has at least one group selected from —O—, —OCO—, —COO—, a vinylene group and an arylene group in the chain", "an alkylene group having 1 to 21 carbon atoms which has at least one group selected from —O—, —OCO—, —COO—, a vinylene group and an arylene group in the chain, and also has a hydroxy group as a substituent", "an alkylene group having 1 to 21 carbon atoms which has a hydroxy group as a substituent" and "an alkylene group having 1 to 21 carbon atoms", in $A_1$ of the general formula (1), may be the straight chained or branched one, wherein 1 to 12 carbon atoms is preferable, and 1 to 6 carbon atoms is more preferable, and 1 to 3 carbon atoms is further preferable. It includes specifically, for example, a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group, a n-heptylene group, a n-octylene group, a n-nonylene group, a n-decylene group, a n-undecylene group, a n-dodecylene group, a n-tridecylene group, a n-tetradecylene group, a n-pentadecylene group, a n-hexadecylene group, a n-heptadecylene group, a n-octadecylene group, a n-nonadecylene group, a n-aralkylene group, a n-eicosylene group, a cyclopentylene group, a cyclohexylene group, a cycloheptylene group, and the like, and a methylene group, an ethylene group, a propylene group, a butylene group, a pentylene group, a hexylene group, and the like, are preferable. A methylene group, an ethylene group and a propylene group are more preferable, and an ethylene group is particularly preferable.

"An alkylene group having 1 to 21 carbon atoms which has at least one group selected from —O—, —OCO—, —COO—, a vinylene group and an arylene group in the chain", in $A_1$ of the general formula (1), includes, for example, the group represented by the following general formulae (6-1) to (6-6), and the like.

$$—R_{51}—X_1—R_{51}— \quad (6\text{-}1)$$

(wherein two pieces of $R_{51}$ each independently represent an alkylene group baying 1 to 10 carbon atoms; $X_1$ represents —O—, —OCO—, COO—, a vinylene group, or an arylene group.)

$$—R_{51}—X_1—R_{51}—X_1—R_{51}— \quad (6\text{-}2)$$

(wherein three pieces of $R_{51}$ each independently represent the same one as described above; and $X_1$ is the same as described above.)

$$—R_{51}—(C_2H_4O)_{p7}—R_{51}— \quad (6\text{-}3)$$

(wherein two pieces of $R_{51}$ each independently represent the same one as described above; and p7 represents an integer of 1 to 9.)

$$—R_{51}—(CH_2CH(CH_3)O)_{p9}—R_{51}— \quad (6\text{-}4)$$

(wherein two pieces of $R_{51}$ each independently represent the same one as described above; and p9 represents an integer of 1 to 9.)

$$—X_2—R_{53}— \quad (6\text{-}5)$$

(wherein $X_2$ represents —O—, —OCO—, or —COO— group; and $R_{53}$ represents an alkylene group having 1 to 10 carbon atoms.)

$$—CH=CH—COO—R_{54}— \quad (6\text{-}6)$$

(wherein $R_{54}$ represents an alkylene group having 1 to 10 carbon atoms.)

As the alkylene group having 1 to 10 carbon atoms in $R_{51}$ of the general formula (6-1), the one having 1 to 6 carbon atoms is preferable, and the one having 1 to 3 carbon atoms is more preferable. It includes specifically, for example, a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group, a n-heptylene group, a n-octylene group, a n-nonylene group, a n-decylene group, a cyclopentylene group, a cyclohexylene group, a cycloheptylene group, and the like, and a methylene group, an ethylene group and a propylene group are more preferable, and an ethylene group is particularly preferable.

The group represented by the general formula (6-1) specifically includes, for example, the following general formulae (wherein $X_{11}$ represents —O—, —OCO—, COO—, a vinylene group, or an arylene group).

$$—CH_2—X_{11}—CH_2—$$

$$—CH_2—X_{11}—C_2H_4—$$

$$—CH_2—X_{11}—C_3H_6—$$

$$—CH_2—X_{11}—C_4H_8—$$

$$—CH_2—X_{11}—C_5H_{10}—$$

$$—CH_2—X_{11}—C_6H_{12}—$$

$$—C_2H_4—X_{11}—CH_2—$$

$$—C_2H_4—X_{11}—C_2H_4—$$

$$—C_2H_4—X_{11}—C_3H_6—$$

$$—C_2H_4—X_{11}—C_4H_8—$$

$$—C_2H_4—X_{11}—C_5H_{10}—$$

$$—C_2H_4—X_{11}—C_6H_{12}—$$

$$—C_3H_6—X_{11}—CH_2—$$

$$—C_3H_6—X_{11}—C_2H_4—$$

$$—C_3H_6—X_{11}—C_3H_6—$$

—$C_3H_6$—$X_{11}$—$C_4H_8$—

—$C_3H_6$—$X_{11}$—$C_5H_{10}$—

—$C_3H_6$—$X_{11}$—$C_6H_{12}$—

—$CH_2$—$X_{11}$—$C_6H_{10}$—

—$C_2H_4$—$X_{11}$—$C_6H_{10}$—

—$C_3H_6$—$X_{11}$—$C_6H_{10}$—

As $X_{11}$ in the group represented by the general formula (6-1), —OCO—, COO—, and the like, are preferable, and —OCO— is more preferable.

More specific preferable examples of the group represented by the general formula (6-1) include those of the following formulae.

—$CH_2$—OCO—$CH_2$—

—$CH_2$—OCO—$C_2H_4$—

—$CH_2$—OCO—$C_3H_6$—

—$CH_2$—OCO—$C_4H_8$—

—$CH_2$—OCO—$C_5H_{10}$—

—$CH_2$—OCO—$C_6H_{12}$—

—$C_2H_4$—OCO—$CH_2$—

—$C_2H_4$—OCO—$C_2H_4$—

—$C_2H_4$—OCO—$C_3H_6$—

—$C_2H_4$—OCO—$C_4H_8$—

—$C_2H_4$OCO—$C_5H_{10}$—

—$C_2H_4$OCO—$C_6H_{12}$—

—$C_3H_6$OCO—$CH_2$—

—$C_3H_6$OCO—$C_2H_4$—

—$C_3H_6$OCO—$C_3H_6$—

—$C_3H_6$—OCO—$C_4H_8$—

—$C_3H_6$—OCO—$C_5H_{10}$—

—$C_3H_6$—OCO—$C_6H_{12}$—

—$CH_2$—OCO—$C_6H_{10}$—

—$C_2H_4$—OCO—$C_6H_{10}$—

—$C_3H_6$—OCO—$C_6H_{10}$—

Preferable specific examples of the group represented by the general formula (6-2) include, for example, the following general formulae (wherein $X_{11}$ each independently represent —O—, —OCO—, COO—, a vinylene group, or a phenylene group).

—$CH_2$—$X_{11}$—$C_2H_4$—$X_{11}$—$CH_2$—

—$CH_2X_{11}$—$C_2H_4$—$X_{11}$—$C_2H_4$—

—$C_2H_4$—$X_{11}$—$C_2H_4$—$X_{11}$—$CH_2$—

—$C_2H_4$—$X_{11}$—$C_2H_4$—$X_{11}$—$C_2H_4$—

—$C_2H_4$—$X_{11}$—$C_2H_4$—$X_{11}$—$C_3H_6$—

—$C_2H_4$—$X_{11}$—$C_2H_4$—$X_{11}$—$C_4H_8$—

—$C_2H_4$—$X_{11}$—$C_2H_4$—$X_{11}$—$C_5H_{10}$—

—$C_2H_4$—$X_{11}$—$C_2H_4$—$X_{11}$—$C_6H_{12}$—

—$C_3H_6$—$X_{11}$—$C_2H_4$—$X_{11}$—$CH_2$—

—$C_3H_6$—$X_{11}$—$C_2H_4$—$X_{11}$—$C_2H_4$—

—$C_3H_6$—$X_{11}$—$C_2H_4$—$X_{11}$—$C_3H_6$—

—$C_3H_6$—$X_{11}$—$C_2H_4$—$X_{11}$—$C_4H_8$—

—$C_3H_6$—$X_{11}$—$C_2H_4$—$X_{11}$—$C_5H_{10}$—

—$C_3H_6$—$X_{11}$—$C_2H_4$—$X_{11}$—$C_6H_{12}$—

—$C_4H_8$—$X_{11}$—$C_2H_4$—$X_{11}$—$CH_2$—

—$C_4H_8$—$X_{11}$—$C_2H_4$—$X_{11}$—$C_2H_4$—

—$C_4H_8$—$X_{11}$—$C_2H_4$—$X_{11}$—$C_3H_6$—

—$C_4H_8$—$X_{11}$—$C_2H_4$—$X_{11}$—$C_4H_8$—

—$C_4H_8$—$X_{11}$—$C_2H_4$—$X_{11}$—$C_5H_{10}$—

—$C_4H_8$—$X_{11}$—$C_2H_4$—$X_{11}$—$C_6H_{12}$—

—$C_5H_{10}$—$X_{11}$—$C_2H_4$—$X_{11}$—$CH_2$—

—$C_5H_{10}$—$X_{11}$—$C_2H_4$—$X_{11}$—$C_2H_4$—

—$C_5H_{10}$—$X_{11}$—$C_2H_4$—$X_{11}$—$C_3H_6$—

—$C_5H_{10}$—$X_{11}$—$C_2H_4$—$X_{11}$—$C_4H_8$—

—$C_5H_{10}$—$X_{11}$—$C_2H_4$—$X_{11}$—$C_5H_{10}$—

—$C_5H_{10}$—$X_{11}$—$C_2H_4$—$X_{11}$—$C_6H_{12}$—

—$C_6H_{12}$—$X_{11}$—$C_2H_4$—$X_{11}$—$CH_2$—

—$C_6H_{12}$—$X_{11}$—$C_2H_4$—$X_{11}$—$C_2H_4$—

—$C_6H_{12}$—$X_{11}$—$C_2H_4$—$X_{11}$—$C_3H_6$—

—$C_6H_{12}$—$X_{11}$—$C_2H_4$—$X_{11}$—$C_4H_8$—

—$C_6H_{12}$—$X_{11}$—$C_2H_4$—$X_{11}$—$C_5H_{10}$—

—$C_6H_{12}$—$X_{11}$—$C_2H_4$—$X_{11}$—$C_6H_{12}$—

—$CH_2$—$X_{11}$—$C_3H_6$—$X_{11}$—$CH_2$—

—$C_2H_4$—$X_{11}$—$C_3H_6$—$X_{11}$—$C_2H_4$—

—$C_2H_4$—$X_{11}$—$C_3H_6$—$X_{11}$—$C_3H_6$—

—$C_2H_4$—$X_{11}$—$C_3H_6$—$X_{11}$—$C_4H_8$—

—$C_2H_4$—$X_{11}$—$C_3H_6$—$X_{11}$—$C_5H_{10}$—

—$C_2H_4$—$X_{11}$—$C_3H_6$—$X_{11}$—$C_6H_{12}$—

—$C_3H_6$—$X_{11}$—$C_3H_6$—$X_{11}$—$C_2H_4$—

—$C_3H_6$—$X_{11}$—$C_3H_6$—$X_{11}$—$C_3H_6$—

—$C_3H_6$—$X_{11}$—$C_3H_6$—$X_{11}$—$C_4H_8$—

—$C_3H_6$—$X_{11}$—$C_3H_6$—$X_{11}$—$C_5H_{10}$—

—$C_3H_6$—$X_{11}$—$C_3H_6$—$X_{11}$—$C_6H_{12}$—

—$C_4H_8$—$X_{11}$—$C_3H_6$—$X_{11}$—$C_4H_8$—

—$C_5H_{10}$—$X_{11}$—$C_3H_6$—$X_{11}$—$C_5H_{10}$—

—$C_6H_{12}$—$X_{11}$—$C_3H_6$—$X_{11}$—$C_6H_{12}$—

—$C_2H_4$—$X_{11}$—$CH_2$—$X_{11}$—$C_2H_4$—

—$C_2H_4$—$X_{11}$—$C_4H_8$—$X_{11}$—$C_2H_4$—

—$C_2H_4$—$X_{11}$—$C_5H_{10}$—$X_{11}$—$C_2H_4$—

—$C_2H_4$—$X_{11}$—$C_6H_{12}$—$X_{11}$—$C_2H_4$—

—$C_2H_4$—$X_{11}$—$C_6H_{10}$—$X_{11}$—$C_2H_4$—

As $X_{11}$ in the group represented by the general formula (6-2), —OCO—, COO—, and the like, are preferable.

More specific preferable examples of the group represented by the general formula (6-2) include the following formulae.

—$CH_2$—OCO—$C_2H_4$—COO—$C_2H_4$—

—$CH_2$—OCO—$C_3H_6$—COO—$C_3H_6$—

—$C_4H_8$—OCO—$C_2H_4$—COO—$CH_2$—

—$C_4H_8$—OCO—$C_2H_4$—COO—$C_2H_4$—

—$C_4H_8$—OCO—$C_2H_4$—COO—$C_3H_6$—

—$C_4H_8$—OCO—$C_2H_4$—COO—$C_4H_8$—

—$C_4H_8$—OCO—$C_2H_4$—COO—$C_5H_{10}$—

—$C_4H_8$—OCO—$C_2H_4$—COO—$C_6H_{12}$—

—$C_5H_{10}$—OCO—$C_2H_4$—COO—$CH_2$—

—$C_5H_{10}$—OCO—$C_2H_4$—COO—$C_2H_4$—

—$C_5H_{10}$—OCO—$C_2H_4$—COO—$C_3H_6$—

—$C_5H_{10}$—OCO—$C_2H_4$—COO—$C_4H_8$—

—$C_5H_{10}$—OCO—$C_2H_4$—COO—$C_5H_{10}$—

—$C_5H_{10}$—OCO—$C_2H_4$—COO—$C_6H_{12}$—

—$C_6H_{12}$—OCO—$C_2H_4$—COO—$CH_2$—

—$C_6H_{12}$—OCO—$C_2H_4$—COO—$C_2H_4$—

—$C_6H_{12}$—OCO—$C_2H_4$—COO—$C_3H_6$—

—$C_6H_{12}$—OCO—$C_2H_4$—COO—$C_4H_8$—

—$C_6H_{12}$—OCO—$C_2H_4$—COO—$C_5H_{10}$—

—$C_6H_{12}$—OCO—$C_2H_4$—COO—$C_6H_{12}$—

—$CH_2$—OCO—$C_3H_6$—COO—$CH_2$—

—$C_2H_4$—OCO—$C_3H_6$—COO—$C_2H_4$—

—$C_2H_4$—OCO—$C_3H_6$—COO—$C_3H_6$—

—$C_2H_4$—OCO—$C_3H_6$—COO—$C_4H_8$—

—$C_2H_4$—OCO—$C_3H_6$—COO—$C_5H_{10}$—

—$C_2H_4$—OCO—$C_3H_6$—COO—$C_6H_{12}$—

—$C_3H_6$—OCO—$C_3H_6$—COO—$C_2H_4$—

—$C_3H_6$—OCO—$C_3H_6$—COO—$C_3H_6$—

—$C_3H_6$—OCO—$C_3H_6$—COO—$C_4H_8$—

—$C_3H_6$—OCO—$C_3H_6$—COO—$C_5H_{10}$—

—$C_3H_6$—OCO—$C_3H_6$—COO—$C_6H_{12}$—

—$C_4H_8$—OCO—$C_3H_6$—COO—$C_4H_8$—

—$C_5H_{10}$—OCO—$C_3H_6$—COO—$C_5H_{10}$—

—$C_6H_{12}$—OCO—$C_3H_6$—COO—$C_6H_{12}$—

—$C_2H_4$—OCO—$CH_2$—COO—$C_2H_4$—

—$C_2H_4$—OCO—$C_4H_8$—COO—$C_2H_4$—

—$C_2H_4$—OCO—$C_5H_{10}$—COO—$C_2H_4$—

—$C_2H_4$—OCO—$C_6H_{12}$—COO—$C_2H_4$—

—$C_2H_4$—OCO—$C_6H_{10}$—COO—$C_2H_4$—

Preferable specific examples of the group represented by the general formula (6-3) include, for example, the following general formulae (wherein p7 is the same as described above).

—$CH_2$—$(C_2H_4O)_{p7}$—$CH_2$—

—$CH_2$—$(C_2H_4O)_{p7}$—$C_2H_4$—

—$CH_2$—$(C_2H_4O)_{p7}$—$C_3H_6$—

—$C_2H_4$—$(C_2H_4O)_{p7}$—$CH_3$—

—$C_2H_4$—$(C_2H_4O)_{p7}$—$C_2H_4$—

—$C_2H_4$—$(C_2H_4O)_{p7}$—$C_3H_6$—

—$C_2H_4$—$(C_2H_4O)_{p7}$—$C_4H_8$—

—$C_2H_4$—$(C_2H_4O)_{p7}$—$C_5H_{10}$—

—$C_2H_4$—$(C_2H_4O)_{p7}$—$C_6H_{12}$—

—$C_2H_4$—$(C_2H_4O)_{p7}$—$CH_2$—

—$C_2H_4$—$(C_2H_4O)_{p7}$—$C_2H_4$—

—$C_2H_4$—$(C_2H_4O)_{p7}$—$C_3H_6$—

—$C_3H_6$—$(C_2H_4O)_{p7}$—$CH_2$—

—$C_3H_6$—$(C_2H_4O)_{p7}$—$C_2H_4$—

—$C_3H_6$—$(C_2H_4O)_{p7}$—$C_3H_6$—

Preferable specific examples of the group represented by the general formula (6-4) include, for example, the following general formulae (wherein p9 is the same as described above).

—$CH_2$—$(CH_2CH(CH_3)O)_{p9}$—$CH_2$—

—$CH_2$—$(CH_2CH(CH_3)O)_{p9}$—$C_2H_4$—

—$CH_2$—$(CH_2CH(CH_3)O)_{p9}$—$C_3H_6$—

—C$_2$H$_4$—(CH$_2$CH(CH$_3$)O)$_{p9}$—CH$_2$—

—C$_2$H$_4$—(CH$_2$CH(CH$_3$)O)$_{p9}$—C$_2$H$_4$—

—C$_2$H$_4$—(CH$_2$CH(CH$_3$)O)$_{p9}$—C$_3$H$_6$—

—C$_2$H$_4$—(CH$_2$CH(CH$_3$)O)$_{p9}$—C$_4$H$_8$—

—C$_2$H$_4$—(CH$_2$CH(CH$_3$)O)$_{p9}$—C$_5$H$_{10}$—

—C$_2$H$_4$—(CH$_2$CH(CH$_3$)O)$_{p9}$—C$_6$H$_{12}$—

—C$_2$H$_4$—(CH$_2$CH(CH$_3$)O)$_{p9}$—CH$_2$—

—C$_2$H$_4$—(CH$_2$CH(CH$_3$)O)$_{p9}$—C$_2$H$_4$—

—C$_2$H$_4$—(CH$_2$CH(CH$_3$)O)$_{p9}$—C$_3$H$_6$—

—C$_3$H$_6$—(CH$_2$CH(CH$_3$)O)$_{p9}$—CH$_2$—

—C$_3$H$_6$—(CH$_2$CH(CH$_3$)O)$_{p9}$—C$_2$H$_4$—

—C$_3$H$_6$—(CH$_2$CH(CH$_3$)O)$_{p9}$—C$_3$H$_6$—

Specific examples and the preferable ones of the alkylene group having 1 to 10 carbon atoms in R$_{53}$ of the general formula (6-5) include the same ones as R$_{51}$ of the general formula (6-1).

As X$_2$ of the general formula (6-5), —COO— group is preferable.

Preferable specific examples of the group represented by the general formula (6-5) include, for example, the following formulae.

—COO—CH$_2$—, —COO—C$_2$H$_4$—, —COO—C$_3$H$_6$—,

—COO—C$_4$H$_8$—, —COO—C$_5$H$_{10}$—, —COO—C$_6$H$_{12}$—,

—O—CH$_2$—, —O—C$_2$H$_4$—, —O—C$_3$H$_6$—, —O—C$_4$H$_8$—, —O—C$_5$H$_{10}$—, —O—C$_6$H$_{12}$—,

—OCO—CH$_2$—, —OCO—C$_2$H$_4$—, —OCO—C$_3$H$_6$—, —OCO—C$_4$H$_8$—, —OCO—C$_5$H$_{10}$—, —OCO—C$_6$H$_{12}$—

Among them, the following formulae are preferable.

—COO—CH$_2$—, —COO—C$_2$H$_4$—, —COO—C$_3$H$_6$—, —COO—C$_4$H$_8$—, —COO—C$_5$H$_{10}$—, —COO—C$_6$H$_{12}$—

Still more, the following formulae are more preferable.

—COO—CH$_2$—, —COO—C$_2$H$_4$—, —COO—C$_3$H$_6$—

Specific examples and the preferable ones of the alkylene group having 1 to 10 carbon atoms in R$_{54}$ of the general formula (6-6) include the same ones as R$_{51}$ of the general formula (6-1).

Preferable specific examples of the group represented by the general formula (6-6) include, for example, the following formulae.

—CH=CH—COO—CH$_2$—, —CH=CH—COO—C$_2$H$_4$—,

—CH=CH—COO—C$_3$H$_6$—, —CH=CH—COO—C$_4$H$_8$—,

—CH=CH—COO—C$_5$H$_{10}$—, —CH=CH—COO—C$_6$H$_{12}$—

Among them, the following formulae are preferable.

—CH=CH—COO—CH$_2$—, —CH=CH—COO—C$_2$H$_4$—

—CH=CH—COO—C$_3$H$_6$—

As "an alkylene group having 1 to 21 carbon atoms which has at least one group selected from —O—, —OCO—, —COO—, a vinylene group and an arylene group in the chain", in A$_1$ of the general formula (1), among the above-described specific examples, the group represented by the general formulae (6-1), (6-2), (6-5) or (6-6) is preferable, and the group represented b the general formula (6-5) is more preferable.

"An alkylene group having 1 to 21 carbon atoms which has at least one group selected from —O—, —OCO—, —COO—, a vinylene group and an arylene group in the chain, and also has a hydroxy group as a substituent", in A$_1$ of the general formula (1), includes, for example, the group represented by the following general formula (7-1) or (7-2), and the like.

—R$_{52}$—X$_1$—R$_{52}$—  (7-1)

(wherein two pieces of R$_{52}$ each independently represent an alkylene group having 1 to 10 carbon atoms, which has a hydroxy group as a substituent or which is unsubstituted; X$_1$ is the same as described above; and at least one of the two pieces of R$_{52}$ represents the alkylene group having 1 to 6 carbon atoms, which has a hydroxy group as a substituent.)

—R$_{52}$—X$_1$—R$_{52}$—X$_1$—R$_{52}$—  (7-2)

(wherein three pieces of R$_{52}$ are each independently the same as described above; two pieces of X$_1$ are also each independently the same as described above; and at least one of the three pieces of R$_{52}$ represents the alkylene group having 1 to 10 carbon atoms, which has a hydroxy group as a substituent, and the total number of carbon atoms in the formula is 21 or less.)

As the alkylene group having 1 to 10 carbon atoms which has a hydroxy group as a substituent, in R$_{52}$ of the general formulae (7-1) and (7-2), the one having 1 to 6 carbon atoms is preferable, and the one having 1 to 3 carbon atoms is more preferable, and the one having one or two hydroxy groups is preferable. It includes specifically, for example, a hydroxymethylene group, a hydroxyethylene group, a hydroxypropylene group, a hydroxybutylene group, a hydroxypentylene group, a hydroxyhexylene group, a hydroxymethylpentylene group, a hydroxy-n-heptylene group, a hydroxy-n-octylene group, a hydroxy-n-nonylene group, a hydroxy-n-decylene group, a hydroxycyclopentylene group, a hydroxycyclohexylene group, a dihydroxyethylene group, a dihydroxypropylene group, and the like.

The alkylene group having 1 to 10 carbon atoms which is unsubstituted, in R$_{52}$ of the general formulae (7-1) and (7-2) includes the same one as the alkylene group having 1 to 10 carbon atoms in R$_{51}$ of the general formulae (6-1) and (6-2), and the preferable ones are also the same.

The arylene group in X$_1$ of the general formulae (7-1) and (7-2) includes a phenylene group and a naphthylene group, and a phenylene group is preferable.

Preferable specific examples of the group represented by the general formula (7-1) include, for example, the following general formulae (wherein X$_{11}$ represents —O—, —OCO—, COO—, a vinylene group, or a phenylene group).

—CH$_2$—X$_{11}$—C$_3$H$_5$(OH)—

—CH$_2$—X$_{11}$—C$_4$H$_7$(OH)—

—$CH_2$—$X_{11}$—$C_5H_9(OH)$—

—$CH_2$—$X_{11}$—$C_6H_{11}(OH)$—

—$C_2H_4$—$X_{11}$—$C_3H_5(OH)$—

—$C_2H_4$—$X_{11}$—$C_4H_7(OH)$—

—$C_2H_4$—$X_{11}$—$C_5H_9(OH)$—

—$C_2H_4$—$X_{11}$—$C_6H_{11}(OH)$—

—$C_3H_6$—$X_{11}$—$C_3H_5(OH)$—

—$C_3H_6$—$X_{11}$—$C_4H_7(OH)$—

—$C_3H_6$—$X_{11}$—$C_5H_9(OH)$—

—$C_3H_6$—$X_{11}$—$C_6H_{11}(OH)$—

—$C_3H_5(OH)$—$X_{11}$—$CH_2$—

—$C_3H_5(OH)$—$X_{11}$—$C_2H_4$—

—$C_3H_5(OH)$—$X_{11}$—$C_3H_6$—

—$C_3H_5(OH)$—$X_{11}$—$C_4H_8$—

—$C_3H_5(OH)$—$X_{11}$$C_5H_{10}$—

—$C_3H_5(OH)$—$X_{11}$—$C_6H_{12}$—

—$C_3H_5(OH)$—$X_{11}$—$C_3H_5(OH)$—

—$C_3H_5(OH)$—$X_{11}$—$C_4H_7(OH)$—

—$C_3H_5(OH)$—$X_{11}$—$C_5H_9(OH)$—

—$C_3H_5(OH)$—$X_{11}$—$C_6H_{11}(OH)$—

Preferable specific examples of the group represented by the general formula (7-2) include, for example, the following general formulae (wherein $X_{11}$ each independently represent —O—, —OCO—, COO—, a vinylene group, or a phenylene group).

—$CH_2$—$X_{11}$—$C_3H_5(OH)$—$X_{11}$—$CH_2$—

—$C_2H_4$—$X_{11}$—$C_3H_5(OH)$—$X_{11}$—$C_2H_4$—

—$C_2H_4$—$X_{11}$—$C_3H_5(OH)$—$X_{11}$—$C_3H_6$—

—$C_2H_4$—$X_{11}$—$C_3H_5(OH)$—$X_{11}$—$C_4H_8$—

—$C_2H_4$—$X_{11}$—$C_3H_5(OH)$—$X_{11}$—$C_5H_{10}$—

—$C_2H_4$—$X_{11}$—$C_3H_5(OH)$—$X_{11}$—$C_6H_{12}$—

—$C_3H_6$—$X_{11}$—$C_3H_5(OH)$—$X_{11}$—$C_2H_4$—

—$C_3H_6$—$X_{11}$—$C_3H_5(OH)$—$X_{11}$—$C_3H_6$—

—$C_3H_6$—$X_{11}$—$C_3H_5(OH)$—$X_{11}$—$C_4H_8$—

—$C_3H_6$—$X_{11}$—$C_3H_5(OH)$—$X_{11}$—$C_5H_{10}$—

—$C_3H_6$—$X_{11}$—$C_3H_5(OH)$—$X_{11}$—$C_6H_{12}$—

—$C_4H_8$—$X_{11}$—$C_3H_5(OH)$—$X_{11}$—$C_4H_8$—

—$C_5H_{10}$—$X_{11}$—$C_3H_5(OH)$—$X_{11}$—$C_5H_{10}$—

—$C_6H_{12}$—$X_{11}$—$C_3H_5(OH)$—$X_{11}$—$C_6H_{12}$—

—$C_2H_4$—$X_{11}$—$C_3H_5(OH)$—$X_{11}$—$C_3H_5(OH)$—

—$C_2H_4$—$X_{11}$—$C_3H_5(OH)$—$X_{11}$—$C_4H_7(OH)$—

—$C_2H_4$—$X_{11}$—$C_3H_5(OH)$—$X_{11}$—$C_5H_9(OH)$—

—$C_2H_4$—$X_{11}$—$C_3H_5(OH)$—$X_{11}$—$C_6H_{11}(OH)$—

—$C_3H_6$—$X_{11}$—$C_3H_5(OH)$—$X_{11}$—$C_2H_3(OH)$—

—$C_3H_6$—$X_{11}$—$C_3H_5(OH)$—$X_{11}$—$C_3H_5(OH)$—

—$C_4H_8$—$X_{11}$—$C_3H_5(OH)$—$X_{11}$—$C_4H_7(OH)$—

—$C_5H_{10}$—$X_{11}$—$C_3H_5(OH)$—$X_{11}$—$C_5H_9(OH)$—

—$C_6H_{12}$—$X_{11}$—$C_3H_5(OH)$—$X_{11}$—$C_6H_{11}(OH)$—

"An alkylene group having 1 to 21 carbon atoms which has a hydroxy group as a substituent" in $A_1$ of the general formula (1) includes, for example, the group represented by the following general formula (8).

$$-(CH_2)_{p10}-R_{56}-(CH_2)_{p10}- \quad (8)$$

(wherein $R_{56}$ represents the alkylene group having 1 to 9 carbon atoms which has a hydroxy group as a substituent; and p10 represents an integer of 0 to 6.)

As the alkylene group having 1 to 9 carbon atoms which has a hydroxy group as a substituent, in $R_{56}$ of the general formula (8), the one having 1 to 6 carbon atoms is preferable, and the one having 1 to 3 carbon atoms is more preferable. It includes specifically, for example, a hydroxymethylene group, a hydroxyethylene group, a hydroxypropylene group, a hydroxymethylethylene group, a hydroxybutylene group, a 1-hydroxymethylpropylene group, a 2-hydroxymethylpropylene group, a hydroxypentylene group, a hydroxymethylbutylene group, a 1,2-dihydroxymethylpropylene group, a 1-hydroxyethylpropylene group, a hydroxyhexylene group, a hydroxymethylpentylene group, a hydroxy-n-heptylene group, a hydroxy-n-octylene group, a hydroxy-n-nonylene group, a hydroxycyclopentylene group, a hydroxycyclohexylene group, a hydroxycycloheptylene group, and the like, and a hydroxymethylene group, a hydroxyethylene group and a hydroxypropylene group are more preferable, and a hydroxyethylene group is particularly preferable.

The group represented by the general formula (8) specifically includes, for example,

—$CH_2$—$C_6H_9(OH)$—$CH_2$—,

—$C_2H_4$—$C_6H_9(OH)$—$C_2H_4$—,

—$C_3H_6$—$C_6H_9(OH)$—$C_3H_6$—,

—$CH_2$—$CH(OH)$—$C_2H_4$—

—$CH_2$—$CH(OH)$—$C_3H_6$—

—$CH_2$—$CH(OH)$—$C_4H_8$—

—$C_2H_4$—$CH(OH)$—$CH_2$—

—$C_2H_4$—$CH(OH)$—$C_2H_4$—

—$C_2H_4$—$CH(OH)$—$C_3H_6$—

—$CH_2$—$C_2H_4(OH)$—$C_2H_4$—

—$CH_2$—$C_2H_4(OH)$—$C_3H_6$—

—$CH_2$—$C_2H_4(OH)$—$C_4H_8$—

—C$_2$H$_4$—C$_2$H$_4$(OH)—CH$_2$—

—C$_2$H$_4$—C$_2$H$_4$(OH)—C$_2$H$_4$—

—C$_2$H$_4$—C$_2$H$_4$(OH)—C$_3$H$_6$— and the like.

As A$_1$ in the general formula (1), the alkylene group having 1 to 21 carbon atoms which has at least one group selected from —O—, —OCO—, —COO—, a vinylene group and an arylene group in the chain; or the alkylene group having 1 to 21 carbon atoms is preferable. Among them, the group represented by the general formula (6-1), the group represented by the general formula (6-2), the group represented by the general formula (6-5), the group represented by the general formula (6-6), and the alkylene group having 1 to 12 carbon atoms are more preferable; and the group represented by the general formula (6-5), and the alkylene group having 1 to 6 carbon atoms are still more preferable; and the group represented by the general formula (6-5) is particularly preferable. In addition, A$_1$ is preferably in the ortho-position or the para-position relative to the —NH— group, and more preferably in the para-position.

As A$_2$, —O— is preferable.

Preferable combinations of R$_1$ to R$_7$, R$_8$, R$_{12}$, n, A$_1$ and A$_2$ of the general formula (1) include, for example, those described in the following Table. The ortho-position described in the column A$_1$ means that it is in the ortho-position relative to the —NH— group, and that all of the other A$_1$ are in the para-position relative to the —NH— group.

Specific examples and the preferable ones of An$^-$ of the general formula (1) are as described in the anion containing the aryl group having the electron-withdrawing substituent, the sulfonyl group having the electron-withdrawing substituent, or the halogenated alkyl group.

[Production Method for the Compound of the Present Invention]

The compound of the present invention is produced, for example, (I) by reacting a compound represented by the following general formula (20), with a compound represented by the following general formula (21), a compound represented by the general formula (22), or a compound represented by the general formula (23), and then, carrying out a salt exchange reaction; or (II) by reacting a compound represented by the following general formula (24) with a compound represented by the following general formula (25), and then, carrying out the salt exchange reaction.

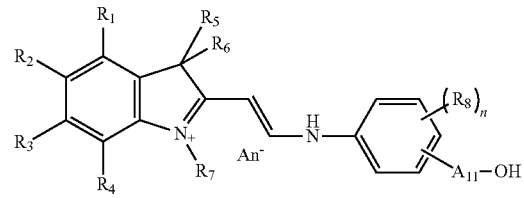

(20)

| R$_1$ to R$_4$ | R$_5$ | R$_6$ | R$_7$ | R$_8$ | n | R$_{12}$ | A$_1$ | A$_2$ |
|---|---|---|---|---|---|---|---|---|
| all —H | —CH$_3$ | —CH$_3$ | —CH$_3$ | — | 0 | —H or —CH$_3$ | —CH$_2$— | —O— |
| all —H | —CH$_3$ | —CH$_3$ | —CH$_3$ | — | 0 | —H or —CH$_3$ | —C$_2$H$_4$— | —O— |
| all —H | —CH$_3$ | —CH$_3$ | —CH$_3$ | — | 0 | —H or —CH$_3$ | —C$_3$H$_6$— | —O— |
| all —H | —CH$_3$ | —CH$_3$ | —CH$_3$ | — | 0 | —H or —CH$_3$ | —C$_5$H$_{10}$— | —O— |
| all —H | —CH$_3$ | —CH$_3$ | —CH$_3$ | — | 0 | —H or —CH$_3$ | —C$_6$H$_{12}$— | —O— |
| all —H | —CH$_3$ | —CH$_3$ | —CH$_3$ | — | 0 | —H or —CH$_3$ | —CH$_2$—OCO—C$_2$H$_4$—COO—CH$_2$— | —O— |
| all —H | —CH$_3$ | —CH$_3$ | —CH$_3$ | — | 0 | —H or —CH$_3$ | —CH$_2$—OCO—C$_2$H$_4$—COO—C$_2$H$_4$— | —O— |
| all —H | —CH$_3$ | —CH$_3$ | —CH$_3$ | — | 0 | —H or —CH$_3$ | —C$_2$H$_4$—OCO—C$_2$H$_4$—COO—CH$_2$— | —O— |
| all —H | —CH$_3$ | —CH$_3$ | —CH$_3$ | — | 0 | —H or —CH$_3$ | —C$_2$H$_4$—OCO—C$_2$H$_4$—COO—C$_2$H$_4$— | —O— |
| all —H | —CH$_3$ | —CH$_3$ | —CH$_3$ | — | 0 | —H or —CH$_3$ | —C$_2$H$_4$—OCO—C$_2$H$_4$—COO—C$_3$H$_6$— | —O— |
| all —H | —CH$_3$ | —CH$_3$ | —CH$_3$ | — | 0 | —H or —CH$_3$ | —C$_2$H$_4$—OCO—C$_2$H$_4$—COO—C$_4$H$_8$— | —O— |
| all —H | —CH$_3$ | —CH$_3$ | —CH$_3$ | — | 0 | —H or —CH$_3$ | —C$_2$H$_4$—OCO—C$_2$H$_4$—COO—C$_5$H$_{10}$— | —O— |
| all —H | —CH$_3$ | —CH$_3$ | —CH$_3$ | — | 0 | —H or —CH$_3$ | —C$_2$H$_4$—OCO—C$_2$H$_4$—COO—C$_6$H$_{12}$— | —O— |
| all —H | —CH$_3$ | —CH$_3$ | —CH$_3$ | — | 0 | —H or —CH$_3$ | —C$_3$H$_6$—OCO—C$_2$H$_4$—COO—CH$_2$— | —O— |
| all —H | —CH$_3$ | —CH$_3$ | —CH$_3$ | — | 0 | —H or —CH$_3$ | —C$_3$H$_6$—OCO—C$_2$H$_4$—COO—C$_2$H$_4$— | —O— |
| all —H | —CH$_3$ | —CH$_3$ | —CH$_3$ | — | 0 | —H or —CH$_3$ | —C$_3$H$_6$—OCO—C$_2$H$_4$—COO—C$_3$H$_6$— | —O— |
| all —H | —CH$_3$ | —CH$_3$ | —CH$_3$ | — | 0 | —H or —CH$_3$ | —CH$_2$—COO—CH$_2$— | —O— |
| all —H | —CH$_3$ | —CH$_3$ | —CH$_3$ | — | 0 | —H or —CH$_3$ | —CH$_2$—COO—C$_2$H$_4$— | —O— |
| all —H | —CH$_3$ | —CH$_3$ | —CH$_3$ | — | 0 | —H or —CH$_3$ | —CH$_2$—COO—C$_3$H$_6$— | —O— |
| all —H | —CH$_3$ | —CH$_3$ | —CH$_3$ | — | 0 | —H or —CH$_3$ | —C$_2$H$_4$—COO—CH$_2$— | —O— |
| all —H | —CH$_3$ | —CH$_3$ | —CH$_3$ | — | 0 | —H or —CH$_3$ | —C$_2$H$_4$—COO—C$_2$H$_4$— | —O— |
| all —H | —CH$_3$ | —CH$_3$ | —CH$_3$ | — | 0 | —H or —CH$_3$ | —C$_2$H$_4$—COO—C$_3$H$_6$— | —O— |
| all —H | —CH$_3$ | —CH$_3$ | —CH$_3$ | — | 0 | —H or —CH$_3$ | —C$_3$H$_6$—COO—CH$_2$— | —O— |
| all —H | —CH$_3$ | —CH$_3$ | —CH$_3$ | — | 0 | —H or —CH$_3$ | —C$_3$H$_6$—COO—C$_2$H$_4$— | —O— |
| all —H | —CH$_3$ | —CH$_3$ | —CH$_3$ | — | 0 | —H or —CH$_3$ | —C$_3$H$_6$—COO—C$_3$H$_6$— | —O— |
| all —H | —CH$_3$ | —CH$_3$ | —CH$_3$ | —OMe | 1 | —H or —CH$_3$ | —COO—CH$_2$— (ortho position) | —O— |
| all —H | —CH$_3$ | —CH$_3$ | —CH$_3$ | —OMe | 1 | —H or —CH$_3$ | —COO—C$_2$H$_4$— (ortho position) | —O— |
| all —H | —CH$_3$ | —CH$_3$ | —CH$_3$ | —OMe | 1 | —H or —CH$_3$ | —COO—C$_3$H$_6$— (ortho position) | —O— |
| all —H | —CH$_3$ | —CH$_3$ | —CH$_3$ | —OMe | 2 | —H or —CH$_3$ | —COO—CH$_2$— (ortho position) | —O— |
| all —H | —CH$_3$ | —CH$_3$ | —CH$_3$ | —OMe | 2 | —H or —CH$_3$ | —COO—C$_2$H$_4$— (ortho position) | —O— |
| all —H | —CH$_3$ | —CH$_3$ | —CH$_3$ | —OMe | 2 | —H or —CH$_3$ | —COO—C$_3$H$_6$— (ortho position) | —O— |
| all —H | —CH$_3$ | —CH$_3$ | —CH$_3$ | — | 0 | —H or —CH$_3$ | —CH=CH—COO—CH$_2$— | —O— |
| all —H | —CH$_3$ | —CH$_3$ | —CH$_3$ | — | 0 | —H or —CH$_3$ | —CH=CH—COO—C$_2$H$_4$— | —O— |
| all —H | —CH$_3$ | —CH$_3$ | —CH$_3$ | — | 0 | —H or —CH$_3$ | —CH=CH—COO—C$_3$H$_6$— | —O— |
| all —H | —CH$_3$ | —CH$_3$ | —CH$_3$ | — | 0 | —H or —CH$_3$ | —CH=CH—COO—CH$_2$— (ortho position) | —O— |
| all —H | —CH$_3$ | —CH$_3$ | —CH$_3$ | — | 0 | —H or —CH$_3$ | —CH=CH—COO—C$_2$H$_4$— (ortho position) | —O— |
| all —H | —CH$_3$ | —CH$_3$ | —CH$_3$ | — | 0 | —H or —CH$_3$ | —CH=CH—COO—C$_3$H$_6$— (ortho position) | —O— |

(wherein $R_1$ to $R_8$, n and $An^-$ are the same as described above; $A_{11}$ represents an alkylene group having 1 to 6 carbon atoms, which has a hydroxy group as a substituent or which is unsubstituted.)

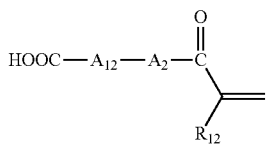

(21)

(wherein $R_{12}$ and $A_2$ are the same as described above; $A_{12}$ represents an alkylene group having 1 to 15 carbon atoms which has at least one group selected from —O—, —OCO—, —COO—, a vinylene group and an arylene group in the chain; an alkylene group having 1 to 15 carbon atoms which has at least one group selected from —O—, —OCO—, —COO—, a vinylene group and an arylene group in the chain, and also has a hydroxy group as a substituent; an alkylene group having 1 to 15 carbon atoms; or an alkylene group having 1 to 15 carbon atoms which has a hydroxy group as a substituent.)

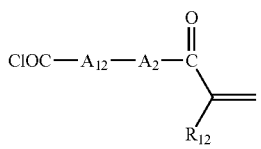

(22)

(wherein $R_{12}$, $A_2$ and $A_{12}$ are the same as described above.)

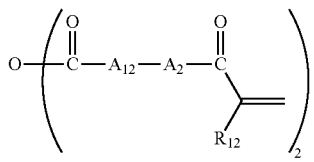

(23)

(wherein $R_{12}$, $A_2$ and $A_{12}$ are the same as described above.)

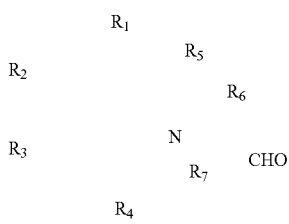

(24)

(wherein $R_1$ to $R_7$ are the same as described above.)

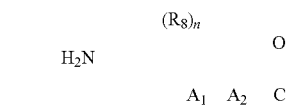

(25)

(wherein $R_8$, $R_{12}$, n, $A_1$ and $A_2$ are the same as described above.)

As the alkylene group having 1 to 6 carbon atoms which has a hydroxy group as a substituent, in $A_{11}$ of the general formula (20), the one having 1 to 3 carbon atoms is preferable, and the one having one or two hydroxy groups is preferable. It includes specifically, for example, a hydroxymethylene group, a hydroxyethylene group, a hydroxypropylene group, a hydroxybutylene group, a hydroxypentylene group, a hydroxyhexylene group, a hydroxycyclopentylene group, a hydroxycyclohexylene group, a dihydroxyethylene group, a dihydroxypropylene group, and the like.

The alkylene group having 1 to 6 carbon atoms which is unsubstituted, in $A_{11}$ of the general formula (20), includes a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, and the like, and a methylene group, an ethylene group and a propylene group are more preferable, and an ethylene group is particularly preferable.

Preferable combinations of $R_1$ to $R_8$, $An^-$ and $A_{11}$ in the general formula (20) include those where combinations of $R_1$ to $R_{11}$ described in the Table of the paragraph of the compound of the present invention. $An^-$ represented by the general formula (16), as well as $A_{11}$ selected from a methylene group, an ethylene group and a propylene group are combined appropriately.

The compound represented by the general formula (20) may be the one commercially available, or the one synthesized by a method known per se.

The alkylene group having 1 to 15 carbon atoms which has at least one group selected from —O—, —OCO—, —COO—, a vinylene group and an arylene group in the chain, and also having a hydroxy group as a substituent, in $A_{12}$ of the general formulae (21), (22) and (23), includes, for example, the group represented by the following general formulae (6-1') to (6-4'), and the like.

—$R_{51}$—$X_1$—$R_{51}$— (6-1')

(wherein two pieces of $R_{51}$ each independently represent an alkylene group having 1 to 10 carbon atoms; $X_1$ is the same as described above, and the total number of carbon atoms in the formula is 15 or less.)

—$R_{51}$—$X_1$—$R_{51}$—$X_1$—$R_{51}$— (6-2')

(wherein three pieces of $R_{51}$ are each independently the same as described above; $X_1$ is the same as described above, and the total number of carbon atoms in the formula is 15 or less.)

—$R_{51}$—$(C_2H_4O)_{p7}$—$R_{51}$— (6-3')

(wherein two pieces of $R_{51}$ are each independently the same as described above; and p7 represents an integer of 1 to 9, and the total number of carbon atoms in the formula is 15 or less.)

—$R_{51}$—$(CH_2CH(CH_3)O)_{p9}$—$R_{51}$— (6-4')

(wherein two pieces of $R_{51}$ are each independently the same as described above; and p9 represents an integer of 1 to 9, and the total number of carbon atoms in the formula is 15 or less.)

Preferable specific examples of the group represented by the general formulae (6-1') to (6-4') include those in accordance with the preferable specific examples of the group represented by the general formulae (6-1) to (6-4).

The alkylene group having 1 to 15 carbon atoms which has at least one group selected from —O—, —OCO—, —COO—, a vinylene group and an arylene group in the chain, in $A_{12}$ of the general formulae (21), (22) and (23), includes, for example, the group represented by the following general formulae (7-1') or (7-2'), and the like.

(wherein $R_{52}$ and $X_1$ are the same as described above, and the total number of carbon atoms in the formula is 15 or less.)

(wherein $R_{52}$ and $X_1$ are the same as described above, and the total number of carbon atoms in the formula is 15 or less.)

Preferable specific examples of the group represented by the general formulae (7-1') or (7-2') include those in accordance with the preferable specific examples of the group represented by the general formulae (7-1) or (7-2).

The alkylene group having 1 to 15 carbon atoms in $A_{12}$ of the general formulae (21), (22) and (23) is the straight chained or branched one, and the one having 1 to 6 carbon atoms is preferable, and the one having 1 to 3 carbon atoms is more preferable. It includes specifically, for example, a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, a methylpentylene group, a n-heptylene group, a n-octylene group, a n-nonylene group, a n-decylene group, a n-undecylene group, a n-dodecylene group, a n-tridecylene group, a n-tetradecylene group, a n-pentadecylene group, a cyclopentylene group, a cyclohexylene group, a cycloheptylene group, and the like. A methylene group, an ethylene group, a propylene group, a butylene group, a pentylene group, a hexylene group, and the like, are preferable, and a methylene group, an ethylene group and a propylene group are more preferable, and an ethylene group is particularly preferable.

The alkylene group having 1 to 15 carbon atoms which has a hydroxy group as a substituent, in $A_{12}$ of the general formulae (21), (22) and (23), includes, for example, the group represented by the following general formula (8'), and the like.

(wherein $R_{56}$ represents an alkylene group having 1 to 9 carbon atoms which has a hydroxy group as a substituent; p10 represents an integer of 0 to 6, and the total number of carbon atoms in the formula is 15 or less.)

Preferable specific examples of the group represented by the general formula (8') include those in accordance with the preferable specific examples of the group represented by the general formula (8).

Preferable specific examples of the group represented by the general formula (21) include the following general formula (21').

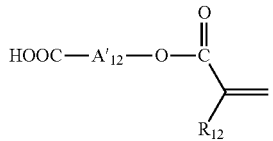

[wherein $R_{12}$ is the same as described above; $A'_{12}$ represents the general formulae (6-1') and (6-2'), or an alkylene group having 1 to 6 carbon atoms.]

The alkylene group having 1 to 6 carbon atoms in $A'_{12}$ includes a methylene group, an ethylene group, a propylene group, a methylethylene group, a butylene group, a 1-methylpropylene group, a 2-methylpropylene group, a pentylene group, a methylbutylene group, a 1,2-dimethylpropylene group, a 1-ethylpropylene group, a hexylene group, and the like, and a methylene group an ethylene group and a propylene group are more preferable, and an ethylene group is particularly preferable.

Preferable specific examples of the general formula (22) include the following general formula (22').

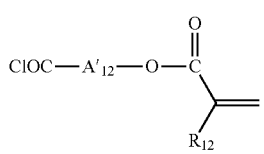

(wherein $R_{12}$ and $A'_{12}$ are the same as described above.)

Preferable specific examples of the general formula (23) include the following general formula (23').

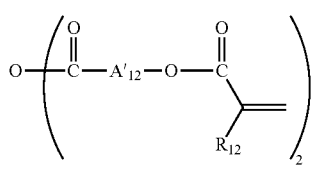

(wherein $R_{12}$ and $A'_{12}$ are the same as described above.)

The reaction between the compound represented by the general formula (20) and the compound represented by the general formula (21) may be carried out, in a solvent, under the presence of a dehydration condensation agent, usually at 10 to 50° C., preferably at 10 to 30° C., for usually 1 to 50 hours, and preferably 5 to 30 hours.

Use amount of the compound represented by the general formula (21) is usually 1 to 5 times mole, and preferably 1 to 2 times mole of the compound represented by the general formula (20).

The above-described solvent includes, for example, ethers such as diethyl ether, diisopropyl ether, ethyl methyl ether, tetrahydrofuran, 1,4-dioxane and dimethoxyethane; halogenated hydrocarbons such as chloromethane, methylene, chloride, chloroform, carbon tetrachloride, dichloroethane, trichloroethane and chlorobenzene; hydrocarbons such as n-hexane, benzene, toluene and xylene; nitriles such as acetonitrile; amides such as N,N-dimethylformamide; and the like; and among them, halogenated hydrocarbons are preferable.

The above-described dehydration condensation agent may be, for example, the one generally used as a dehydration condensation agent, including, for example, inorganic dehydrating agents such as diphosphorus pentaoxide and anhydrous zinc chloride; carbodiimides such as dicyclohexylcarbodiimide, diisopropylcarbodiimide and 1-ethyl-3-(3-dimethylaminopropylcarbodiimide) hydrochloride; for example, polyphosphoric acid, acetic anhydride, sulfuric acid, carbonyldiimidazole, p-toluene sulfonic acid; and the like; and carbodiimides are preferable. Use amount of the dehydration condensation agent is 1 to 10 times mole, and preferably 1 to 5 times mole of the compound represented by the general formula (22). In the reaction, a catalyst such as dimethylaminopyridine, may be used to enhance efficiency of the dehydration condensation agent. Use amount of the catalyst is 0.1 to 10 times mole of the compound represented by the general formula (22).

The reaction between the compound represented by the general formula (20), and the compound represented by the following general formula (22) or the compound represented by the general formula (23) may be carried out, in a solvent, usually at 60 to 90° C., preferably at 70 to 90° C., for usually 1 to 10 hours, and preferably 3 to 5 hours. It is preferable that the reaction is carried out in the presence of a molecular sieve. The presence of the molecular sieve makes it possible to adsorb hydrochloric acid gas, which is a by-product, and accelerate the reaction. Use amount of the molecular sieve is usually 1 to 5 times weight, and preferably 1 to 3 times weight of the compound represented by the general formula (20).

Use amount of the compound represented by the general formula (22) is usually 1 to 5 times mole, and preferably 1 to 3 times mole of the compound represented by the general formula (20).

The above-described solvent includes the same one as the solvent used in the reaction between the compound represented by the general formula (20) and the compound represented by the general formula (21).

The salt exchange reaction, in the production method for the compound of the present invention, may be carried out by making a salt of the anion of the present invention contacted, in a solvent, with the compound obtained by the reaction between the compound represented by the general formula (20) and the compound represented by the general formula (21), the general formula (22) or the general formula (23).

The salt exchange reaction is carried out usually at 10 to 50° C., preferably at 20 to 30° C., for 0.1 to 10 hours, and preferably 0.1 to 6 hours. The solvent used in this case includes the same one as the solvent used in the reaction between the compound represented by the general formula (20) and the compound represented by the general formula (21).

The salt of the anion of the present invention includes, a sodium salt, a potassium salt, a lithium salt, and the like, with the anion, and a potassium salt and a lithium salt are preferable. Use amount of the salt of the anion of the present invention is usually 1 to 2 mole amount, and preferably 1 to 1.5 mole amount, relative to 1 mole of the compound represented by the general formula (20).

In the case of the reaction between the compound represented by the general formula (20) and the compound represented by the general formula (21), specifically, for example, firstly, the compound represented by the general formula (20), and the compound represented by the general formula (21), in 1 to 2 times mole of the compound represented by the general formula (20), are subjected to reaction; in the presence of dimethylaminopyridine, in 0.1 to 1 times mole the compound represented by the general formula (20); and carbodiimides in 1 to 5 times mole of the compound represented by the general formula (20); in a solvent of a halogenated hydrocarbon such as chloromethane, methylene chloride, chloroform, carbon tetrachloride, dichloroethane, trichloroethane and chlorobenzene; at 10 to 30° C. for 5 to 30 hours. Subsequently, for example, a lithium salt of the boron represented by the general formula (16), in 1 to 2 times mole of the compound represented by the general formula (20), is added to the resulting reaction product, and they are subjected to reaction in a solvent of a halogenated hydrocarbon such as chloromethane, methylene chloride, chloroform, carbon tetrachloride, dichloroethane, trichloroethane and chlorobenzene, at 10 to 50° C. for 0.1 to 6 hours, and thus the compound of the present invention can be obtained.

In addition, the compound of the present invention may be produced by a salt exchange reaction of the compound represented by the general formula (20), followed by a reaction between the salt-exchanged compound represented by the general formula (20), and the compound represented by the general formula (21), the compound represented by the general formula (22) or the compound represented by the general formula (23).

The salt exchange reaction in this case may be carried out by making a salt of the anion of the present invention contacted, in a solvent, with the compound represented by the general formula (20). The salt of the anion of the present invention, the solvent, reaction condition, and the like, which is used herein, includes the same one as in the salt exchange reaction.

In addition, reaction condition or other conditions of the reaction between the compound represented by the general formula (20) after the salt exchange reaction and the compound represented by the general formula (21), the reaction between the compound represented by the general formula (20) after the salt exchange reaction and the compound represented by the general formula (22), as well as the reaction between the compound represented by the general formula (20) after the salt exchange reaction and the compound represented by the general formula (23), are the same as in the production method for the compound of the present invention.

In the case of the reaction between the compound represented by the general formula (20) and the compound represented by the general formula (22), specifically, for example, firstly, a lithium salt of the boron represented by the general formula (16), in 1 to 2 times mole of the compound represented by the general formula (20), is added to the compound represented by the general formula (20); and they are subjected to reaction in a solvent of a halogenated hydrocarbon such as chloromethane, methylene chloride, chloroform, carbon tetrachloride, dichloroethane, trichloroethane and chlorobenzene, at 10 to 50° C., for 0.1 to 6 hours. Subsequently the resulting salt-exchanged compound represented by the general formula (20), and the compound represented by the general formula (21), in 1 to 2 times mole of the compound represented by the general formula (20), are subjected to reaction in a solvent of a halogenated hydrocarbon such as chloromethane, methylene chloride, chloroform, carbon tetrachloride, dichloroethane, trichloroethane and chlorobenzene, at 70 to 90° C. for 3 to 5 hours, and thus the compound of the present invention can be obtained.

Preferable combinations of $R_1$ to $R_7$ in the general formula (24) include those in accordance with combinations of $R_1$ to $R_7$ described in Table of the paragraph of the compound of the present invention.

Preferable combinations of $R_8$, $R_{12}$, n, $A_1$ and $A_2$ in the general formula (25) include those in accordance with combinations of $R_8$, $R_{12}$, n, $A_1$ and $A_2$ described in Table of the paragraph of the compound of the present invention.

Preferable specific examples of the general formula (24) include the following general formula (24').

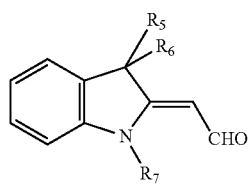
(24')

(wherein $R_6$ to $R_7$ are the same as described above.)

Preferable specific examples of the general formula (25) include the following general formula (25').

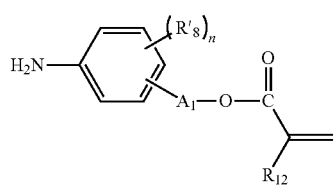
(25')

[wherein $R_{12}$, n and $A_1$ are the same as described above; $R'_8$ represents an alkoxy group having 1 to 6.]

The alkoxy group having 1 to 6 carbon atoms in the $R'^8$ includes a methoxy group, an ethoxy group, a n-propoxy group, a n-butoxy group, a n-pentyloxy group, a n-hexyloxy group, and the like, and a methoxy group, an ethoxy group and a n-propoxy group are preferable, and a methoxy group is more preferable.

The reaction between the compound represented by the general formula (24), and the compound represented by the following general formula (25) may be carried out in a solvent usually at 10 to 70° C., preferably at 40 to 60° C. for usually 1 to 20 hours, and preferably 1 to 10 hours.

Use amount of the compound represented by the general formula (24) is 1 to 5 times mole, and preferably 1 to 2 times mole of the compound represented by the general formula (25).

As the above-described solvent, for example, a carboxylic acid such as acetic acid, propionic acid and butyric acid, may be used alone; or an organic solvent such as nitriles (such as acetonitrile), ethers (such as tetrahydrofuran and 1,4-dioxane), toluene, halogenated hydrocarbons (such as chloromethane, methylene chloride, chloroform, carbon tetrachloride, dichloroethane, trichloroethane and chlorobenzene), and the like, may be mixed with an organic acid such as acetic acid, propionic acid, butyric acid, benzene sulfonic acid and p-toluene sulfonic acid, or with an inorganic acid such as acetic acid, sulfuric acid and nitric acid. Use amount of the acid is 1 to 100 times mole, and preferably 2 to 50 times mole of the compound represented by the general formula (24). Specifically, acetic acid, a mixed solvent of acetonitrile and acetic acid, and the like, is included, and acetic acid is preferable.

In the case of the reaction between the compound represented by the general formula (24) and the compound represented by the general formula (25), specifically, for example, firstly, the compound represented by the general formula (24) and the compound represented by the general formula (25), in 1 to 2 times mole of the compound represented by the general formula (24), are subjected to reaction in a solvent such as acetic acid, at 40 to 60° C. for 1 to 10 hours. Subsequently, for example, after the addition of a saturated sodium chloride aqueous solution into the resulting reaction product, a lithium salt of the boron represented by the general formula (16), in 1 to 2 times mole of the compound represented by the general formula (24), is added, and they are subjected to reaction in a solvent of a halogenated hydrocarbon such as chloromethane, methylene chloride, chloroform, carbon tetrachloride, dichloroethane, trichloroethane and chlorobenzene, at 10 to 50° C. for 0.1 to 6 hours, and thus the compound of the present invention can be obtained.

[Polymer of the Present Invention]

The polymer of the present invention is a polymer having a monomer unit derived from the compound of the present invention.

Weight average molecular weight (Mw) of the polymer of the present invention is usually 2,000 to 100,000, preferably 2,000 to 50,000, and more preferably 2,000 to 30,000. In addition, degree of distribution thereof (Mw/Mn) is usually 1.00 to 5.00, and preferably 1.00 to 3.00.

The polymer of the present invention may be a homopolymer or a copolymer, as long as it is the one having the monomer unit derived from the compound represented by the general formula (1), however, the copolymer is preferable.

The copolymer includes, for example, the one comprising the monomer unit derived from the compound represented by the general formula (1), and 1 to 2 kinds of monomer units derived from the compound represented by the following general formula (2), the general formula (3), the general formula (4), or the general formula (5):

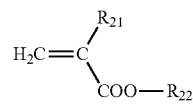
(2)

[wherein $R_{21}$ represents a hydrogen atom or a methyl group; $R_{22}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 10 carbon atoms which has oxygen or no oxygen, a dialkylaminoalkyl group having 3 to 9 carbon atoms, a fluorinated alkyl group having 1 to 18 carbon atoms, or an N-alkylenephthalimide group having 1 to 6 carbon atoms, a group represented by the following general formula (2-1):

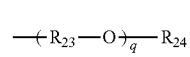
(2-1)

(wherein $R_{23}$ represents an alkylene group having 1 to 3 carbon atoms; $R_{24}$ represents a phenyl group having a hydroxy group as a substituent or not having a substituent, or an alkyl group having 1 to 3 carbon atoms; and q represents an integer of 1 to 3),
a group represented by the following general formula (2-2):

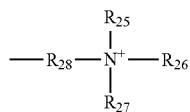
(2-2)

(wherein $R_{25}$ to $R_{27}$ represent an alkyl group having 1 to 3 carbon atoms; $R_{28}$ represents an alkylene group having 1 to 3 carbon atoms),
a group represented by the following general formula (2-3):

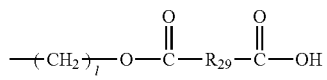
(2-3)

(wherein l represents an integer of 1 to 6; $R_{29}$ represents a phenylene group or a cyclohexylene group.)],

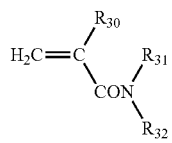
(3)

(wherein $R_{30}$ is the same as described above; $R_{31}$ represents a hydrogen atom or an alkyl group having 1 to 3 carbon atoms; $R_{32}$ represents a hydrogen atom, a dialkylaminoalkyl group having 3 to 9 carbon atoms, or a hydroxyalkyl group having 1 to 6 carbon atoms; $R_{31}$ and $R_{32}$ may form a morpholino group, together with a nitrogen atom adjacent thereto.),

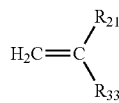
(4)

(wherein $R_{33}$ represents a phenyl group or a pyrrolidino group; and $R_{21}$ is the same as described above.)

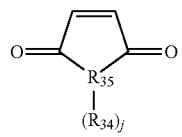
(5)

(wherein $R_{35}$ represents a nitrogen atom or an oxygen atom; j represents 0 when $R_{35}$ is an oxygen atom, and 1 when $R_{35}$ is a nitrogen atom; $R_{34}$ represents hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 1 to 10 carbon atoms, a halogenated cycloalkyl group having 6 to 7 carbon atoms, an aryl group having 6 to 10 carbon atoms, an aryl group having 6 to 10 carbon atoms, which has an alkyl group having 1 to 6 carbon atoms as a substituent, or a halogenated aryl group having 6 to 10 carbon atoms.)

As $R_{21}$ in the general formula (2), a methyl group is preferable.

The alkyl group having 1 to 18 carbon atoms in $R_{22}$ of the general formula (2) may be the straight chained, branched or cyclic one, including, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a cyclopropyl group, a cyclopentyl group, a cyclohexyl group, a cycloheptyl group, a cyclooctyl group, a cyclodecyl group, a cycloundecyl group, a cyclododecyl group, a cyclotetradecyl group, a cyclooctadecyl group, and the like.

The hydroxyalkyl group having 1 to 10 carbon atoms in $R_{22}$ of the general formula (2) includes, for example, a hydroxyethyl group, a hydroxypropyl group, a hydroxybutyl group, a hydroxypentyl group, a hydroxyhexyl group, and the like.

The aryl group having 6 to 10 carbon atoms in $R_{22}$ of the general formula (2) includes a phenyl group, a naphthyl group, and the like.

The arylalkyl group having 7 to 13 carbon atoms in $R_{22}$ of the general formula (2) includes a benzyl group, a phenylethyl group, a phenylpropyl group, a naphthylmethyl group, a naphthylethyl group, a naphthylpropyl group, and the like, and a benzyl group is preferable.

The alkoxyalkyl group having 2 to 9 carbon atoms in $R_{22}$ of the general formula (2) includes a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, a propoxymethyl group, a propoxyethyl group, a propoxypropyl group, a propoxybutyl group, a propoxypentyl group, a propoxyhexyl group, and the like.

The alkoxyalkoxyalkyl group having 3 to 9 carbon atoms in $R_{22}$ of the general formula (2) includes a methoxymethoxymethyl group, a methoxymethoxyethyl group, a methoxymethoxypropyl group, an ethoxymethoxymethyl group, an ethoxymethoxyethyl group, an ethoxymethoxypropyl group, a propoxymethoxymethyl group, a propoxymethoxyethyl group, a propoxymethoxypropyl group, an ethoxyethoxymethyl group, an ethoxyethoxyethyl group, an ethoxyethoxypropyl group, an ethoxyethoxymethyl group, an ethoxyethoxyethyl group, an ethoxyethoxypropyl group, a propoxyethoxymethyl group, a propoxyethoxyethyl group, a propoxyethoxypropyl group, and the like.

The aryloxyalkyl group having 7 to 13 carbon atoms in $R_{22}$ of the general formula (2) includes a phenoxymethyl group, a phenoxyethyl group, a phenoxypropyl group, a naphthyloxymethyl group, a naphthyloxyethyl group, a naphthyloxypropyl group, and the like.

The morpholinoalkyl group having 5 to 7 carbon atoms in $R_{22}$ of the general formula (2) includes, for example, a morpholinomethyl group, a morpholinoethyl group, a morpholinopropyl group, and the like.

The trialkylsilyl group having 3 to 9 carbon atoms in $R_{22}$ of the general formula (2) includes, for example, a trimethylsilyl group, a triethylsilyl group, a tripropylsilyl group, a dimethylethylsilyl group, a diethylmethylsilyl group, and the like.

The alicyclic hydrocarbon group having 6 to 10 carbon atoms which has oxygen, in $R_{22}$ of the general formula (2), includes a dicyclopentenyloxyethyl group, and the like.

The alicyclic hydrocarbon group having 6 to 10 carbon atoms which has no oxygen, in $R_{22}$ of the general formula (2), includes a cyclohexyl group, an isobornyl group, a dicyclopentanyl group, and the like.

The dialkylaminoalkyl group having 3 to 9 carbon atoms in $R_{22}$ of the general formula (2) includes a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The fluorinated alkyl group having 1 to 18 carbon atoms in $R_{22}$ of the general formula (2) includes a 2,2,2-trifluoroethyl group, a 2,2,3,3-tetrafluoropropyl group, a 2,2,3,3-tetrafluoropropyl group, a 2,2,3,3,4,4-hexafluoropropyl group, a 2,2,3,3,4,4,5,5-octafluoropentyl group, a 3,3,4,4,5,5,6,6,7,7,8,8,9,9,10,10,10-heptadecafluorodecyl group, a 2-(heptadecafluorooctyl)ethyl group, and the like.

The N-alkylenephthalimide group having 1 to 6 carbon atoms in $R_{22}$ of the general formula (2) includes a 2-phthalimideethyl group, a 2-tetrahydrophthalimideethyl group, and the like.

The alkylene group having 1 to 3 carbon atoms in $R_{23}$ of the general formula (2-1) includes a methylene group, an ethylene group, a propylene group, and the like, and an ethylene group is preferable.

The phenyl group having a hydroxy group as a substituent or not having a substituent, in $R_{24}$ of the general formula (2-1), includes a hydroxyphenyl group, a phenyl group, and the like.

The alkyl group having 1 to 3 carbon atoms in $R_{24}$ of the general formula (2-1) includes a methyl group, an ethyl group, a propyl group, and the like.

Specific examples of the group represented by the general formula (2-1) include a 2-hydroxy-3-phenoxymethyl group, a 2-hydroxy-3-phenoxyethyl group, a 2-hydroxy-3-phenoxypropyl group, a methyltrimethylene glycol group, a methyltriethylene glycol group, a methyltripropylene glycol group, and the like. Among them, a 2-hydroxy-3-phenoxypropyl group, a methyltripropylene glycol group, a methyltriethylene glycol group, and the like, are preferable.

The alkyl group having 1 to 3 carbon atoms in $R_{26}$ to $R_{27}$ in the general formula (2-2) includes a methyl group, an ethyl group, a propyl group, and the like, and a methyl group is preferable.

The alkylene group having 1 to 3 carbon atoms in $R_{28}$ of the general formula (2-2) includes a methylene group, an ethylene group, a propylene group, and the like.

Preferable specific examples of the group represented by the general formula (2-2) include a trimethylammoniummethyl group, trimethylammoniumethyl group, a triethylammoniummethyl group, a triethylammoniumethyl group, and the like.

Preferable specific examples of the group represented by the general formula (2-3) include, for example, those of the following formulae.

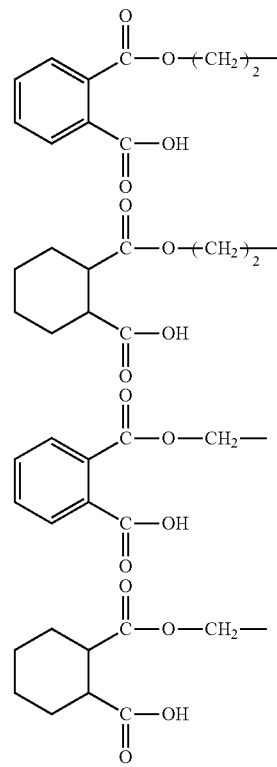

Preferable specific examples of the general formula (2) include methacrylic acid, benzyl methacrylate, hydroxyethyl methacrylate, methyl methacrylate, and the like. Among them, methacrylic acid, benzyl methacrylate, and the like, are preferable.

The alkyl group having 1 to 3 carbon atoms in $R_{31}$ of the general formula (3) includes a methyl group, an ethyl group, a propyl group, and the like.

The dialkylaminoalkyl group having 3 to 9 carbon atoms in $R_{32}$ of the general formula (3) includes a dimethylaminomethyl group, a dimethylaminoethyl group, a dimethylaminopropyl group, a diethylaminomethyl group, a diethylaminoethyl group, a diethylaminopropyl group, a dipropylaminomethyl group, a dipropylaminoethyl group, a dipropylaminopropyl group, and the like.

The alkyl group having 1 to 3 carbon atoms includes the same one as $R_{31}$.

The hydroxyalkyl group having 1 to 6 carbon atoms in $R_{32}$ of the general formula (3) includes a hydroxymethyl group, a hydroxyethyl group, a hydroxypropyl group, a hydroxybutyl group, a hydroxypentyl group, hydroxyhexyl group, and the like, and a hydroxyethyl group is preferable.

Preferable specific examples of the general formula (3) include (meth)acrylamide, N,N-dimethylacrylamide, hydroxyethyl(meth)acrylamide, 4-acryloylmorpholine, and the like.

Preferable specific examples of the general formula (4) include styrene, α-methylstyrene, N-vinylpyrrolidone, and the like.

The alkyl group having 1 to 20 carbon atoms in $R_{34}$ of the general formula (5) may be the straight chained, branched, or cyclic one, including, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a n-heptyl group, an isoheptyl group, a sec-heptyl group, a n-octyl group, an isooctyl group, a sec-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a nonadecyl group, an aralkyl group, and the like.

The hydroxyalkyl group having 1 to 10 carbon atoms in $R_{34}$ of the general formula (5) includes, for example, a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, a hydroxydecyl group, and the like.

The halogenated alkyl group having 1 to 10 carbon atoms in $R_{34}$ of the general formula (5) includes, for example, a chloromethyl group, a chloroethyl group, a chloro-n-propyl group, a chloroisopropyl group, a chloro-n-butyl group, a chloro-tert-butyl group, a chloro-n-pentyl group, a chloro-n-hexyl group, a chloro-n-heptyl group, a chloro-n-octyl group, a chloro-n-nonyl group, chloro-n-decyl group, a fluorinated methyl group, a fluorinated ethyl group, a fluorinated n-propyl group, a fluorinated isopropyl group, a fluorinated n-butyl group, a fluorinated tert-butyl group, a fluorinated n-pentyl group, a fluorinated n-hexyl group, a fluorinated n-heptyl group, a fluorinated n-octyl group, a fluorinated n-nonyl group, a fluorinated n-decyl group, and the like.

The alkylcycloalkyl group having 1 to 10 carbon atoms in $R_{34}$ of the general formula (5) includes, for example, a methylcyclohexyl group, an ethylcyclohexyl group, a propylcyclohexyl group, a butylcyclohexyl group, and the like.

The halogenated cycloalkyl group having 6 to 7 carbon atoms in $R_{34}$ of the general formula (5) includes a chlorocyclohexyl group, a fluorinated cyclohexyl group, a bromocyclohexyl group, a chlorocycloheptyl group, a fluorinated cycloheptyl group, a bromocycloheptyl group, and the like.

The aryl group having 6 to 10 carbon atoms in $R_{34}$ of the general formula (5) includes a phenyl group, a naphthyl group, and the like.

The aryl group having 6 to 10 carbon atoms, which has an alkyl group having 1 to 6 carbon atoms as a substituent, in $R_{34}$ of the general formula (5), includes a methylphenyl group, an ethylphenyl group, a n-propylphenyl group, a n-butylphenyl group, a n-pentylphenyl group, a n-hexylphenyl group, and the like.

The halogenated aryl group having 6 to 10 carbon atoms in $R_{34}$ of the general formula (5) includes a chlorophenyl group, a fluorinated phenyl group, a chloronaphthyl group, a fluorinated naphthyl group, and the like.

Preferable specific examples of the general formula (5) include maleic anhydride, maleimide, N-methylmaleimide, N-ethylmaleimide, N-butylmaleimide, N-octylmaleimide, N-dodecylmaleimide, N-(2-ethylhexyl)maleimide, N-(2-hydroxyethyl)maleimide, N-(2-chlorohexyl)maleimide, N-cyclohexylmaleimide, N-(2-methylcyclohexyl)maleimide, N-(2-ethylcyclohexyl)maleimide, N-(2-chlorocyclohexyl) maleimide, N-phenylmaleimide, N-(2-methylphenyl)maleimide, N-(2-ethylphenyl)maleimide, N-(2-chlorophenyl) maleimide, and the like.

The copolymer of the present invention specifically includes the following combinations of monomer units, and among them, the combination 1 is preferable.

| | Compound from which monomer unit derived | | |
|---|---|---|---|
| Combination 1 | General formula (1) | General formula (2) | |
| Combination 2 | General formula (1) | General formula (3) | |
| Combination 3 | General formula (1) | General formula (4) | |
| Combination 4 | General formula (1) | General formula (5) | |
| Combination 5 | General formula (1) | General formula (2) | General formula (3) |
| Combination 6 | General formula (1) | General formula (2) | General formula (4) |
| Combination 7 | General formula (1) | General formula (2) | General formula (5) |

In the combination 1, a copolymer comprising the compound represented by the general formula (1) and two kinds of the compounds represented by the general formula (2) is preferable. The two kinds of the compounds represented by the general formula (2), in this case, include the case where $R_{21}$ in the general formula (2) is a hydrogen atom or a methyl group, and $R_{22}$ is a hydrogen atom; and the case where $R_{21}$ in the general formula (2) is a hydrogen atom or a methyl group, and $R_{22}$ is an arylalkyl group having 7 to 13 carbon atoms.

Weight ratio of the monomer unit derived from the compound represented by the general formula (1), and the monomer unit derived from compound represented by the general formula (2), the general formula (3), the general formula (4), or the general formula (5) may be set as appropriate, depending on kinds of the monomer units to be used, however, the monomer unit derived from the compound represented by the general formula (1) is usually 1 to 90% by weight, and preferably 5 to 85% by weight, relative to total weight of the resulting polymer.

Preferable specific examples of the copolymer of the present invention include polymers comprising the monomer unit derived from the compound represented by the general formula (1), and one kind or two kinds of the monomer unit derived from the compound represented by the following general formula (2').

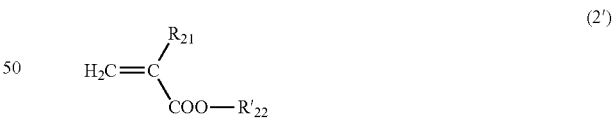

(2')

(wherein $R_{21}$ is the same as described above; $R'_{22}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms.)

Specific examples of the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, and the alkoxyalkyl group having 2 to 9 carbon atoms, in $R'_{22}$, include the same one as those of $R_{22}$.

As $R'_{22}$, a hydrogen atom, an alkyl group having 1 to 18 carbon atoms, and an arylalkyl group having 7 to 13 carbon atoms are preferable, and a hydrogen atom and an arylalkyl group having 7 to 13 carbon atoms are preferable.

Preferable combinations of $R_{21}$ and $R'_{22}$ in the compound represented by the general formula (2') are as follows.

| $R_{21}$ | $R'_{22}$ |
|---|---|
| Methyl group | Benzyl group |
| Hydrogen atom | Benzyl group |
| Methyl group | Hydrogen atom |
| Hydrogen atom | Hydrogen atom |

[Production Method for the Polymer of the Present Invention]

The polymer of the present invention is produced, for example, as follows. That is, the polymer of the present invention can be obtained by subjecting the compound of the present invention, as a monomer, to a polymerization reaction known per se. When the polymer of the present invention is a copolymer, in the polymerization reaction, after mixing the compound of the present invention with 1 to 2 kinds of the compounds represented by the general formula (2), the general formula (3), the general formula (4) or the general formula (5), so that ratio of the monomer unit derived from each monomer in the finally obtained polymer attains as described above, polymerization may be carried out.

The above-described polymerization reaction is carried out, for example, as follows. That is, the compound represented by the general formula (1), and, as needed, still more one or two kinds of the compound represented by the general formula (2), the general formula (3), the general formula (4) or the general formula (5), are dissolved in an appropriate solvent of 1 to 10 times volume relative to total volume thereof, such as toluene, 1,4-dioxane, tetrahydrofuran, isopropanol, methyl ethyl ketone and propylene glycol monomethyl ether acetate; and then, in the presence of a polymerization initiator of 0.01 to 30% by weight relative to total amount of the dissolved compounds such as azoisobutyronitrile, 2,2'-azobis(2,4-dimethylvaleronitrile), 2,2'-azobis(2-methylpropionate), 2,2'-azobis(2-methylbutyronitrile), benzoylperoxide and lauroyl peroxide, a reaction may be carried out at 50 to 150° C. for 1 to 20 hours. After the reaction, treatment may also be carried out according to a conventional method for polymer acquisition.

[Coloring Composition]

The coloring composition of the present invention is the one containing at least one kind of the compound or the polymer of the present invention. The coloring composition can be used suitably for a color filter. The coloring composition is capable of forming an excellent colored cured film having heat resistance. Therefore, the coloring composition of the present invention can be used in an applications of color pixel formation such as a color filter used in a liquid crystal display (LCD) or a solid-state imaging element (CCD, CMOS, and the like), or in applications of printing ink, inkjet ink, paint, and the like; and particularly, it is suitable for the color filter of the liquid crystal display. Still more, the coloring composition of the present invention can also be used as a colored resin molded product by molding to a sheet, a film, a bottle, a cup, and the like, using a conventionally known molding method. Accordingly, it can also be used in applications of spectacles, contact lens, color contact lens, and the like; and it can be used in similar applications also by making a multi-layered structure with a known resin. In addition, it can also be used in applications of, for example, an optical film, a hair coloring agent, a labeling material for a compound or a biomaterial, a material of an organic solar battery, and the like. The coloring composition of the present invention may contain an additive used in this field usually, and the like, depending on each application, besides the compound or the polymer of the present invention.

For example, in the case where the coloring composition of the present invention is used as a colored resin, the coloring composition of the present invention is preferably the one which contains at least one or more kinds of the compound or the polymer of the present invention, as well as which is mixed with other resins, and more preferably the one which has one or more kinds of the polymer of the present invention and is mixed with other resins. The other resins are not especially limited, and include, for example, a polyolefin resin, a polystyrene resin, a polyester resin, a polyamide resin, a polyurethane resin, a polycarbonate resin, an epoxy resin, an acrylic resin, an acrylonitrile resin, an ABS resin, and the like. More specifically, a homopolymer or a copolymer derived from the compound represented by the general formula (2), the general formula (3), the general formula (4), and/or the general formula (5) is preferable, and the homopolymer derived from the compound represented by the general formula (2), the general formula (3), the general formula (4), or the general formula (5) is more preferable. As the homopolymer, the homopolymer derived from the compound represented by the general formula (2) is preferable, and the homopolymer derived from the compound represented by the general formula (2') is more preferable. In addition, in the case of mixing with the other resins, mixing ratio thereof may be set appropriately depending on desired color of the colored resin. In the case of using the coloring composition of the present invention as the colored resin, it may be used after molding it by a molding method known per se. Further, the coloring composition of the present invention, may contain an additive usually used in this field, such as a lubricant, an antistatic agent, a UV inhibitor, an antioxidant, a light stabilizer, a dispersing agent, a processing stabilizer, a processing aid, an impact modifier, fillers, a reinforcing agent, a flameproofing agent, a plasticizer, a foaming agent, and the like, besides the compound or the polymer of the present invention and the other resins as needed, within a range not interfering with the objects and effect of the present invention. The coloring composition of the present invention has less elution of a dye even in contact with a solvent and excellent weather resistance, in the case where it is used as the colored resin.

For example, in the case where the coloring composition of the present invention is used in an application of color pixel formation, the coloring composition of the present invention may contain, as needed, a pigment, a polymerization initiator, a solvent, a binder resin, a radically polymerizable monomer or oligomer, or a cross-linking agent; and, the coloring composition contains 1 to 50%, preferably 5 to 30% of the compound or the polymer of the present invention, relative to weight of the coloring composition. It should be noted that, weight of the coloring composition referred to herein means weight of solid components excluding the solvent, and means the same hereafter in the present invention.

The above-described pigment may be any pigment that is used to prepare a colored pattern of blue color or green color, and includes, for example, a phthalocyanine type pigment, and the like. The phthalocyanine type pigment includes the one containing magnesium, titanium, iron, cobalt, nickel, copper, zinc, or aluminum in central metal; and specifically includes C.I. pigment blue 15, C.I. pigment blue 15:1, C.I. pigment blue 15:2, C.I. pigment blue 15:3, C.I. pigment blue 15:4, C.I. pigment blue 15:5, C.I. pigment blue 15:6. C.I. pigment blue 16, C.I. pigment blue 17:1, C.I. pigment blue 75, C.I. pigment blue 79, C.I. pigment green 7, C.I. pigment green 36, C.I. pigment green 37, C.I. pigment green 58, chloroaluminum phthalocyanine, hydroxyaluminum phthalocyanine, aluminum phthalocyanine oxide, and zinc phthalocyanine; and among them, C.I. pigment blue 15, C.I. pigment blue 15:6, pigment blue 15:1, C.I. pigment blue 15:2 and C.I. pigment green 58 are preferable, and C.I. pigment blue 15:6 and C.I. pigment green 58 are particularly preferable.

Content of the pigment is 10 to 50% by weight, and preferably 10 to 30% by weight, relative to weight of the coloring composition.

In the case where the coloring composition of the present invention contains the pigment, it is preferable to contain a pigment dispersant. The pigment dispersant includes, for example, polyamide amine and a salt thereof, polycarboxylic acid and a salt thereof, a high molecular weight unsaturated acid ester, modified polyurethane, modified polyester, modified poly(meth)acrylate, a (meth)acrylic copolymer, a naphthalene sulfonic acid/formalin condensate, a polyoxyethylene alkyl phosphoric acid ester, a polyoxyethylene alkylamine, an alkanol amine, and the like. The pigment dispersant may be used alone, or in combination of two or more kinds. Content thereof is usually 1 to 80% by weight, and preferably 10 to 60% by weight, relative to weight of the pigment.

As the above-described polymerization initiator, a known thermal polymerization initiator or a photo polymerization initiator can be used, and a photo polymerization initiator is preferable. Specifically, it includes an acetophenone type such as diethoxyacetophenone, 2-hydroxy-2-methyl-1-phenylpropane-1-one, benzyldimethylketal, 1-(4-isopropylphenyl)-2-hydroxy-2-methylpropane-1-one, 4-(2-hydroxyethoxy)phenyl-(2-hydroxy-2-propyl)ketone, 1-hydroxycyclohexyl-phenylketone, 2-methyl-2-morpholino(4-thiomethylphenyl)propane-1-one and 2-benzyl-2-dimethylamino-1-(4-morpholinophenyl)-butanone; a benzoin type such as benzoin, benzoin isopropyl ether and benzoin isobutyl ether; an acylphosphine oxide type such as 2,4,6-trimethylbenzoyldiphenyl phosphine oxide; a benzyl, a methyl phenylglyoxylate type; a benzophenone type such as benzophenone, methyl o-benzoylbenzoate, 4-phenylbenzophenone, 4,4'-dichlorobenzophenone, hydroxybenzophenone, 4-benzoyl-4'-methyl-diphenylsulfide, acrylated benzophenone, 3,3',4,4'-tetra(tert-butylperoxycarbonyl) benzophenone and 3,3'-dimethyl-4-methoxybenzophenone; a thioxanthone type such as 2-isopropylthioxanthone, 2,4-dimethylthioxanthone, 2,4-diethylthioxanthone and 2,4-dichlorothioxanthone; an aminobenzophenone type such as Michler's ketone and 4,4'-diethylaminobenzophenone; an oxime ester type such as 1-[4-(phenylthio)phenyl]-1,2-octanedione-2-(o-benzoyloxime) and 1-[6-(2-methylbenzoyl)-9-ethyl-9H-carbazol-3-yl]ethanone-o-acetyloxime; 10-butyl-2-chloroacridone, 2-ethylanthraquinone, 9,10-Phenanthrenequinone, camphor quinone; and the like.

The polymerization initiator may be contained alone, or in two or more kinds. Content thereof is 1 to 50% by weight, and preferably 5 to 30% by weight, relative to weight of the coloring composition.

The above-described solvent may be selected appropriately depending on the components contained in the coloring composition. Specifically, it includes, for example, ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate methyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutanoate, ethyl 2-oxobutaanoate, diethylene glycol dimethyl ether, tetrahydrofuran, ethylene, glycol monomethyl ether, ethylene glycol monoethyl ether, methylcellosolve acetate, ethylcellosolve acetate, diethylene glycol monomethyl ether; diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, methyl ethyl ketone, cyclohexanone, 2-heptanone, 3-heptanone, and the like. Content of the solvent is an amount that concentration of the coloring composition of the present invention attains 10% by weight to 80% by weight in the solvent.

The above-described binder resin may be any one which is soluble in an alkaline developing solution used in producing a color filter, and includes, for example, an ethylenically unsaturated monomer having at least one of a carboxy group or a hydroxy group; a copolymer of the ethylenically unsaturated monomer and an ethylenically unsaturated monomer having an aromatic hydrocarbon group or an aliphatic hydrocarbon group; the one having an epoxy group at the side chain or the terminal, and the like, of the copolymer; and the one to which an acrylate is added; and the like. They may be used alone, or in combination of two or more kinds.

Specific examples of the ethylenically unsaturated monomer having the carboxy group include unsaturated monocarboxylic acids such as acrylic acid, methacrylic acid, benzyl methacrylate, crotonic acid, α-chloroacrylic acid, ethacrylic acid and cinnamic acid; unsaturated dicarboxylic acids (anhydrides) such as maleic acid, maleic anhydride, fumaric acid, itaconic acid, itaconic anhydride, citraconic acid, citraconic anhydride and mesaconic acid; tri or more polyvalent unsaturated carboxylic acids (anhydrides), 2-(meth)acryloyloxyethyl hexahydrophthalate, 2-methacryloyloxyethyl 2-hydroxypropylphthalate, 2-acryloyloxyethyl 2-hydroxyethylphthalate; and the like.

Content of the binder resin is 10% by weight to 50% by weight, and preferably 20% by weight to 50% by weight, relative to weight of the coloring composition.

The above-described radically polymerizable monomer or oligomer includes, as one example, polyethylene glycol diacrylate (the one having 2 to 14 ethylene groups), polyethylene glycol dimethacrylate (the one having 2 to 14 ethylene groups), trimethylolpropane diacrylate, trimethylolpropane dimethacrylate, trimethylolpropane triacrylate, trimethylolpropane trimethacrylate, trimethylolpropane ethoxytriacrylate, trimethoxylolpropane ethoxytrimethacrylate, trimethylolpropane propoxytriacrylate, trimethylolpropane propoxytrimethacrylate, tetramethylolmethane triacrylate, tetramethylolmethane trimethacrylate, tetramethylolmethane tetraacrylate, tetramethylolmethane tetramethacrylate, polypropyleneglycol diacrylate (the one having 2 to 14 propylene groups), polypropylene glycol dimethacrylate (the one having 2 to 14 propylene groups), dipentaerythritol pentaacrylate, dipentaerythritol pentamethacrylate, dipentaerythritol hexaacrylate, dipentaerythritol hexamethacrylate, ethoxylated pentaerythritol tetraacrylate (the one having 40 or less ethoxy groups), propoxylated pentaerythritol tetraacrylate (the one having 40 or less propoxy groups), ethoxylated trimethylolpropane triacrylate (the one having 40 or less ethoxy groups), propoxylated trimethylolpropane triacrylate (the one having 40 or less propoxy groups), bisphenol A polyoxyethylene diacrylate, bisphenol A polyoxyethylene dimethacrylate, bisphenol A dioxyethylene diacrylate, bisphenol A dioxyethylene dimethacrylate, bisphenol A trioxyethylene diacrylate, bisphenol A trioxyethylene dimethacrylate, bisphenol A decaoxyethylene diacrylate, bisphenol A decaoxyethylene dimethacrylate, isocyanuric acid ethoxy modified triacrylate, an esterified product with a polyvalent carboxylic acid (phthalic anhydride, and the like) and a compound having a hydroxy group and an ethylenically unsaturated group (β-hydroxyethyl acrylate, β-hydroxyethyl methacrylate, and the like), an alkyl ester of acrylic acid or methacrylic acid (acrylic acid methyl ester, methacrylic acid methyl ester, acrylic acid ethyl ester, methacrylic acid ethyl ester, acrylic acid butyl ester, methacrylic acid butyl ester, acrylic acid 2-ethylhexyl ester, methacrylic acid 2-ethylhexyl ester, and the like), 2-hydroxyethyl acrylate, 2-hydroxyethyl methacrylate, phenoxyethyl acrylate, phenoxyethyl methacrylate, N,N-dimethylacrylamide, N,N-dimethylaminoethyl acrylate, a quaternary chloride of N,N-dimethylaminoethyl acrylate by methyl chloride, a quaternary chloride of N,N-dimethylaminopropylacrylamide by methyl chloride, acryloylmorpholine, N-isopropylacrylamide, N,N-diethylacrylamide, and the like.

The above-described cross-linking agent includes, for example, (a) an epoxy resin, (b) a melamine compound, a guanamine compound, a glycoluril compound or a urea compound, substituted with at least one substituent selected from methylol group, an alkoxymethyl group and an acyloxymethyl group, and (c) a phenol compound, a naphthol compound or a hydroxyanthracene compound, substituted with at least one substituent selected from a methylol group, an alkoxymethyl group and an acyloxymethyl group; and among them, a polyfunctional epoxy resin is preferable.

Content of the cross-linking agent is 10% by weight to 50% by weight, and preferably 20% by weight to 50% by weight, relative to weight of the coloring composition.

The coloring composition of the present invention may contain a polymerization inhibitor, a surfactant, an additive, and the like, in addition to the above-described ones, and they are not especially limited, as long as they are those known per se, and the use amount is not limited, as long as it is the amount usually used in this field.

The coloring composition of the present invention is prepared by mixing with the above-described components.

The present invention is described in further detail by Examples below, however, the present invention should not be limited to these Examples.

EXAMPLES

Example 1

Synthesis of a Polymerizable Coloring Matter of the Present Invention (Dye Monomer 2)
(1) Construction of a Dye Skeleton Into a round-bottom flask equipped with a stirring apparatus, 10.0 g of 2-(1,3,3,-trimethylindoline-2-ylidene)acetaldehyde (compound 1) (5.0 mmol, produced by Wako Pure Chemical Industries, Ltd.), 6.8 g of 2-(4-aminophenyl)ethanol (compound 2) (5.0 mmol, produced by Tokyo Chemical Industry Co., Ltd.), and 50 mL of acetic acid were added, and reacted at 40° C. for 3.5 hours. Still more, methylene chloride (produced by Wako Pure Chemical Industries, Ltd.) and a saturated sodium chloride aqueous solution were added for extraction of a product into an organic layer, and then the organic layer was washed twice with saturated sodium bicarbonate aqueous solution, and washed with the saturated sodium chloride aqueous solution. After that the solvent was removed by concentration under reduced pressure to obtain 15.3 g (yield: 86%) of a Basic Yellow 13 derivative (compound 3) as a brown solid.

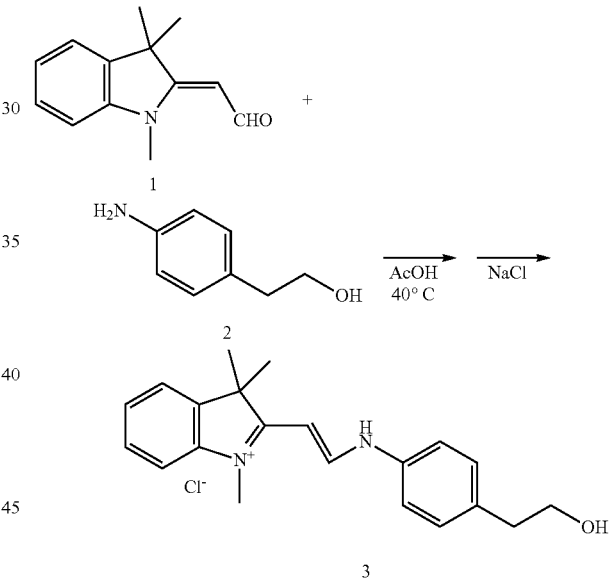

(2) Introduction of a Polymerizable Group

Into a round-bottom flask equipped with a stirring apparatus, 10.0 g (28 mmol) of the Basic Yellow 13 derivative (compound 3), 7.8 g of NK ester SA (2-methacryloyloxyethyl succinate, compound 4) (34 mmol, produced by Shin-Nakamura Chemical Co., Ltd.), 1.0 g of 4-dimethylaminopyridine (8.2 mmol, produced by Wako Pure Chemical Industries, Ltd.), 9.2 g of 1-ethyl-3-(3-dimethylaminopropyl)carbodiimide hydrochloride (WSC) (48 mmol, produced by Toyobo Co., Ltd.), and 100 mL of methylene chloride (produced by Wako Pure Chemical Industries, Ltd.) were added, and reacted at room temperature for 24 hours. Next, ion-exchanged water was added for washing an organic layer, and the solvent was removed by concentration under reduced pressure. Still more, after purification using a silica gel column, the solvent was removed by concentration under reduced pressure to obtain 3.0 g (yield: 30%) of a dye monomer 1 (compound 5) as a brown solid.

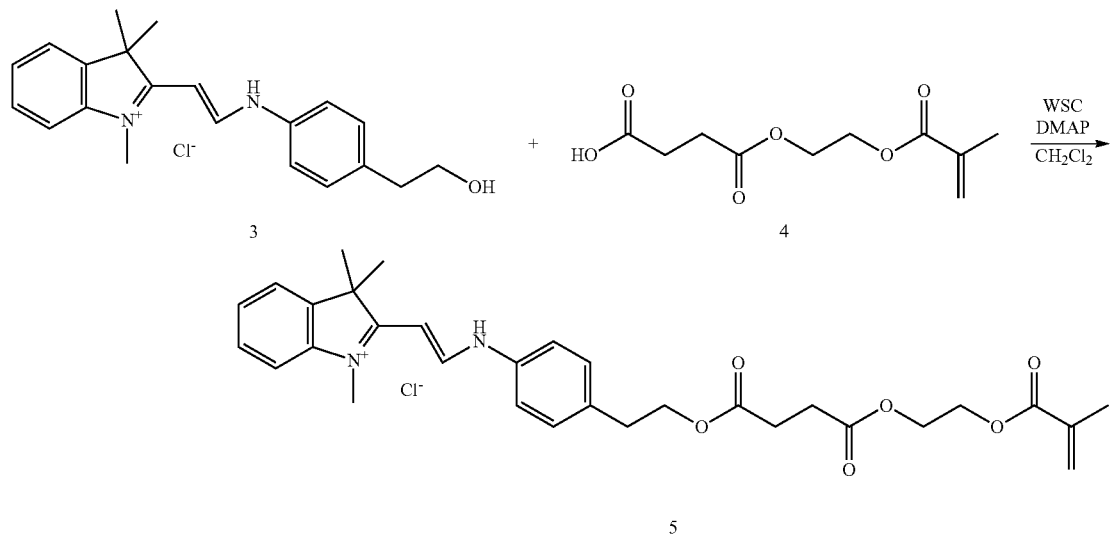

(3) Salt Exchange Reaction

In a round-bottom flask equipped with a stirring apparatus, 100 mL of methylene chloride was added to 2.0 g (3.5 mmol) of the dye monomer 1 (compound 5) for dissolution. Into there, 3.8 g of lithium salt of tetrakis(pentafluorophenyl)boron(IV) (5.5 mmol, produced by Tosoh Finechem Corp.) and 100 mL of ion-exchanged water were added for dissolution, and then reacted at room temperature for 30 minutes. The resulting organic solvent was subjected to liquid separation, and washed with ion-exchanged water, and then the solvent was removed by concentration under reduced pressure to obtain 2.6 g (yield: 61%) of a dye monomer 2 (compound 6) as a brown solid, having a tetrakis(pentafluorophenyl)boron(IV) anion as a counter anion.

Example 2

Synthesis of a Polymerizable Coloring Matter (Dye Monomer 3)

(1) Salt Exchange Reaction

In a round-bottom flask equipped with a stirring apparatus, 100 mL of methylene chloride was added to 6.0 g (16.8 mmol) of the Basic Yellow 13 derivative (compound 3) obtained similarly as in Example 1 (1), for dissolution. Into there, 11.5 g of lithium salt of tetrakis(pentafluorophenyl)boron(IV) (16.8 mmol, produced by Tosoh Finechem Corp.) and 100 mL of ion-exchanged water were added for dissolution, and then reacted at room temperature for 30 minutes. The resulting organic solvent was subjected to liquid separation, and washed with ion-exchanged water, and then the solvent was removed by concentration under reduced pres-

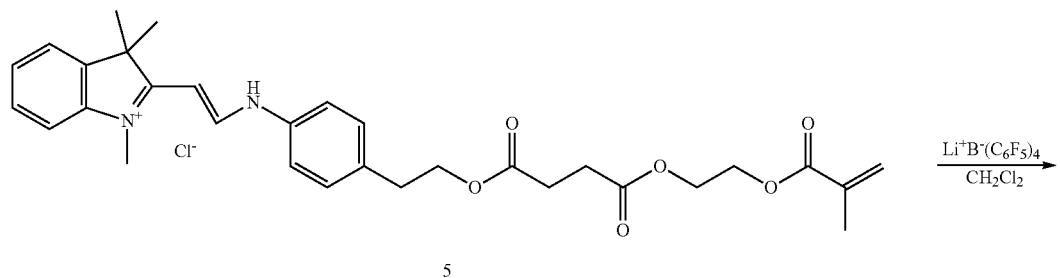

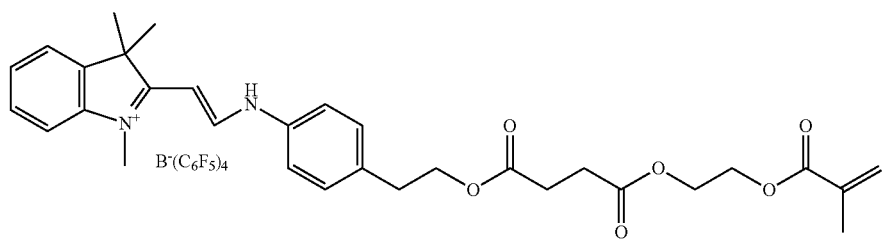

sure to obtain 12.8 g (yield: 76%) of a Basic Yellow 13 derivative having a tetrakis(pentafluorophenyl)boron(IV) anion as a counter anion (compound 7).

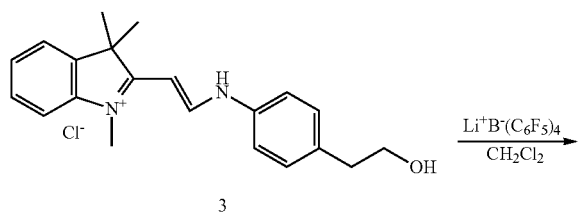

(2) Introduction of a Polymerizable Group

Into a round-bottom flask equipped with a stirring apparatus, 4.0 g of crushed molecular sieves 3A (produced by Wako Pure Chemical Industries, Ltd.), 2.0 g of the Basic Yellow 13 derivative having a tetrakis(pentafluorophenyl)boron(IV) anion (compound 7) synthesized in (1), 0.52 g of methacrylic acid chloride (5.0 mmol, produced by Wako Pure Chemical Industries, Ltd.), and 40 mL of 1,2-dichloroethane were added, and reacted under reflux at 80° C. for 4 hours. After cooling down to room temperature, saturated sodium bicarbonate aqueous solution was added for neutralization, followed by washing with ion-exchanged water until a water layer attained neutral. The solvent was removed by concentration under reduced pressure to obtain 2.0 g (yield: 94%) of a dye monomer 3 (compound 9) as a brown solid.

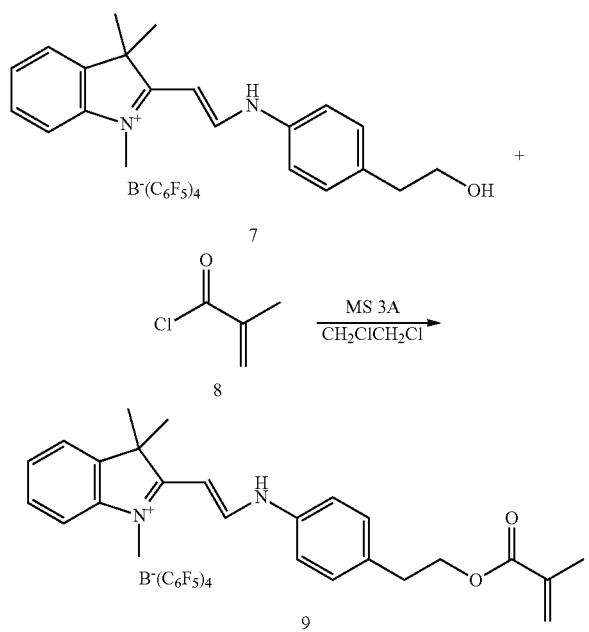

Example 3

Synthesis of a Polymerizable Coloring Matter (Dye Monomer 4)

(1) Introduction of a Polymerizable Group

Into a round-bottom flask equipped with a stirring apparatus, 13.7 g of 4-aminobenzoic acid (compound 10) (produced by Wako Pure Chemical Industries, Ltd.), 13.7 g of 2-hydroxyethyl methacrylate (compound 11) (produced by Wako Pure Chemical Industries, Ltd.), 3.7 g of 4-dimethylaminopyridine (produced by Wako Pure Chemical Industries, Ltd.), and 180 mL of methylene chloride (produced by Wako Pure Chemical Industries, Ltd.) were added. Into there, 23.0 g of 1-ethyl-3-(3-dimethylaminopropyl)carbodiimide hydrochloride (produced by Toyobo Co., Ltd.) was added, and reacted at −5° C. for 7 hours. After warming up to room temperature, a generated solid was filtrated, and then ethyl acetate (produced by Wako Pure Chemical Industries, Ltd.) and water were added for extraction and washing, and the solvent was removed by concentration under reduced pressure. The resulting solid was recrystallized from methanol to obtain 9.1 g (yield: 37%) of an ester (compound 12) as a white solid.

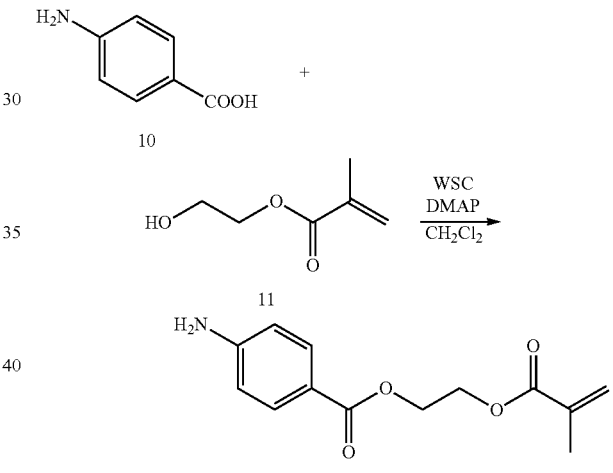

(2) Construction of a Dye Skeleton, and Salt Exchange Reaction

Into a round-bottom flask equipped with a stifling apparatus, 2.0 g of 2-(1,3,3,-trimethylindoline-2-ylidene)acetaldehyde (compound 1) (produced by Wako Pure Chemical Industries, Ltd.), 2.5 g of the ester (compound 12) synthesized in (1), and 10 mL of acetic acid (produced by Wako Pure Chemical Industries, Ltd.) were added, and reacted at 55° C. for 5 hours. After cooling down to room temperature, methylene chloride (produced by Wako Pure Chemical Industries, Ltd.) and a saturated sodium chloride aqueous solution were added, and stirred at room temperature for 1 hour. Next, the organic layer was washed with water and sodium bicarbonate aqueous solution. Into there, 7.5 g of lithium salt of tetrakis(pentafluorophenyl)boron(IV) (produced by Tosoh Finechem Corp.) was added, and stirred at room temperature for 0.5 hour. After washing the reaction solution with water, the solvent was removed by concentration under reduced pressure to obtain 10.9 g (yield: 98%) of a dye monomer 4 (compound 13) as a dark orange solid.

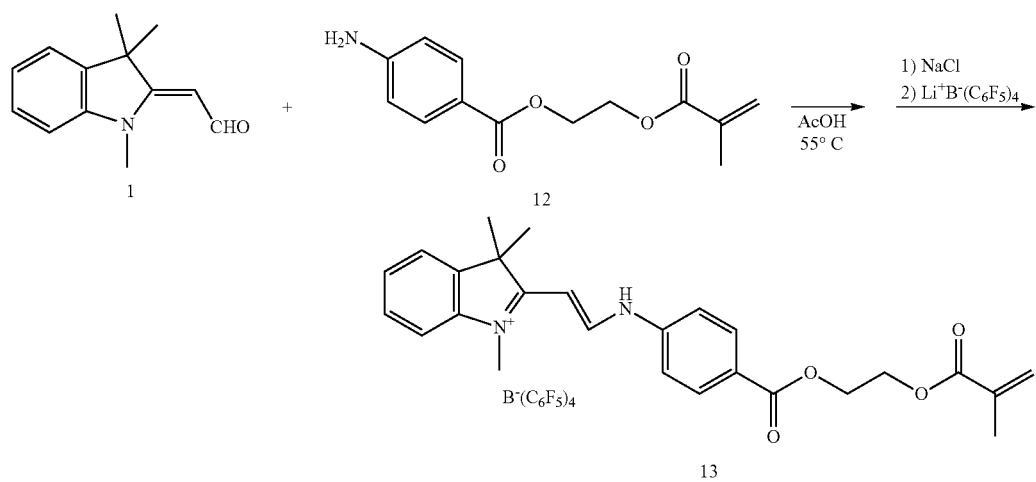

Example 4

Synthesis of a Polymerizable Coloring Matter (Dye Monomer 5)

(1) Introduction of a Polymerizable Group

Into a round-bottom flask equipped with a stirring apparatus, 7.2 g of 4-nitrophenylacetic acid (compound 14) (produced by Wako Pure Chemical Industries, Ltd.), 5.2 g of 2-hydroxyethyl methacrylate (compound 11) (produced by Wako Pure Chemical Industries, Ltd.), 1.5 g of 4-dimethylaminopyridine (produced by Wako Pure Chemical Industries, Ltd.), and 80 mL of methylene chloride (produced by Wako Pure Chemical Industries, Ltd.) were added. Into there, 11.5 g of 1-ethyl-3-(3-dimethylaminopropyl)carbodiimide hydrochloride (produced by Toyobo Co., Ltd.) was added and reacted at room temperature for 2 hours. Water was added to the reaction solution for extraction and washing, and the solvent was removed by concentration under reduced pressure to obtain 11.7 g (yield: 100%) of an ester (compound 15) as a black oil.

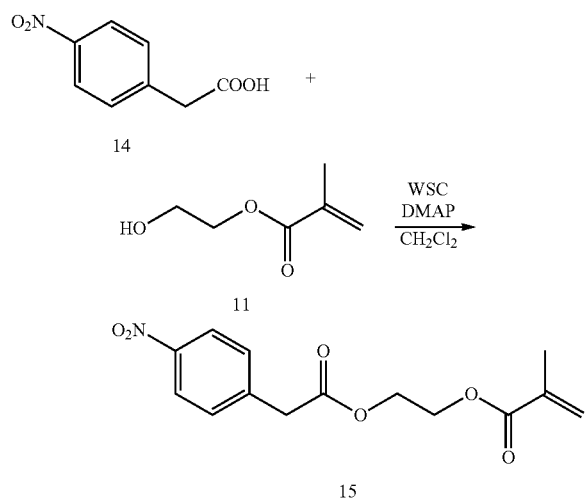

(2) Reduction Reaction

Into a round-bottom flask equipped with a stirring apparatus, 11.7 g of the ester (compound 15) obtained in (1), and 90 mL of acetic acid (produced by Wako Pure Chemical Industries, Ltd.) were added, and then 14.4 g of zinc powder (produced by Wako Pure Chemical Industries, Ltd.) was charged dividedly. After a reaction at room temperature for 5 hours, insoluble matters were filtrated, and 150 mL of methylene chloride (produced by Wako Pure Chemical Industries, Ltd.) was added, and then the solution was washed with water. Still more, into a water layer obtained by extraction and liquid separation using 1 mol/L hydrochloric acid, an aqueous sodium hydroxide was added to adjust pH 10, and then it was extracted with 150 mL of methylene chloride. The solvent was removed by concentration under reduced pressure to obtain 5.7 g (yield: 54%) of orange liquid (compound 16).

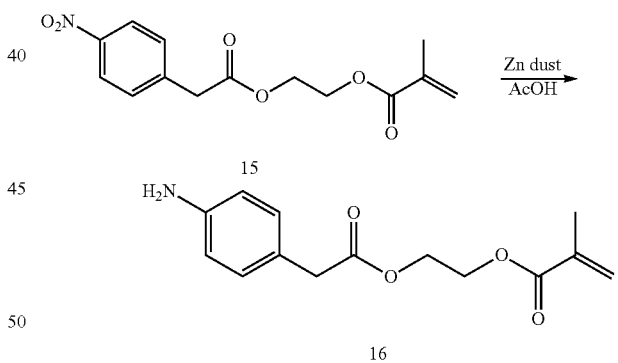

(3) Construction of a Dye Skeleton, and Salt Exchange Reaction

Into a round-bottom flask equipped with a stirring apparatus, 2.0 g of 2-(1,3,3,-trimethylindoline-2-ylidene)acetaldehyde (compound 1) (produced by Wako Pure Chemical Industries, Ltd.), 2.6 g of the aniline derivative (compound 16) synthesized in (2), and 10 mL of acetic acid (produced by Wako Pure Chemical Industries, Ltd.) were added, and reacted at 55° C. for 6 hours. After cooling down to room temperature, methylene chloride (produced by Wako Pure Chemical Industries, Ltd.) and a saturated sodium chloride aqueous solution were added and stirred at room temperature for 1 hour, and the organic layer was washed with water and sodium bicarbonate aqueous solution. Into there, 7.5 g of lithium salt of tetrakis(pentafluorophenyl)boron (IV) (produced by Tosoh Finechem Corp.) was added, and stirred at room temperature for 0.5 hour. After washing the reaction solution with water, the solvent was removed by concentration under reduced pressure to obtain 10.8 g (yield: 96%) of a dye monomer 5 (compound 17) as a dark orange solid.

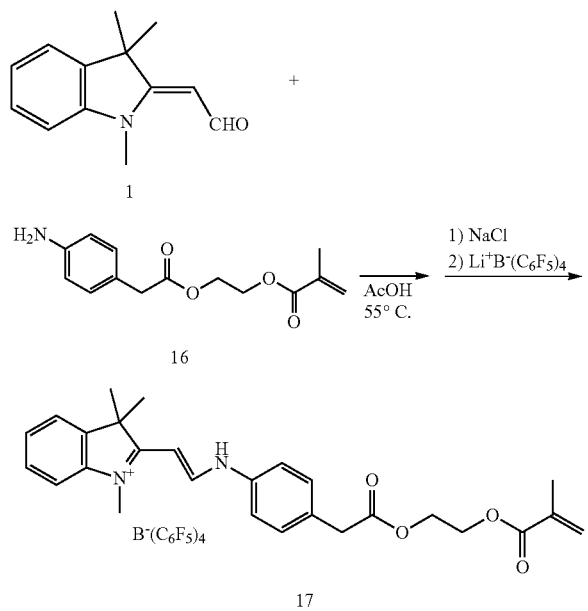

Example 5

Synthesis of a Polymerizable Coloring Matter (Dye Monomer 6)

(1) Introduction of a Polymerizable Group

Into a round-bottom flask equipped with a stirring apparatus, 2.0 g of 3-methoxy-4-nitrophenylacetic acid (compound 18) (produced by Tokyo Chemical Industry Co., Ltd.), 1.3 g of 2-hydroxyethyl methacrylate (compound 11) (produced by Wako Pure Chemical Industries, Ltd.), 0.4 g of 4-dimethylaminopyridine (produced by Wako Pure Chemical Industries, Ltd.), and 80 mL of methylene chloride (produced by Wako Pure Chemical Industries, Ltd.) were added. Into there, 2.9 g of 1-ethyl-3-(3-dimethylaminopropyl)carbodiimide hydrochloride (produced by Toyobo Co., Ltd.) was added, and reacted at room temperature for 3 hours. Still more, water was added for washing, and then the solvent was removed by concentration under reduced pressure to obtain 3.1 g (yield: 100%) of an ester (compound 19) as a brown oil.

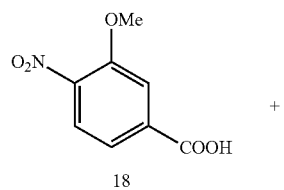

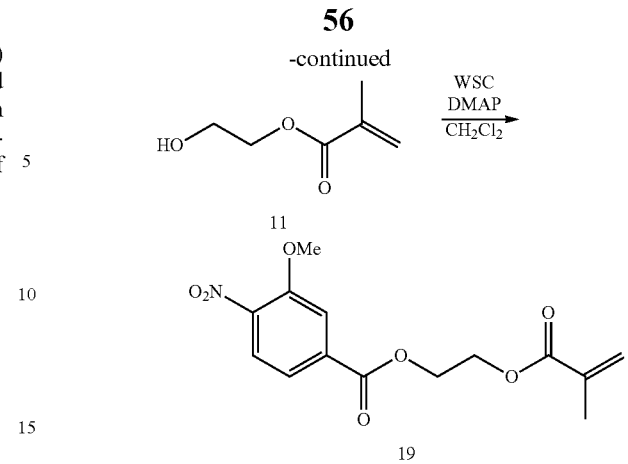

(2) Reduction Reaction

Into a round-bottom flask equipped with a stirring apparatus, 3.1 g of the ester (compound 19) obtained in (1), and 20 mL of acetic acid (produced by Wako Pure Chemical Industries, Ltd.) were added, and then 3.3 g of zinc powder (produced by Wako Pure Chemical Industries, Ltd.) was charged dividedly. After a reaction at room temperature for 5 hours, insoluble matters were filtrated, and 30 mL of methylene chloride (produced by Wako Pure Chemical Industries, Ltd.) was added, and then the solution was washed with water and sodium bicarbonate aqueous solution. The solvent was removed by concentration under reduced pressure to obtain 1.9 g (yield: 68%) of orange liquid (compound 20).

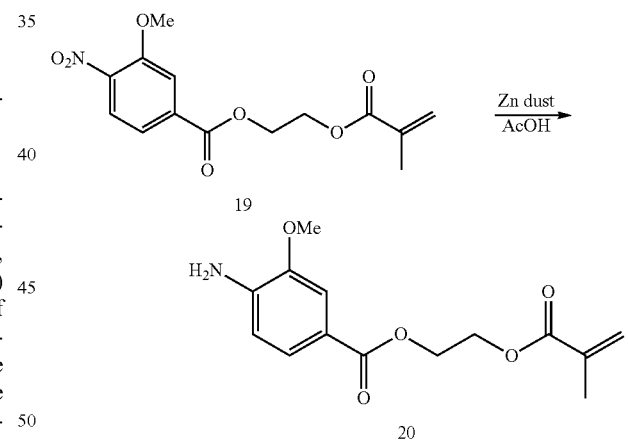

(3) Construction of a Dye Skeleton, and Salt Exchange Reaction

Into a round-bottom flask equipped with a stirring apparatus, 1.8 g of 2-(1,3,3,-trimethylindoline-2-ylidene)acetaldehyde (compound 1) (produced by Wako Pure Chemical Industries, Ltd.), 2.5 g of the aniline derivative (compound 20) synthesized in (2), and 10 mL of acetic acid (produced by Wako Pure Chemical Industries, Ltd.) were added, and reacted at 55° C. for 6 hours. After cooling down to room temperature, methylene chloride (produced by Wako Pure Chemical Industries, Ltd.) and a saturated sodium chloride aqueous solution were added and stirred at room temperature for 1 hour, and the organic layer was washed with water and washed more with sodium bicarbonate aqueous solution. Into there, 6.7 g of lithium salt of tetrakis(pentafluorophenyl)boron (IV) (produced by Tosoh Finechem Corp.) was added, and stirred at room temperature for 0.5 hour. After washing the reaction solution with water, the solvent was removed by concentration under reduced pressure to obtain 9.9 g (yield: 97%) of a dye monomer 6 (compound 21) as a dark orange solid.

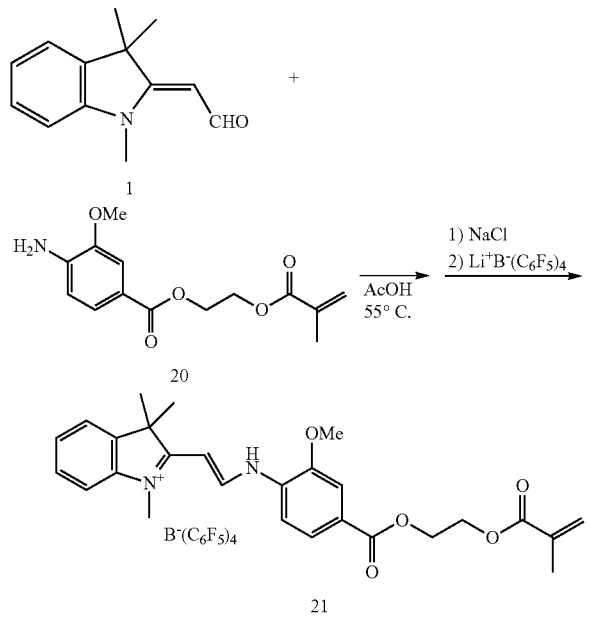

Example 6

Synthesis of a Polymerizable Coloring Matter (Dye Monomer 7)

(1) Introduction of a Polymerizable Group

Into a round-bottom flask equipped with a stirring apparatus, 2.7 g of 4,5-dimethoxy-2-nitrobenzoic acid (compound 22) (produced by Wako Pure Chemical Industries, Ltd.), 1.6 g of 2-hydroxyethyl methacrylate (compound 11) (produced by Wako Pure Chemical Industries, Ltd.), 0.4 g of 4-dimethylaminopyridine (produced by Wako Pure Chemical Industries, Ltd.) and 20 mL of methylene chloride (produced by Wako Pure Chemical Industries, Ltd.) were added. Into there, 3.5 g of 1-ethyl-3-(3-dimethylaminopropyl)carbodiimide hydrochloride (produced by Toyobo Co., Ltd.) was added, and reacted at room temperature for 3 hours. Still more, water was added for washing, and then the solvent was removed by concentration under reduced pressure to obtain 3.1 g (yield: 77%) of an ester (compound 23) as a brown oil.

(2) Reduction Reaction

Into a round-bottom flask equipped with a stirring apparatus, 2.8 g of the ester (compound 23) obtained in (1), and 20 mL of acetic acid (produced by Wako Pure Chemical Industries, Ltd.) were added, and then 3.2 g of zinc powder (produced by Wake Pure Chemical Industries, Ltd.) was charged dividedly. After a reaction at room temperature for 4 hours, insoluble matters were filtrated, and 70 mL of methylene chloride (produced by Wake Pure Chemical Industries, Ltd.) was added, and then the solution was washed with water and sodium bicarbonate aqueous solution. Next, the solvent was removed by concentration under reduced pressure to obtain a brown solid containing oil component. It was washed with 30 mL of methanol (produced by Wake Pure Chemical Industries, Ltd.), and dried under reduced pressure to obtain 0.8 g (yield: 33%) of a pale brown solid (compound 24).

(3) Construction of a Dye Skeleton, and Salt Exchange Reaction

Into a round-bottom flask equipped with a stirring apparatus, 0.4 g of 2-(1,3,3,-trimethylindoline-2-ylidene)acetaldehyde (compound 1) (produced by Wako Pure Chemical Industries, Ltd.), 0.8 g of the aniline derivative (compound 24) synthesized in (2), and 15 mL of acetic acid (produced by Wako Pure Chemical Industries, Ltd.) were added, and reacted at 55° C. for 4 hours. After cooling down to room temperature, methylene chloride (produced by Wako Pure Chemical Industries, Ltd.) and a saturated sodium chloride aqueous solution were added and stirred at room temperature for 1 hour, and the organic layer was washed with water and washed more with sodium bicarbonate aqueous solution. Into there, 1.6 g of lithium salt of tetrakis(pentafluorophenyl)boron (IV) (produced by Tosoh Finechem Corp.) was added, and stirred at room temperature for 0.5 hour. After washing the reaction solution with water, the solvent was removed by concentration under reduced pressure to obtain 2.8 g (yield: 88%) of a dye monomer 7 (compound 25) as a dark orange solid.

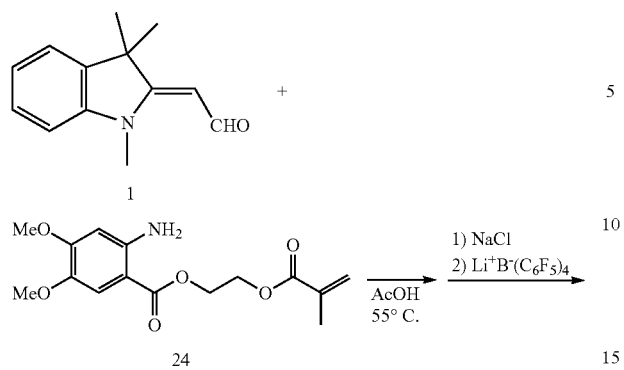

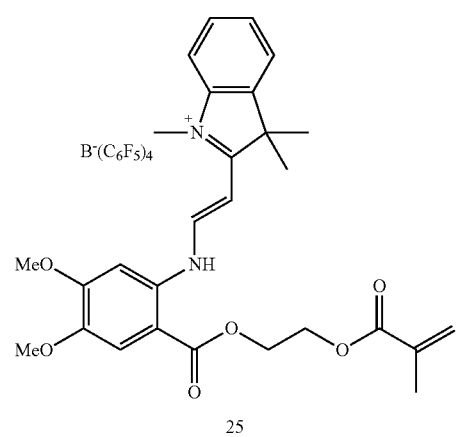

Example 7

Synthesis of a Polymerizable Coloring Matter (Dye Monomer 8)

(1) Introduction of a Polymerizable Group

Into a round-bottom flask equipped with a stirring apparatus, 3.9 g of 2-nitrocinnamic acid (compound 26) (produced by Wako Pure Chemical Industries, Ltd.), 2.6 g of 2-hydroxyethyl methacrylate (compound 11) (produced by Wako Pure Chemical Industries, Ltd.), 0.7 g of 4-dimethylaminopyridine (produced by Wako Pure Chemical Industries, Ltd.), and 40 mL of methylene chloride (produced by Wako Pure Chemical Industries, Ltd.) were added. Still more, 5.8 g of 1-ethyl-3-(3-dimethylaminopropyl)carbodiimide hydrochloride (produced by Toyobo Co., Ltd.) was added thereto, and reacted at room temperature for 2 hours. Next, water was added for washing, and then the solvent was removed by concentration under reduced pressure to obtain 6.1 g (yield: 100%) of an ester (compound 27) as a yellow oil.

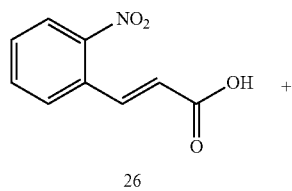

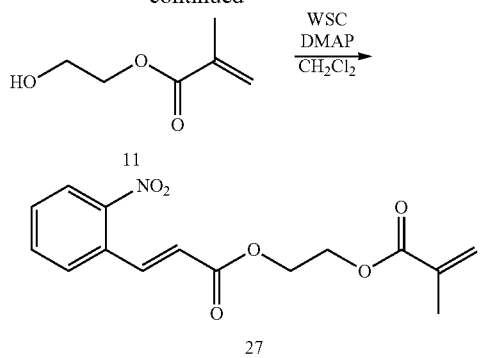

(2) Reduction Reaction

Into a round-bottom flask equipped with a stirring apparatus, 3.1 g of the ester (compound 27) obtained in (1), and 21 mL of acetic acid (produced by Wako Pure Chemical Industries, Ltd.) were added, and then 3.3 g of zinc powder (produced by Wako Pure Chemical Industries, Ltd.) was charged dividedly. After a reaction at room temperature for 5 hours, insoluble matters were filtrated, and 50 mL of methylene chloride (produced by Wako Pure Chemical Industries, Ltd.) and water were added for washing. Still more, after neutralization with sodium bicarbonate aqueous solution, the solvent was removed by concentration under reduced pressure to obtain 2.5 g (yield: 91%) of brown oil (compound 28).

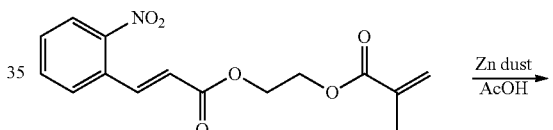

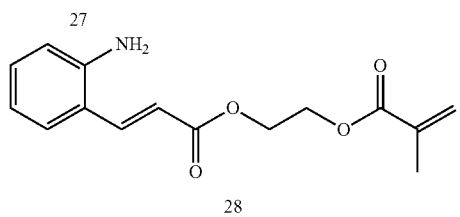

(3) Construction of a Dye Skeleton, and Salt Exchange Reaction

Into a round-bottom flask equipped with a stirring apparatus, 0.7 g of 2-(1,3,3,-trimethylindoline-2-ylidene)acetaldehyde (compound 1) (produced by Wako Pure Chemical Industries, Ltd.), 1.0 g of the aniline derivative (compound 28) synthesized in (2), and 10 mL of acetic acid (produced by Wako Pure Chemical Industries, Ltd.) were added, and reacted at 55° C. for 5 hours. Still more, methylene chloride (produced by Wako Pure Chemical Industries, Ltd.) and a saturated sodium chloride aqueous solution were added and stirred at room temperature for 1 hour, and then the organic layer was washed with water and washed more with sodium bicarbonate aqueous solution, and 7.5 g of lithium salt of tetrakis(pentafluorophenyl)boron (IV) (produced by Tosoh Finechem Corp.) was added thereto, and stirred at room temperature for 0.5 hour. After washing the reaction solution with water, the solvent was removed by concentration under reduced pressure to obtain 4.0 g (yield: 97%) of a dye monomer 8 (compound 29) as a dark orange solid.

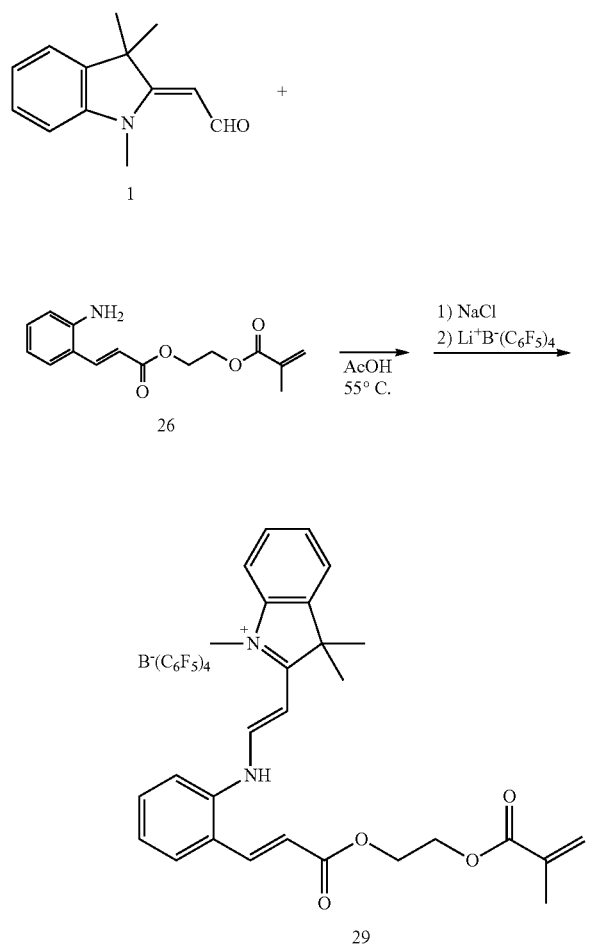

Example 8

Synthesis of a Polymerizable Coloring Matter (Dye Monomer 9)

(1) Introduction of a Polymerizable Group

Into a round-bottom flask equipped with a stilling apparatus, 1.9 g of 4-nitrocinnamic acid (compound 30) (produced by Tokyo Chemical Industry Co., Ltd.), 20 mL of toluene (produced by Wake Pure Chemical Industries, Ltd.), and 1 mL of N,N-dimethylformamide (produced by Wako Pure Chemical Industries, Ltd.) were added, and warmed up to 60° C. Into there, 1.3 g of thionyl chloride (produced by Wake Pure Chemical Industries, Ltd.) was added and the solution was stirred at 70° C. for 2 hours. Excess thionyl chloride was removed by concentration under reduced pressure to prepare a toluene solution of 4-nitrocinnamoyl chloride (compound 31). Into another round-bottom flask equipped with a stirring apparatus, 1.3 g of 2-hydroxyethyl methacrylate (compound 11) (produced by Tokyo Chemical Industry Co., Ltd.), 1.0 g of trimethylamine (produced by Tokyo Chemical Industry Co., Ltd.), and 10 mL of toluene were added and cooled with water, and the toluene solution of 4-nitrocinnamoyl chloride (compound 32) prepared previously was dropped thereto, and then subjected to reaction at room temperature for 3 hours. After the deposit was filtrated, it was washed with water, and the solvent was removed by concentration under reduced pressure to obtain 2.3 g (yield: 77%) of an orange oil compound 32.

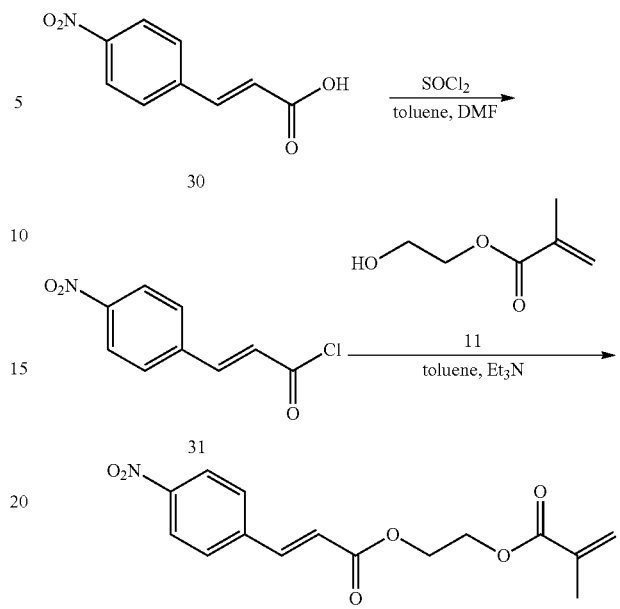

(2) Reduction Reaction

Into a round-bottom flask equipped with a stirring apparatus, 2.3 g of the ester (compound 32) obtained in (1), and 20 mL of acetic acid (produced by Wako Pure Chemical Industries, Ltd.) were added, and then 2.9 g of zinc powder (produced by Wako Pure Chemical Industries, Ltd.) was charged dividedly. After a reaction at room temperature for 5 hours, insoluble matters were filtrated, and 50 mL of methylene chloride (produced by Wako Pure Chemical Industries, Ltd.) and water were added for washing. Still more, after neutralization with sodium bicarbonate aqueous solution, the solvent was removed by concentration under reduced pressure to obtain 1.8 g (yield: 86%) of brown oil (compound 33).

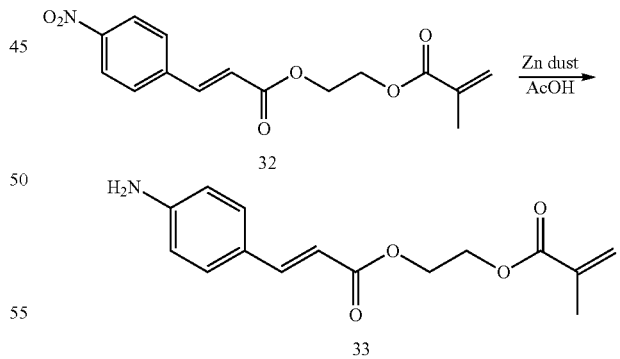

(3) Construction of a Dye Skeleton, and Salt Exchange Reaction

Into a round-bottom flask equipped with a stirring apparatus, 1.3 g of 2-(1,3,3,-trimethylindoline-2-ylidene)acetaldehyde (compound 1) (produced by Wako Pure Chemical Industries, Ltd.), 1.8 g of the aniline derivative (compound 33) synthesized in (2), and 15 mL of acetic acid (produced by Wako Pure Chemical Industries, Ltd.) were added, and reacted at 55° C. for 5 hours. Next, methylene chloride (produced by Wako Pure Chemical Industries, Ltd.) and a saturated sodium chloride aqueous solution were added and stirred at room temperature for 1 hour, and then the organic layer was washed with water and washed more with sodium bicarbonate aqueous solution, and 4.8 g of lithium salt of tetrakis(pentafluorophenyl)boron (IV) (produced by Tosoh Finechem Corp.) was added thereto, and stirred at room temperature for 0.5 hour. After washing the reaction solution with water, the solvent was removed by concentration under reduced pressure to obtain 7.1 g (yield: 98%) of a dye monomer 9 (compound 34) as a dark orange solid.

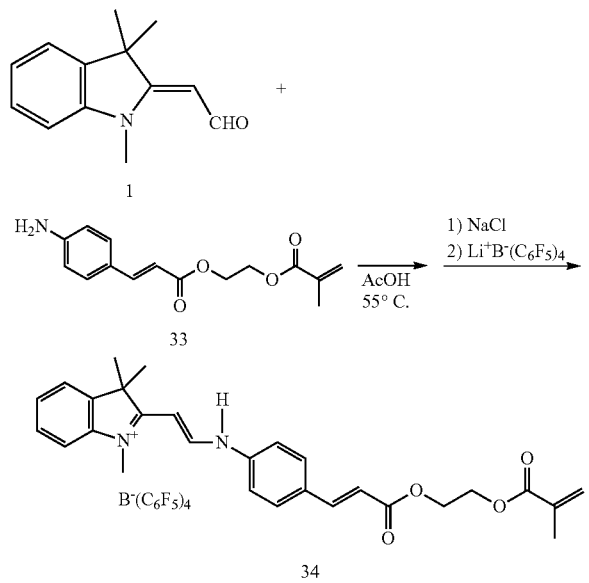

Example 9

Synthesis of a Dye Polymer 2

Into a 200 mL round-bottom flask equipped with a stirring apparatus, a cooling condenser, a thermometer and a nitrogen introducing tube, 27.9 g of propylene glycol monomethyl ether acetate (produced by Wako Pure Chemical Industries, Ltd.) was charged, and heated until inner temperature reaches to 90° C. under nitrogen gas flow. Next, a solution mixed with 3.0 g of the dye monomer 2 (compound 6), 50.1 g of benzyl methacrylate (produced by Wako Pure Chemical Industries, Ltd.), 6.9 g of methacrylic acid (produced by Wako Pure Chemical Industries, Ltd.), 9.6 g of dimethyl 2,2'-azobis(2-methylpropionate) (polymerization initiator V-601, produced by Wako Pure Chemical Industries, Ltd.), and 27.9 g of propylene glycol monomethyl ether acetate (produced by Wako Pure Chemical Industries, Ltd.) was dropped therein taking 2 hours. After that, the resulting solution was reacted at 90° C. for 2 hours. After the reaction, the solution was cooled down to room temperature, and 48.6 g of propylene glycol monomethyl ether acetate was added for dilution to obtain a dye polymer (dye monomer 2/benzyl methacrylate/methacrylic acid=3.0/50.1/6.9). This was referred to as a dye polymer 2 solution.

Example 10

Synthesis of a Dye Polymer 3

A dye polymer (dye monomer 3/benzyl methacrylate/methacrylic acid=3.0/50.1/6.9) was obtained similarly as in Example 9, except for using 3.0 g of the dye monomer 3 obtained in Example 2, instead of 3.0 g of the dye monomer 2. This was referred to as a dye polymer 3 solution.

Comparative Example 1

Synthesis of Basic Yellow 13

Into a round-bottom flask equipped with a stirring apparatus, 5.0 g of 2-(1,3,3,-trimethylindoline-2-ylidene)acetaldehyde (compound 1) (24.8 mmol, produced by Wako Pure Chemical Industries, Ltd.), 3.1 g of p-anisidine (compound 35) (25.1 mmol, produced by Tokyo Chemical Industry Co., Ltd.), and 25 mL of acetic acid (produced by Wako Pure Chemical Industries, Ltd.) were added, and reacted at 40° C. for 4 hours. Next, methylene chloride (produced by Wako Pure Chemical Industries, Ltd.) and a saturated sodium chloride aqueous solution were added for extraction of an object material into an organic layer, and then the organic layer was washed twice with saturated sodium bicarbonate aqueous solution, and washed with a saturated sodium chloride aqueous solution. After that, the solvent was removed by concentration under reduced pressure to obtain 7.3 g (yield: 86%) of Basic Yellow 13 (compound 36) as a brown solid.

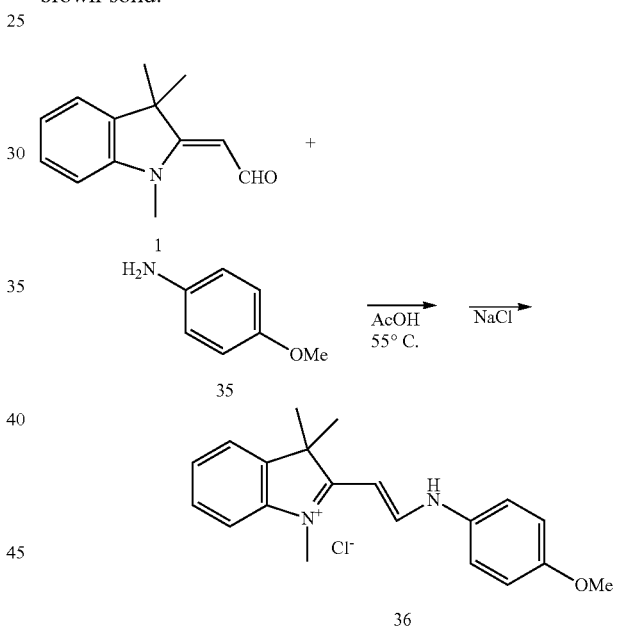

Example 11

Evaluation of Heat Resistance of the Dye Monomer 2 (230° C. for 0.5 Hour)

Heat resistance of the dye monomer 2 obtained in Example 1 was evaluated as follows:
(1) Synthesis of a Polymer not Containing a Dye.

Into a 500 mL round-bottom flask equipped with a stirring apparatus, a cooling condenser, a thermometer and a nitrogen introducing tube, 98.5 g of propylene glycol monomethyl ether acetate was charged, and heated until inner temperature reaches to 90° C. under nitrogen gas flow. Next, a solution mixed with 186.2 g of benzyl methacrylate, 25.6 g of methacrylic acid, 33.9 g of dimethyl 2,2'-azobis(2-methylpropionate) (polymerization initiator V-601, produced by Wako Pure Chemical Industries, Ltd.) and 98.5 g of propylene glycol monomethyl ether acetate was dropped therein taking 2 hours. After that, the resulting solution was reacted at 90° C. for 2 hours. Next, temperature was raised to 100° C., and the reaction was continued for 1 hour. After the reaction, the solution was cooled down to room temperature, and 171.5 g of propylene glycol monomethyl ether acetate was added for dilution to obtain a pale yellow transparent polymer solution. This was referred to as a polymer A. It should be noted that concentration of non-volatile component of the polymer A was 35.9%.

(2) Preparation of a Mixed Solution of the Dye Monomer

To prepare a mixed solution B of the dye monomer, 0.5 g of the dye monomer 2, 52.9 g of the polymer A and 3.2 g of propylene glycol monomethyl ether acetate were mixed.

(3) Evaluation of Heat Resistance

The mixed solution B of the dye monomer was spin coated onto 3 inch glass wafer (Eagle XG, manufactured by Corning Inc.), and then dried for 90 seconds on a hot plate heated at 90° C. to obtain a thin film having a film thickness of 1 μm. Absorbance (λa) at the maximum absorption wavelength of the resulting thin film was measured using a spectrophotometer (Spectrophotometer UV-2550, manufactured by Shimadzu Corp.). After that, the glass wafer was heated for 30 minutes on the hot plate heated at 230° C., and then absorbance (λb) at the maximum absorption wavelength was measured again. From values of λa and λb measured, dye residual ratio (%) was determined by the following equation. Result thereof is shown in Table 1. It should be noted that the maximum absorption wavelength (nm) in methanol (MeOH) solution is also shown in the table.

Dye residual ratio (%)=(λb/λa)×100

Examples 12 to 16

Evaluation of Heat Resistance of the Dye Monomers 3 to 6 and 9 (230° C. for 0.5 Hour)

Heat resistance of each of the dye monomers 3 to 6 and 9 was evaluated by operation according to the method of Example 11, except for using the dye monomers 3 to 6 and 9, instead of the dye monomer 2 in Example 11. Results thereof and the maximum absorption wavelength (nm) in methanol (MeOH) solution are shown in Table 1, together with the result of Example 11.

Examples 17 to 18

Maximum Absorption Wavelength of the Dye Monomers 7 and 8

The maximum absorption wavelength (nm) in methanol (MeOH) solution of the monomers 7 and 8 is shown in Table 1.

Example 19

Evaluation of Heat Resistance of Dye Polymers 2 and 3 (230° C. for 0.5 Hour)

Heat resistance of the dye polymer 2 solution obtained in Example 9 was evaluated as follows.

That is, the resulting dye polymer 2 solution was spin coated onto 3 inch glass wafer (Eagle XG, manufactured by Corning Inc.), and then dried for 90 seconds on a hot plate heated at 90° C. to obtain a thin film having a film thickness of 1 μm. Absorbance (λa) at the maximum absorption wavelength of the resulting thin film was measured using a spectrophotometer (Spectrophotometer UV-2550, manufactured by Shimadzu Corp.), and after that, the glass wafer was heated for 30 minutes on the hot plate heated at 230° C., and then absorbance (λb) at the maximum absorption wavelength was measured again. From values of λa and λb measured, dye residual ratio (%) was determined by the following equation. Result thereof is shown in Table 1, together with the results of Examples 11 to 18.

Dye residual ratio (%)=(λb/λa)×100

Example 20

Evaluation of Heat Resistance of Dye Polymer 3 (230° C. for 0.5 Hour)

Heat resistance of the dye polymer 3 was evaluated by operation according to the method of Example 19, except for using the dye polymer 3 solution, instead of the dye polymer 2 solution in Example 19. Result thereof is shown in Table 1, together with the results of Examples 11 to 19.

Comparative Example 2

Evaluation of Heat Resistance of Basic Yellow 13 (230° C. for 0.5 Hour)

Heat resistance of Basic Yellow 13 was evaluated similarly as in Example 5, except for using 0.5 g of Basic Yellow 13, instead of 0.5 g of the dye monomer 2. Result thereof and the maximum absorption wavelength (nm) in methanol (MeOH) solution are shown in Table 1, together with the results of Examples 11 to 20.

TABLE 1

| | Sample | Dye residual ratio (%) | Maximum absorption wavelength (nm) in MeOH solution |
|---|---|---|---|
| Example 11 | Dye monomer 2 | 81 | 413 |
| Example 12 | Dye monomer 3 | 89 | 414 |
| Example 13 | Dye monomer 4 | 95 | 417 |
| Example 14 | Dye monomer 5 | 93 | 413 |
| Example 15 | Dye monomer 6 | 100 | 422 |
| Example 16 | Dye monomer 9 | 88 | 430 |
| Example 17 | Dye monomer 7 | — | 425 |
| Example 18 | Dye monomer 8 | — | 397 |
| Example 19 | Dye polymer 2 | 92 | — |
| Example 20 | Dye polymer 3 | 90 | — |
| Com. Expl. 2 | Basic Yellow 13 | 0 | 414 |

As shown in Table 1, it has been revealed that in the case of Basic Yellow 13, which is a well-known yellow dye, there was no remaining dye after heating, while the dye monomers and polymers of the present invention exhibited high dye residual ratio, and thus have high heat resistance. That is, it has been revealed that the compound of the present invention having a polymerizable group as well as tetrakis(pentafluorophenyl)boron as an anion, and the polymer derived from the compound have superior heat resistance. In addition, it has also been that the dye polymer has higher heat resistance as compared with the dye monomer.

In addition, as shown in Table 1, the dye monomers 2 to 9 have the maximum absorption wavelength of 410 to 430 nm. Accordingly, a transparent material using these dyes alone or in combination is capable of reducing transmission of light having specific wavelength.

Example 21

Synthesis of a Dye Polymer 4

Into a 2000 mL round-bottom flask equipped with a stirring apparatus, a cooling condenser, a thermometer and a nitrogen introducing tube, 105 g of propylene glycol monomethyl ether acetate (produced by Daicel Corp.) was charged, and heated until inner temperature reaches to 90° C. under nitrogen gas flow. Next, 15 g of the dye monomer 4, 285 g of methyl methacrylate (produced by Wako Pure Chemical Industries, Ltd.), and 15 g of 2,2'-azobis(2-methylpropionic acid methyl) (product name: V-601, produced by Wako Pure Chemical Industries, Ltd.) were mixed, and the mixed solution was dropped in the round-bottom flask at 95° C. taking 2 hours. After that, the resulting solution was reacted at 95° C. for 2 hours. After the reaction, the solution was cooled down to room temperature, and dissolved in 1000 g of ethyl acetate. After the mixed solution was poured into 4600 mL of n-hexane, a generated precipitate was filtered, and the solution was dried under reduced pressure to obtain 315 g of the dye polymer 4 containing about 5 parts by weight of the dye monomer 4.

Example 22

Molding of a Colored Plate Containing the Dye Polymer 4

To obtain colored resin pellets, 0.5 part by weight of the dye polymer 4 obtained above and 99.5 parts by weight of a commercially available poly(methyl methacrylate) resin (ACRYPET MD001, produced by Mitsubishi Rayon Co., Ltd.) were melt blended using a same direction rotation type twin screw extruder. Next, the resulting resin pellets were molded using an electromotive injection molding apparatus to prepare a colored plate with a size of 150 mm×150 mm, with a thickness of 2 mm.

Comparative Example 3

Molding of a Colored Plate Containing Basic Yellow 13

A colored plate was prepared similarly as in Example 22, except for using 0.025 part by weight of Basic Yellow 13 and 100 parts by weight of a poly(methyl methacrylate) resin, instead of 0.5 part by weight of the dye polymer 4.

Example 23

Elution Resistance Test of a Colored Plate Containing the Dye Polymer 4

The colored plate prepared in Experiment 22 was cut to a size of 40 mm×30 mm, with a thickness of 2 mm, and then it was immersed in 80 mL of an aqueous ethanol solution, which was prepared b mixing 50 parts of ethanol and 50 parts of ion-exchanged water, and stored in a thermostatic bath at 40° C. for 200 hours. The ethanol solution was taken out and measured an optical spectrum thereof using a spectrophotometer (Spectrophotometer UV-2500, manufactured by Shimadzu Corp.).

Using absorbance ($\lambda a$) at the maximum absorption wavelength of the measurement sample and gram absorption coefficient ($\varepsilon$) measured in advance, weight of the dye monomer 4 dined into the aqueous ethanol solution was calculated, to calculate elution ratio (%), based on weight of the dye monomer 4 contained in the resin colored plate immersed, by the following equation.

Elution ratio (%)=[($\lambda a \times 0.08/\varepsilon$)]/(weight of the dye contained in the colored plate)]×100

(note) Weight of the dye contained in the colored plate×weight of the plate×0.00025

Comparative Example 4

Elution Resistance Test of a Colored Plate Containing Basic Yellow 13

Elution ratio of Basic Yellow 13 was calculated by similar operation as in Example 23, except for using the colored plate prepared in Comparative Example 3. Result thereof is shown in Table 2, together with the result of Example 23.

TABLE 2

|  | Measurement object | Elution ratio (%) |
| --- | --- | --- |
| Example 23 | Colored plate containing dye polymer 4 | 0.03 |
| Com. Expl. 4 | Colored plate containing Basic Yellow 13 | 3.36 |

As shown in Table 2, it has been revealed that elution ratio from the colored plate containing the dye polymer 4 of the present invention is significantly low, as compared with elution ratio from Basic Yellow 13. That is, it has been shown that the colored plate using the dye polymer of the present invention is capable of providing a colored material superior in elution resistance.

Example 24

Weathering Test

The colored plate prepared in Example 22 was cut to a size of 65 mm×65 mm, with a thickness of 2 mm, and subjected to accelerated weathering test of a xenon arc lamp type under the following condition, using an apparatus [Ci4000 (manufactured by Atlas Material Testing Technology LLC)] specified in JIS B7754: 1991.
(1) Test Condition
Irradiance: 50 w/m$^2$ (300 to 400 nm)
Filter glass: (inside) borosilicate S-type, (outside) soda lime
Black panel temperature: 63±2° C.
Chamber temperature: 38±2° C.
Relative humidity: 50±10% RH
Test period: 50 hours
(2) Color Measurement Condition
Measurement: Reflection measurement (8°: de)
Standard light: $D_{65}$
Measurement hole diameter: φ5 mm As for the molded plate before the test and after the test for 50 hours, color difference was measured according to the L*a*b* color system of JIS Z8730:2009, using a color meter CC-i (manufactured by Suga Test Instruments Co., Ltd.) to calculate $\Delta L^*$, $\Delta a^*$ and $\Delta b^*$, which indicate amount of change of L* value, a* value, b* value, before and after the test; and color difference ($\Delta E^*ab$) was determined by the following equation. Result thereof is shown in Table 3.

Color difference ($\Delta E^*ab$)=[($\Delta L^*)^2+(\Delta a^*)^2+(\Delta b^*)^2]^{1/2}$

TABLE 3

|  | Test period | | | | | | Color difference |
| --- | --- | --- | --- | --- | --- | --- | --- |
|  | 0 h | | | 50 h | | | |
|  | L* | a* | b* | L* | a* | b* | ΔE*ab |
| Colored plate containing dye polymer | 76.75 | −22.65 | 52.63 | 78.64 | −21.74 | 51.27 | 2.50 |

TABLE 3-continued

| | Test period | | | | | | Color difference |
|---|---|---|---|---|---|---|---|
| | 0 h | | | 50 h | | | |
| | L* | a* | b* | L* | a* | b* | ΔE*ab |
| Colored plate containing Basic Yellow 13 | 74.82 | −19.95 | 49.89 | 77.39 | −18.14 | 49.18 | 3.22 |

When color difference is within 3, it can be judged that there is no color change. Accordingly, it has been revealed that the colored plate containing the dye polymer has superior weather resistance, as compared with the molded plate containing Basic Yellow 13.

The invention claimed is:

1. A compound represented by the following general formula (1):

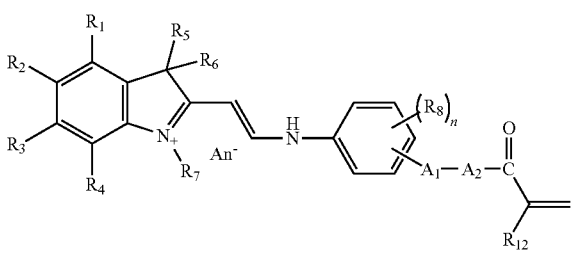

(1)

wherein $R_1$ to $R_4$ each independently represent a hydrogen atom, a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms;

$R_5$ and $R_6$ each independently represent a hydrogen atom, an alkyl group having 1 to 6 carbon atoms, an arylalkyl group having 7 to 13 carbon atoms, or a phenylalkyl group having 7 to 9 carbon atoms, which has an alkyl group in addition to the alkyl group in the phenylalkyl group and having 1 to 6 carbon atoms, a nitro group, a halogeno group or a cyano group as a substituent of the phenyl group; n represents an integer of 0 to 4;

$R_7$ represents a hydrogen atom, an alkyl group having 1 to 6 carbon atoms, an arylalkyl group having 7 to 13 carbon atoms, an alkyl group having 1 to 6 carbon atoms, which has an alkoxy group having 1 to 6 carbon atoms, a hydroxy group, a carboxy group, a halogeno group, a cyano group, an amide group or an alkyloxycarbonyl group having 2 to 4 carbon atoms, as a substituent, or a phenylalkyl group having 7 to 9 carbon atoms, which has an alkoxy group having 1 to 6 carbon atoms, a halogeno group or an amide group, as a substituent of the phenyl group;

n pieces of $R_8$ each independently represent a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms;

$R_{12}$ represents a hydrogen atom or a methyl group;

$A_1$ represents an alkylene group having 1 to 21 carbon atoms which has at least one group selected from —O—, —OCO—, —COO—, a vinylene group and an arylene group in the chain; an alkylene group having 1 to 21 carbon atoms which has at least one group selected from —O—, —OCO—, —COO— and an arylene group in the chain, and also has a hydroxy group as a substituent;

an alkylene group having 1 to 21 carbon atoms; or an alkylene group having 1 to 21 carbon atoms which has a hydroxy group as a substituent; $A_2$ represents —NH— or —O—;

$An^-$ represents an anion containing an aryl group having an electron-withdrawing substituent, a sulfonyl group having an electron-withdrawing substituent, or a halogenated alkyl group.

2. The compound according to claim 1, wherein the electron-withdrawing substituent in $An^-$ is a halogen atom.

3. The compound according to claim 1, wherein the electron-withdrawing substituent in $An^-$ is a fluorine atom.

4. The compound according to claim 1, wherein $An^-$ is a quaternary boron anion.

5. The compound according to claim 1, wherein $An^-$ is a tetrakis(perfluorophenyl)borate anion.

6. A polymer having a monomer unit derived from the compound represented by the following general formula (1):

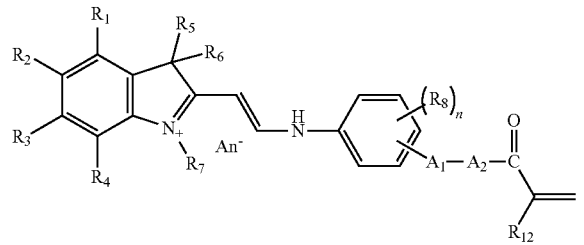

(1)

wherein $R_1$ to $R_4$ each independently represent a hydrogen atom, a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms;

$R_5$ and $R_6$ each independently represent a hydrogen atom, an alkyl group having 1 to 6 carbon atoms, an arylalkyl group having 7 to 13 carbon atoms, or a phenylalkyl group having 7 to 9 carbon atoms, which has an alkyl group in addition to the alkyl group in the phenylalkyl group and having 1 to 6 carbon atoms, a nitro group, a halogeno group or a cyano group as a substituent of the phenyl group; n represents an integer of 0 to 4;

$R_7$ represents a hydrogen atom, an alkyl group having 1 to 6 carbon atoms, an arylalkyl group having 7 to 13 carbon atoms, an alkyl group having 1 to 6 carbon atoms, which has an alkoxy group having 1 to 6 carbon atoms, a hydroxy group, a carboxy group, a halogeno group, a cyano group, an amide group or an alkyloxycarbonyl group having 2 to 4 carbon atoms, as a substituent, or a phenylalkyl group having 7 to 9 carbon atoms, which has an alkoxy group having 1 to 6 carbon atoms, a halogeno group or an amide group, as a substituent of the phenyl group;

n pieces of $R_8$ each independently represent a nitro group, a halogeno group, a cyano group, an amide group, a carboxy group, an alkyl group having 1 to 6 carbon atoms, an alkoxy group having 1 to 6 carbon atoms, an alkyloxycarbonyl group having 2 to 4 carbon atoms, an alkylcarbonyloxy group having 2 to 4 carbon atoms, or an arylcarbonyl group having 7 to 10 carbon atoms;

$R_{12}$ represents a hydrogen atom or a methyl group;

$A_1$ represents an alkylene group having 1 to 21 carbon atoms which has at least one group selected from —O—, —OCO—, —COO—, a vinylene group and an arylene group in the chain; an alkylene group having 1 to 21 carbon atoms which has at least one group selected from —O—, —OCO—, —COO— and an arylene group in the chain, and also has a hydroxy group as a substituent;

an alkylene group having 1 to 21 carbon atoms; or an alkylene group having 1 to 21 carbon atoms which has a hydroxy group as a substituent; $A_2$ represents —NH— or —O—;

$An^-$ represents an anion containing an aryl group having an electron-withdrawing substituent, a sulfonyl group having an electron-withdrawing substituent, or a halogenated alkyl group.

7. The polymer according to claim 6, wherein the electron-withdrawing substituent in $An^-$ is a halogen atom.

8. The polymer according to claim 6, wherein the electron-withdrawing substituent in $An^-$ is a fluorine atom.

9. The polymer according to claim 6, wherein $An^-$ is a quaternary boron anion.

10. The polymer according to claim 6, wherein $An^-$ is a tetrakis(perfluorophenyl)borate anion.

11. The polymer according to claim 6, wherein the polymer is a copolymer.

12. The polymer according to claim 11, wherein the copolymer is a copolymer having 1 to 2 kinds of monomer units derived from a compound represented by the following general formula (2), the general formula (3), the general formula (4) or the general formula (5), and the monomer unit derived from the compound represented by the above-described general formula (1), as configuration components:

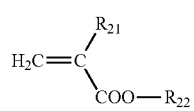
(2)

wherein $R_{21}$ represents a hydrogen atom or a methyl group; $R_{22}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 10 carbon atoms which has oxygen or no oxygen, a dialkylaminoalkyl group having 3 to 9 carbon atoms, a fluorinated alkyl group having 1 to 18 carbon atoms, or an N-alkylenephthalimide group having 1 to 6 carbon atoms, a group represented by the following general formula (2-1):

(2-1)

wherein $R_{23}$ represents an alkylene group having 1 to 3 carbon atoms; $R_{24}$ represents a phenyl group having a hydroxy group as a substituent or not having a substituent, or an alkyl group having 1 to 3 carbon atoms; and q represents an integer of 1 to 3, a group represented by the following general formula (2-2):

(2-2)

wherein $R_{25}$ to $R_{27}$ represent an alkyl group having 1 to 3 carbon atoms; $R_{28}$ represents an alkylene group having 1 to 3 carbon atoms, or a group represented by the following general formula (2-3):

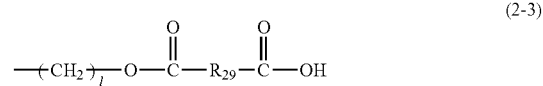
(2-3)

wherein l represents an integer of 1 to 6; $R_{29}$ represents a phenylene group or a cyclohexylene group;

(3)

wherein $R_{30}$ is the same as described above; $R_{31}$ represents a hydrogen atom or an alkyl group having 1 to 3 carbon atoms; $R_{32}$ represents a hydrogen atom, an alkyl group having 1 to 3 carbon atoms, a dialkylaminoalkyl group having 3 to 9 carbon atoms, or a hydroxyalkyl group having 1 to 6 carbon atoms; $R_{31}$ and $R_{32}$ may form a morpholino group, together with a nitrogen atom adjacent thereto;

(4)

wherein $R_{33}$ represents a phenyl group or a pyrrolidino group; and $R_{21}$ is the same as described above;

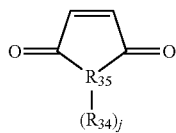 (5)

wherein $R_{35}$ represents a nitrogen atom or an oxygen atom; j represents 0 when $R_{35}$ is an oxygen atom, and 1 when $R_{35}$ is a nitrogen atom; $R_{34}$ represents a hydrogen atom, an alkyl group having 1 to 20 carbon atoms, a hydroxyalkyl group having 1 to 10 carbon atoms, a halogenated alkyl group having 1 to 10 carbon atoms, an alkylcycloalkyl group having 1 to 10 carbon atoms, a halogenated cycloalkyl group having 6 to 7 carbon atoms, an aryl group having 6 to 10 carbon atoms, an aryl group having 6 to 10 carbon atoms, which has an alkyl group having 1 to 6 carbon atoms as a substituent, or a halogenated aryl group having 6 to 10 carbon atoms.

13. A coloring composition comprising the compound according to claim 1.

14. A coloring composition for a color filter comprising the compound according to claim 1.

15. A colored resin comprising the compound according to claim 1.

16. A coloring composition comprising the polymer according to claim 6.

17. A coloring composition for a color filter comprising the polymer according to claim 6.

18. A colored resin comprising the polymer according to claim 6.

* * * * *